US008105813B2

(12) United States Patent
Diener et al.

(10) Patent No.: US 8,105,813 B2
(45) Date of Patent: Jan. 31, 2012

(54) MATERIALS AND METHODS FOR THE GENERATION OF FULLY 2′-MODIFIED NUCLEIC ACID TRANSCRIPTS

(75) Inventors: John L. Diener, Cambridge, MA (US); Anthony Dominic Keefe, Cambridge, MA (US); Kristin Thompson, Arlington, MA (US); Chunhua Wang, Acton, MA (US); Shuhao Zhu, Lincoln, MA (US)

(73) Assignee: Archemix Corp., Cambridge, MA (US)

( * ) Notice: Subject to any disclaimer, the term of this patent is extended or adjusted under 35 U.S.C. 154(b) by 1082 days.

(21) Appl. No.: 11/480,188

(22) Filed: Jun. 30, 2006

(65) Prior Publication Data

US 2007/0117112 A1    May 24, 2007

Related U.S. Application Data

(60) Provisional application No. 60/696,292, filed on Jun. 30, 2005.

(51) Int. Cl.
*C12N 9/12* (2006.01)

(52) U.S. Cl. .................... 435/194; 435/183; 435/69.1

(58) Field of Classification Search .................. None
See application file for complete search history.

(56) References Cited

U.S. PATENT DOCUMENTS

| | | | |
|---|---|---|---|
| 5,270,163 A | 12/1993 | Gold et al. .................. 435/6 |
| 5,385,834 A | 1/1995 | Ikeda ..................... 435/172.3 |
| 5,475,096 A | 12/1995 | Gold et al. ............... 536/23.1 |
| 5,496,938 A | 3/1996 | Gold et al. ............... 536/22.1 |
| 5,567,588 A | 10/1996 | Gold et al. .................. 435/6 |
| 5,580,737 A | 12/1996 | Polisky et al. ............. 435/6 |
| 5,637,459 A | 6/1997 | Burke et al. ................ 435/6 |
| 5,648,214 A | 7/1997 | Nieuwlandt et al. ........ 435/6 |
| 5,660,985 A | 8/1997 | Pieken et al. ............... 435/6 |
| 5,668,264 A | 9/1997 | Janjic et al. ............... 536/23.1 |
| 5,672,695 A | 9/1997 | Eckstein et al. ............ 536/24.5 |
| 5,674,685 A | 10/1997 | Janjic et al. ................ 435/6 |
| 5,683,867 A | 11/1997 | Biesecker et al. ........... 435/6 |
| 5,698,687 A | 12/1997 | Eckstein et al. ............ 536/25.3 |
| 5,705,537 A | 1/1998 | Hartman, Jr. et al. ........ 521/84.1 |
| 5,707,796 A | 1/1998 | Gold et al. .................. 435/6 |
| 5,763,177 A | 6/1998 | Gold et al. .................. 435/6 |
| 5,817,635 A | 10/1998 | Eckstein et al. ............. 514/44 |
| 5,827,661 A | 10/1998 | Blais ........................... 435/6 |
| 5,861,254 A | 1/1999 | Schneider et al. ........... 435/6 |
| 5,869,320 A | 2/1999 | Studier et al. .............. 435/252.33 |
| 5,958,691 A | 9/1999 | Pieken et al. ............... 435/6 |
| 6,011,020 A | 1/2000 | Gold et al. .................. 514/44 |
| 6,051,698 A | 4/2000 | Janjic et al. ................ 536/24.31 |
| 6,207,646 B1 | 3/2001 | Krieg et al. ................. 514/44 |
| 6,207,816 B1 | 3/2001 | Gold et al. ................. 536/24.1 |
| 6,214,806 B1 | 4/2001 | Krieg et al. ................. 514/44 |
| 6,229,002 B1 | 5/2001 | Janjic et al. ................ 536/23.1 |
| 6,239,116 B1 | 5/2001 | Krieg et al. ................. 514/44 |
| 6,366,530 B1 | 4/2002 | Sluiter et al. ............... 365/240 |
| 6,426,434 B1 | 7/2002 | Yoshida et al. ............. 564/71 |
| 6,429,199 B1 | 8/2002 | Krieg et al. ................. 514/44 |
| 6,498,148 B1 | 12/2002 | Raz ............................ 514/44 |
| 6,514,948 B1 | 2/2003 | Raz et al. ................... 514/44 |
| 6,562,575 B1 | 5/2003 | Dahl ........................... 435/6 |
| 6,653,292 B1 | 11/2003 | Krieg et al. ................. 514/44 |
| 6,867,027 B1 | 3/2005 | Hayashizaki et al. ........ 435/194 |
| 7,022,144 B2 | 4/2006 | Legrand et al. ............. 8/405 |
| 7,335,471 B2 | 2/2008 | Guillerez et al. ............ 435/6 |
| 2004/0180360 A1 | 9/2004 | Wilson et al. .............. 435/6 |
| 2004/0197804 A1 | 10/2004 | Keefe et al. ................ 435/6 |
| 2005/0037394 A1 | 2/2005 | Keefe et al. ................ 435/6 |
| 2006/0183702 A1 | 8/2006 | Diener et al. .............. 514/44 A |
| 2007/0117112 A1 | 5/2007 | Diener et al. .............. 435/6 |
| 2009/0081679 A1 | 3/2009 | Keefe et al. ................ 435/6 |

FOREIGN PATENT DOCUMENTS

| | | |
|---|---|---|
| WO | WO 91/19813 | 12/1991 |
| WO | WO 92/07065 | 4/1992 |
| WO | WO 98/18480 | 5/1998 |

OTHER PUBLICATIONS

Ngo et al. , The Protein Folding Problem and Tertiary Structure Prediction, 1994, Merz et al. (ed.), Birkhauser, Boston, MA, pp. 433 and 492-495.*
Bradford, M.M., "A Rapid and Sensitive Method for the Quantitation of Microgram Quantities of Protein Utilizing the Principle of Protein-Dye Binding", *Anal. Biochem.*, 72:248-254 (1976).
Bull et al., "Experimental Evolution Yields Hundreds of Mutations in a Functional Viral Genome", *J. Mol. Evol.*, 57:241-248 (2003).
Burmeister et al., "Direct in Vitro Selection of a 2′-O-Methyl Aptamer to VEGF", *Chem. Biol.*, 12:25-33 (2005).
Chelliserrykattil et al., "Evolution of a T7 RNA polymerase variant that transcribes 2′-O-methyl RNA", *Nat. Biotech.*, 22(9):1155-1160 (2004).
Cotton et al., "2′-O-methyl, 2′-O-ethyl oligoribonucleotides and phosphorothioate oligodeoxyribonucleotides as inhibitors of the in vitro U7 snRNP-dependent mRNA processing event", *Nuc. Acids Res.*, 19(10):2629-2635 (1991).
Froehler et al., "Synthesis of DNA via deoxynucleoside H-phosphonate intermediates", *Nuc. Acids Res.*, 14(13):5399-5407 (1986). Froehler, B.C., "Deoxynucleoside H-Phosphonate Diester Intermediates in the Synthesis of Internucleotide Phosphate Analogues", *Tet. Letters*, 27(46):5575-5578 (1986).
Greenwald et al., "Highly Water Soluble Taxol Derivatives: 7-Polyethylene Glycol Carbamates and Carbonates", *J. Org. Chem.*, 60:331-336 (1995).
Guillerez et al., "A mutation in T7 RNA polymerase that facilitates promoter clearance", *PNAS*, 102(17):5958-5963 (2005).
Harris et al., "Effect of Pegylation on Pharmaceuticals", *Nat. Rev.*, 2:214-221 (2003).
Hirose et al., "Rapid Synthesis of Trideoxyribonucleotide Blocks", *Tet. Letters*, 28:2449-2452 (1978).
Hobbs et al., "Polynucleotides containing 2′-amino-2′-deoxyribose and 2′-azido-2′-deoxyribose", *Biochem.*, 12(25):5138-5145 (1973).
Krieg, A.M., "CpG Motifs in Bacterial DNA and Their Immune Effects", *Annu. Rev. Immunol.*, 20:709-760 (2002).
Padilla et al., "A Y639F/H784A T7 RNA polymerase double mutant displays superior properties for synthesizing RNAs with non-canonical NTPs", *Nuc. Acids Res.*, 30(24):e138 (2002).
Padilla et al., "Efficient synthesis of nucleic acids heavily modified with non-canonical ribose 2′-groups using a mutant T7 RNA polymerase (RNAP)", *Nuc. Acids Res.*, 27(6):1561-1563 (1999).
Pietersz et al., "A 16-mer peptide (RQIKIWFQNRRMKWKK) from antennapedia preferentially targets the Class I pathway", *Vaccine*, 19:1397-1405 (2001).
Rothbard et al., "Arginine-Rich Molecular Transporters for Drug Delivery: Role of Backbone Spacing in Cellular Uptake", *J. Med. Chem.*, 45(17):3612-3618 (2002).

(Continued)

*Primary Examiner* — Richard Hutson
(74) *Attorney, Agent, or Firm* — Mintz Levin Cohn Ferris Glovsky and Popeo, P.C.; Ivor R. Elrifi

(57) ABSTRACT

Materials and methods are provided for producing aptamer therapeutics having fully modified nucleotide triphosphates incorporated into their sequence.

11 Claims, 15 Drawing Sheets

OTHER PUBLICATIONS

Rothbard et al., "Conjugation of arginine oligomers to cyclosporine A facilitates topical delivery and inhibition of inflammation", *Nat. Med.*, 6(11):1253-1257 (2000).

Ruckman et al., "2'-Fluoropyrimidine RNA-based Aptamers to the 165-Amino Acid Form of Vascular Endothelial Growth Factor (VEGF$_{165}$)", *J. Biol. Chem.*, 273(32):20556-20567 (1998).

Sood et al., "A rapid and convenient synthesis of poly-thymidylic acid by the modified trimester approach", *Nuc. Acids Res.*, 4(8):2757-2765 (1977).

Sproat et al., "New synthetic routes to synthons suitable for 2'-O'allyloligoribonucleotide assembly", *Nuc. Acids Res.*, 19(4):733-738 (1990).

Tucker et al., "Detection and plasma pharmacokinetics of an anti-vascular endothelial growth factor oligonucleotide-aptamer (NX1838) in rhesus monkeys", *J. Chromatograph. B.*, 732:203-212 (1999).

Vives et al., "A Truncated HIV-1 Tat Protein Basic Domain Rapidly Translocates through the Plasma Membrane and Accumulates in the Cell Nucleus", *J. Biol. Chem.*, 272(25):16010-16017 (1997).

Brieba et al., "Roles of Histidine 784 and Tyrosine 639 in Ribose Discrimination by T7 RNA Polymerase", *Biochemistry*, 39:919-923 (2000).

Burmeister, et al., "2-Deoxy Purine, 2'O-Methyl Pyrimidine (dRmY) Aptamers as Candidate Therapeutics", *Oligonucleotides*, 16(4):337-351 (2006).

Henry et al., "The evolution of DNA polymerases with novel activities," Current Opinion in Biotechnology, vol. 16(4): 370-77 (2005).

Ito et al., "In vitro selection of RNA aptamers carrying multiple biotin groups in the side chains," Bioconjugate Chemistry, vol. 12(6): 850-54 (2001).

\* cited by examiner

Figure 4

| Template | ARC2117 | ARC2118 | ARC2119 | ARC2120 | ARC2121 |
|---|---|---|---|---|---|
| Relative mRmY transcript yield* with FAR Polymerase | <10 | <10 | <10 | <10 | <10 |
| Relative mRmY transcript yield* with LAR Polymerase | 30 | 100 | 80 | 20 | <10 |

Figure 5A atgaacacgattaacatcgctaagaacgacttctctgacatcgaactggctgctatcccgttcaacactctggctgaccattacggtgagcgtttagctcgcgaacagttgg
cccttgagcatgagtcttacgagatgggtgaagcacgcttccgcaagatgtttgagcgtcaacttaaagctggtgaggttgccggataacgctgccgccaagcctctcatca
ctaccctactccctaagatgattgcacgcatcaacgactggtttgaggaagtgaaagctaagcgcggcaagcgcccgacagccttccagttcctgcaagaaatcaagcc
ggaagccgtagcgtacatcaccattaagaccactctggcttgcctaaccagtgctgacaatacaaccgttcaggctgtagcaagcgcaatcggtcgggccattgaggac
gaggctcgcttcggtcgtatccgtgaccttgaagctaagcacttcaagaaaaacgttgaggaacaactcaacaagcgcgtagggcacgtctacaagaaagcatttatgca
agttgtcgaggctgacatgctctctaagggtctactcggtggcgaggcgtggtcttcgtggcataaggaagactctattcatgtaggagtacgctgcatcgagatgctcatt
gagtcaaccggaatggttagcttacaccgccaaaatgctggcgtagtaggtcaagactctgagactatcgaactcgcacctgaatacgctgaggctatcgcaacccgtgc
aggtgcgctggctggcatctctccgatgttccaaccttgcgtagttcctcctaagccgtggactggcattactggtggtggctattgggctaacggtcgtcgtcctctggcg
ctggtgcgtactcacagtaagaaagcactgatgcgctacgaagacgtttacatgcctgaggtgtacaaagcgattaacattgcgcaaaacaccgcatggaaaatcaacaa
gaaagtcctagcggtcgccaacgtaatcaccaagtggaagcattgtccggtcgaggacatccctgcgattgagcgtgaagaactcccgatgaaaccggaagacatcga
catgaatcctgaggctctcaccgcgtggaaacgtgctgccgctgctgtgtaccgcaaggacaaggctcgcaagtctcgccgtatcagccttgagttcatgcttgagcaag
ccaataagtttgctaaccataaggccatctggttcccttacaacatggactggcgcggtcgtgtttacgctgtgtcaatgttcaacccgcaaggtaacgatatgaccaaagg
actgcttacgctggcgaaaggtaaaccaatcggtaaggaaggttactactggctgaaaatccacggtgcaaactgtgcgggtgtcgataaggttccgttccctgagcgca
tcaagttcattgaggaaaaccacgagaacatcatggcttgcgctaagtctccactggagaacacttggtgggctgagcaagattctccgttctgcttccttgcgttctgctttg
agtacgctggggtacagcaccacggcctgagctataactgctcccttccgctggcgtttgacgggtcttgctctggcatccagcacttctccgcgatgctccgagatgagg
taggtggtcgcgcggttaacttgcttcctagtgaaaccgttcaggacatctacgggattgttgctaagaaagtcaacgagattctacaagcagacgcaatcaatgggaccg
ataacgaagtagttaccgtgaccgatgagaacactggtgaaatctctgagaaagtcaagctgggcactaaggcactggctggtcaatggctggcttacggtgttactcgc
agtgtgactaagcgttcagtcatgacgctggcttacgggtccaaagagttcggcttccgtcaacaagtgctggaagataccattcagccagctattgattccggcaagggt
ctgatgttcactcagccgaatcaggctgctggatacatggctaagctgatttgggaatctgtgagcgtgacggtggtagctgcggttgaagcaatgaactggcttaagtctg
ctgctaagctgctggctgctgaggtcaaagataagaagactggagagattcttcgcaagcgttgcgctgtgcattgggtaactcctgatggtttccctgtgtggcaggaata
caagaagcctattcagacgcgcttgaacctgatgttcctccggtcagttccgcttacagcctaccattaacaccaacaaagatagcgagattgatgcacacaaacaggagtc
tggtatcgctcctaactttgtacacagccaagacggtagccaccttcgtaagactgtagtgtgggcacacgagaagtacggaatcgaatcttttgcactgattcacgactcc
ttcggtaccattccggctgacgctgcgaacctgttcaaagcagtgcgcgaaactatggttgacacatatgagtcttgtgatgtactggctgattctacgaccagttcgctga
ccagttgcacgagtctcaattggacaaaatgccagcacttccggctaaaggtaacttgaacctccgtgacatcttagagtcggacttcgcgttcgcgtaa (SEQ ID NO 120)

Figure 5B

MNTINIAKNDFSDIELAAIPFNTLADHYGERLAREQLALEHESYEMGEARFRKMFERQLKAGEVADNAAAKPLI
TTLLPKMIARINDWFEEVKAKRGKRPTAFQFLQEIKPEAVAYITIKTTLACLTSADNTTVQAVASAIGRAIEDEA
RFGRIRDLEAKHFKKNVEEQLNKRVGHVYKKAFMQVVEADMLSKGLLGGEAWSSWHKEDSIHVGVRCIEMLI
ESTGMVSLHRQNAGVVGQDSETIELAPEYAEAIATRAGALAGISPMFQPCVVPPKPWTGITGGGYWANGRRPL
ALVRTHSKKALMRYEDVYMPEVYKAINIAQNTAWKINKKVLAVANVITKWKHCPVEDIPAIEREELPMKPEDI
DMNPEALTAWKRAAAAVYRKDKARKSRRISLEFMLEQANKFANHKAIWFPYNMDWRGRVYAVSMFNPQGN
DMTKGLLTLAKGKPIGKEGYYWLKIHGANCAGVDKVPFPERIKFIEENHENIMACAKSPLENTWWAEQDSPFC
FLAFCFEYAGVQHHGLSYNCSLPLAFDGSCSGIQHFSAMLRDEVGGRAVNLLPSETVQDIYGIVAKKVNEILQA
DAINGTDNEVVTVTDENTGEISEKVKLGTKALAGQWLAYGVTRSVTKRSVMTLAYGSKEFGFRQQVLEDTIQP
AIDSGKGLMFTQPNQAAGYMAKLIWESVSVTVVAAVEAMNWLKSAAKLLAAEVKDKKTGEILRKRCAVHW
VTPDGFPVWQEYKKPIQTRLNLMFLGQFRLQPTINTNKDSEIDAHKQESGIAPNFVHSQDGSHLRKTVVWAHE
KYGIESFALIHDSFGTIPADAANLFKAVRETMVDTYESCDVLADFYDQFADQLHESQLDKMPALPAKGNLNLR
DILESDFAFA (SEQ ID NO 121)

Figure 6A atgaacacgattaacatcgctaagaacgacttctctgacatcgaactggctgctatcccgttcaacactctggctgaccattacggtgagcgtttagctcgcgaacagttgg
cccttgagcatgagtcttacgagatgggtgaagcacgcttccgcaagatgtttgagcgtcaacttaaagctggtgaggttgcggataacgctgccgccaagcctctcatca
ctaccctactccctaagatgattgcacgcatcaacgactggtttgaggaagtgaaagctaagcgcggcaagcgcccgacagccttccagttcctgcaagaaatcaagcc
ggaagccgtagcgtacatcaccattaagaccactctggcttgcctaaccagtgctgacaatacaaccgttcaggctgtagcaagcgcaatcggtcgggccattgaggac
gaggctcgcttcggtcgtatccgtgaccttgaagctaagcacttcaagaaaaacgttgaggaacaactcaacaagcgcgtagggcacgtctacaagaaagcatttatgca
agttgtcgaggctgacatgctctctaagggtctactcggtggcgaggcgtggtcttcgtggcataaggaagactctattcatgtaggagtacgctgcatcgagatgctcatt
gagtcaaccggaatggttagcttacaccgccaaaatgctggcgtagtaggtcaagactctgagactatcgaactcgcacctgaatacgctgaggctatcgcaacccgtgc
aggtgcgctggctggcatctctccgatgttccaaccttgcgtagttcctcctaagccgtggactggcattactggtggtggctattgggctaacggtcgtcgtcctctggcg
ctggtgcgtactcacagtaagaaagcactgatgcgctacgaagacgtttacatgcctgaggtgtacaaagcgattaacattgcgcaaaacaccgcatggaaaatcaacaa
gaaagtcctagcggtcgccaacgtaatcaccaagtggaagcattgtccggtcgaggacatccctgcgattgagcgtgaagaactcccgatgaaaccggaagacatcga
catgaatcctgaggctctcaccgcgtggaaacgtgctgccgctgctgtgtaccgcaaggacaaggctcgcaagtctcgccgtatcagccttgagttcatgcttgagcaag
ccaataagtttgctaaccataaggccatctggttcccttacaacatggactggcgcggtcgtgtttacgctgtgtcaatgttcaacccgcaaggtaacgatatgaccaaagg
actgcttacgctggcgaaaggtaaaccaatcggtaaggaaggttactactggctgaaaatccacggtgcaaactgtgcgggtgtcgataaggttccgttccctgagcgca
tcaagttcattgaggaaaaccacgagaacatcatggcttgcgctaagtctccactggagaacacttggtgggctgagcaagattctccgttctgcttccttgcgttctgctttg
agtacgctggggtacagcaccacggcctgagctataactgctcccttccgctggcgtttgacgggtcttgctctggcatccagcacttctccgcgatgctccgagatgagg
taggtggtcgcgcggttaacttgcttcctagtgaaaccgttcaggacatctacgggattgttgctaagaaagtcaacgagattctacaagcagacgcaatcaatgggaccg
ataacgaagtagttaccgtgaccgatgagaacactggtgaaatctctgagaaagtcaagctgggcactaaggcactggctggtcaatggctggcttacggtgttactcgc
agtgtgactaagcgttcagtcatgacgctggctCTGgggtccaaagagttcggcttccgtcaacaagtgctggaagataccattcagccagctattgattccggcaagg
gtctgatgttcactcagccgaatcaggctgctggatacatggctaagctgatttgggaatctgtgagcgtgacggtggtagctgcggttgaagcaatgaactggcttaagtc
tgctgctaagctgctggctgctgaggtcaaagataagaagactggagagattcttcgcaagcgttgcgctgtgcattgggtaactcctgatggtttccctgtgtggcaggaa
tacaagaagcctattcagacgcgcttgaacctgatgttcctcggtcagttccgcttacagcctaccattaacaccaacaaagatagcgagattgatgcacacaaacaggag
tctggtatcgctcctaactttgtaGCcagccaagacggtagccaccttcgtaagactgtagtgtgggcacacgagaagtacggaatcgaatcttttgcactgattcacgac
tccttcggtaccattccggctgacgctgcgaacctgttcaaagcagtgcgcgaaactatggttgacacatatgagtcttgtgatgtactggctgatttctacgaccagttcgct
gaccagttgcacgagtctcaattggacaaaatgccagcacttccggctaaaggtaacttgaacctccgtgacatcttagagtcggacttcgcgttcgcgtaa
(SEQ ID NO 122)

Figure 6B

```
   1 atgaacacga ttaacatcgc taagaacgac ttctctgaca tcgaactggc tgctatcccg
  61 ttcaacactc tggctgacca ttacggtgag cgtttagctc gcgaacagtt ggcccttgag
 121 catgagtctt acgagatggg tgaagcacgc ttccgcaaga tgtttgagcg tcaacttaaa
 181 gctggtgagg ttgcggataa cgctgccgcc aagcctctca tcactaccct actccctaag
 241 atgattgcac gcatcaacga ctggtttgag gaagtgaaag ctaagcgcgg caagcgcccg
 301 acagccttcc agttcctgca agaaatcaag ccggaagccg tagcgtacat caccattaag
 361 accactctgg cttgcctaac cagtgctgac aatacaaccg ttcaggctgt agcaagcgca
 421 atcggtcggg ccattgagga cgaggctcgc ttcggtcgta tccgtgacct tgaagctaag
 481 cacttcaaga aaaacgttga ggaacaactc aacaagcgcg tagggcacgt ctacaagaaa
 541 gcatttatgc aagttgtcga ggctgacatg ctctctaagg gtctactcgg tggcgaggcg
 601 tggtcttcgt ggcataagga agactctatt catgtaggag tacgctgcat cgagatgctc
 661 attgagtcaa ccggaatggt tagcttacac cgccaaaatg ctggcgtagt aggtcaagac
 721 tctgagacta tcgaactcgc acctgaatac gctgaggcta tcgcaacccc tgcaggtgcg
 781 ctggctggca tctctccgat gttccaacct tgcgtagttc ctcctaagcc gtggactggc
 841 attactggtg gtggctattg ggctaacggt cgtcgtcctc tggcgctggt gcgtactcac
 901 agtaagaaag cactgatgcg ctacgaagac gtttacatgc ctgaggtgta caaagcgatt
 961 aacattgcgc aaaacaccgc atggaaaatc aacaagaaag tcctagcggt cgccaacgta
1021 atcaccaagt ggaagcattg tccggtcgag gacatccctg cgattgagcg tgaagaactc
1081 ccgatgaaac cggaagacat cgacatgaat cctgaggctc tcaccgcgtg gaGacgtgct
1141 gccgctgctg tgtaccgcaa ggacaaggct cgcaagtctc gccgtatcag ccttgagttc
1201 atgcttgagc aagccaataa gtttgctaac cataaggcca tctggttccc ttacaacatg
1261 gactggcgcg gtcgtgttta cgctgtgtca atgttcaacc cgcaaggtaa cgatatgacc
1321 aaaggactgc ttacgctggc gaaaggtaaa ccaatcggta aggaaggtta ctactggctg
1381 aaaatccacg gtgcaaactg tgcgggtgtc gataaggttc cgttccctga gcgcatcaag
1441 ttcattgagg aaaaccacga gaacatcatg gcttgcgcta agtctccact ggagaacact
1501 tggtgggctg agcaagattc tccgttctgc ttccttgcgt tctgctttga gtacgctggg
1561 gtacagcacc acggcctgag ctataactgc tcccttccgc tggcgtttga cgggtcttgc
1621 tctggcatcc agcacttctc cgcgatgctc cgagatgagg taggtggtcg cgcggttaac
1681 ttgcttccta gtgaaaccgt tcaggacatc tacgggattg ttgctaagaa agtcaacgag
1741 attctacaag cagacgcaat caatgggacc gataacgaag tagttaccgt gaccgatgag
1801 aacactggtg aaatctctga gaaagtcaag ctgggcacta aggcactggc tggtcaatgg
1861 ctggcttacg gtgttactcg cagtgtgact aagcgttcag tcatgacgct ggctCTGggg
1921 tccaaagagt tcggcttccg tcaacaagtg ctggaagata ccattcagcc agctattgat
1981 tccggcaagg gtctgatgtt cactcagccg aatcaggctg ctggatacat ggctaagctg
2041 atttgggaat ctgtgagcgt gacggtggta gctgcggttg aagcaatgaa ctggcttaag
2101 tctgctgcta agctgctggc tgctgaggtc aaagataaga agactggaga gattcttcgc
2161 aagcgttgcg ctgtgcattg ggtaactcct gatggtttcc ctgtgtggca ggaatacaag
2221 aagcctattc agacgcgctt gaacctgatg ttcctcggtc agttccgctt acagcctacc
2281 attaacacca caaagatag cgagattgat gcacacaaac aggagtctgg tatcgctcct
2341 aactttgtaG Ccagccaaga cggtagccac cttcgtaaga ctgtagtgtg ggcacacgag
2401 aagtacggaa tcgaatcttt tgcactgatt cacgactcct tcggtaccat tccggctgac
2461 gctgcgaacc tgttcaaagc agtgcgcgaa actatggttg acacatatga gtcttgtgat
2521 gtactggctg atttctacga ccagttcgct gaccagttgc acagtctca attggacaaa
2581 atgccagcac ttccggctaa aggtaacttg aacctccgtg acatcttaga gtcggacttc
2641 gcgttcgcgt aa (SEQ ID NO123)
```

Figure 6C atgaacacgattaacatcgctaagaacgacttctctgacatcgaactggctgctatcccgttcaacactctggctgaccattacggtgagcgtttagctcgcgaacagttggcccttgagcatgagtcttacgagatgggtgaagcacgcttccgcaagatgtttgagcgtcaacttaaagctggtgaggttgcggataacgctgccgccaagcctctcatcactaccctatccctaagatgattgcacgcatcaacgactggtttgaggaagtgaaagctaagcgcggcaagcgcccgacagccttccagttcctgcaagaaatcaagccggaagccgtagcgtacatcaccattaagaccactctggcttgcctaaccagtgctgacaatacaaccgttcaggctgtagcaagcgcaatcggtcgggccattgaggacgaggctcgcttcggtcgtatccgtgaccttgaagctaagcacttcaagaaaaacgttgaggaacaactcaacaagcgcgtagggcacgtctacaagaaagcatttatgcaagttgtcgaggctgacatgctctctaagggtctactcggtggcgaggcgtggtcttcgtggcataaggaagactctattcatgtaggagtacgctgcatcgagatgctcattgagtcaaccggaatggttagcttacaccgccaaaatgctggcgtagtaggtcaagactctgagactatcgaactcgcacctgaatacgctgaggctatcgcaacccgtgcaggtgcgctggctggcatctctcTgatgttccaaccttgcgtagttcctcctaagccgtggactggcattactggtggtggctattgggctaacggtcgtcgtcctctggcgctggtgcgtactcacagtaagaaagcactgatgcgctacgaagacgtttacatgcctgaggtgtacaaagcgattaacattgcgcaaaacaccgcatggaaaatcaacaagaaagtcctagcggtcgccaacgtaatcaccaagtggaagcattgtccggtcgaggacatccctgcgattgagcgtgaagaactcccgatgaaaccggaagacatcgacatgaatcctgaggctctcaccgcgtggaaacgtgctgccgctgctgtgtaccgcaaggacaaggctcgcaagtctcgccgtatcagccttgagttcatgcttgagcaagccaataagtttgctaaccataaggccatctggttccctttacaacatggactggcgcggtcgtgtttacgctgtgtcaatgttcaacccgcaaggtaacgatatgaccaaaggactgcttacgctggcgaaaggtaaaccaatcggtaaggaaggttactactggctgaaaatccacggtgcaaactgtgcgggtgtcgataaggttccgttccctgagcgcatcaagttcattgaggaaaaccacgagaacatcatggcttgcgctaagtctccactggagaacacttggtgggctgagcaagattctccgttctgcttccttgcgttctgctttgagtacgctggggtacagcaccacggcctgagctataactgctcccttccgctggcgtttgacgggtcttgctctggcatccagcacttctccgcgatgctccgagatgaggtaggtggtcgcgcggttaacttgcttcctagtgaaaccgttcaggacatctacgggattgttgctaagaaagtcaacgagattctacaagcagacgcaatcaatgggaccgataacgaagtagttaccgtgaccgatgagaacactggtgaaatctctgagaaagtcaagctgggcactaaggcactggctggtcaatggctggcttacggtgttactcgcagtgtgactaagcgttcagtcatgacgctggctCTGgggtccaaagagttcggcttccgtcaacaagtgctggaagataccattcagccagctattgattccggcaagggtctgatgttcactcagccgaatcaggctgctggatacatggctaagctgatttgggaatctgtgagcgtgacggtggtagctgcggttgaagcaatgaactggcttaagtctgctgctaagctgctggctgctgaggtcaaagataagaagactggagagattcttcgcaagcgttgcgctgtgcattgggtaactcctgatggtttccctgtgtggcaggaatacaagaagcctattcagacgcgcttgaacctgatgttcctcggtcagttccgcttacagcctaccattaacaccaacaaagatagcgagattgatgcacacaaacaggagtctggtatcgctcctaactttgtaGCcagccaagacggtagccaccttcgtaagactgtagtgtgggcacacgagaagtacggaatcgaatcttttgcactgattcacgactccttcggtaccattccggctgacgctgcgaacctgttcaaagcagtgcgcgaaactatggttgacacatatgagtcttgtgatgtactggctgatttctacgaccagttcgctgaccagttgcacgagtctcaattggacaaaatgccagcacttccggctaaaggtaacttgaacctccgtgacatcttagagtcggacttcgcgttcgcgtaa (SEQ ID NO 124)

Figure 6D atgaacacgattaacatcgctaagaacgacttctctgacatcgaactggctgctatcccgttcaacactctggctgaccattacggtgagcgtttagctcgcgaacagttggcccttgagcatgagtcttacgagatgggtgaagcacgcttccgcaagatgtttgagcgtcaacttaaagctggtgaggttgcggataacgctgccgccaagcctctcatcactaccctactcctaagatgattgcacgcatcaacgactggtttgaggaagtgaaagctaagcgcggcaagcgcccgacagccttccagttcctgcaagaaatcaagccggaagccgtagcgtacatcaccattaagaccactctggcttgcctaaccagtgctgacaatacaaccgttcaggctgtagcaagcgcaatcggtcgggccattgaggacgaggctcgcttcggtcgtatccgtgaccttgaagctaagcacttcaagaaaaacgttgaggaacaactcaacaagcgcgtagggcacgtctacaagaaagcatttatgcaagttgtcgaggctgacatgctctctaagggtctactcggtggcgaggcgtggtcttcgtggcataaggaagactctattcatgtaggagtacgctgcatcgagatgctcattgagtcaaccggaatggttagcttacaccgccaaaatgctggcgtagtaggtcaagactctgagactatcgaactcgcacctgaatacgctgaggctatcgcaacccgtgcaggtgcgctggctggcatctctcTgatgttccaaccttgcgtagttcctcctaagccgtggactggcattactggtggtggctattgggctaacggtcgtcgtcctctggcgctggtgcgtactcacagtaagaaagcactgatgcgctacgaagacgtttacatgcctgaggtgtacaaagcgattaacattgcgcaaaacaccgcatggaaaatcaacaagaaagtcctagcggtcgccaacgtaatcaccaagtggaagcattgtccggtcgaggacatccctgcgattgagcgtgaagaactcccgatgaaaccggaagacatcgacatgaatcctgaggctctcaccgcgtggaGacgtgctgccgctgctgtgtaccgcaaggacaaggctcgcaagtctcgccgtatcagccttgagttcatgcttgagcaagccaataagtttgctaaccataaggccatctggttccctttacaacatggactggcgcggtcgtgtttacgctgtgtcaatgttcaacccgcaaggtaacgatatgaccaaaggactgcttacgctggcgaaaggtaaaccaatcggtaaggaaggttactactggctgaaaatccacggtgcaaactgtgcgggtgtcgataaggttccgttccctgagcgcatcaagttcattgaggaaaaccacgagaacatcatggcttgcgctaagtctccactggagaacacttggtgggctgagcaagattctccgttctgcttccttgcgttctgctttgagtacgctggggtacagcaccacggcctgagctataactgctcccttccgctggcgtttgacgggtcttgctctggcatccagcacttctccgcgatgctccgagatgaggtaggtggtcgcgcggttaacttgcttcctagtgaaaccgttcaggacatctacgggattgttgctaagaaagtcaacgagattctacaagcagacgcaatcaatgggaccgataacgaagtagttaccgtgaccgatgagaacactggtgaaatctctgagaaagtcaagctgggcactaaggcactggctggtcaatggctggcttacggtgttactcgcagtgtgactaagcgttcagtcatgacgctggctCTGgggtccaaagagttcggcttccgtcaacaagtgctggaagataccattcagccagctattgattccggcaagggtctgatgttcactcagccgaatcaggctgctggatacatggctaagctgatttgggaatctgtgagcgtgacggtggtagctgcggttgaagcaatgaactggcttaagtctgctgctaagctgctggctgctgaggtcaaagataagaagactggagagattcttcgcaagcgttgcgctgtgcattgggtaactcctgatggtttccctgtgtggcaggaatacaagaagcctattcagacgcgcttgaacctgatgttcctcggtcagttccgcttacagcctaccattaacaccaacaaagatagcgagattgatgcacacaaacaggagtctggtatcgctcctaactttgtaGCcagccaagacggtagccaccttcgtaagactgtagtgtgggcacacgagaagtacggaatcgaatcttttgcactgattcacgactccttcggtaccattccggctgacgctgcgaacctgttcaaagcagtgcgcgaaactatggttgacacatatgagtcttgtgatgtactggctgatttctacgaccagttcgctgaccagttgcacgagtctcaattggacaaaatgccagcacttccggctaaaggtaacttgaacctccgtgacatcttagagtcggacttcgcgttcgcgtaa (SEQ ID NO 125)

Figure 7

| Relative Transcript Yields* | ARC2118 | ARC2119 |
|---|---|---|
| [rGTP]   0uM | 40 | 49 |
| [rGTP]   5uM | 74 | 62 |
| [rGTP]   10uM | 94 | 21 |
| [rGTP]   20uM | 100 | 30 |
| [rGTP]   40uM | 95 | 36 |
| [rGTP]   80uM | 93 | 41 |
| [rGTP]   160uM | 95 | 32 |

Figure 8

| Transcription component Concentration | Transcription Conditions 1 | Tanscription Conditions 2 | Transcription Conditions 3 | Transcription Conditions 4 |
|---|---|---|---|---|
| [MgCl2] | 5mM | 6.5mM | 8mM | 9.5mM |
| [MnCl2] | 1.5mM | 2mM | 2.5mM | 3mM |
| [2'-OMe NTP] (each) | 0.5mM | 1mM | 1.5mM | 2mM |
| Relative Yield | 0.8 | 1.0 | 1.5 | 1.6 |

Figure 9

|  | Deletions | Insertions | Substitutions | Perfect N30 | N |
|---|---|---|---|---|---|
| 2'-OH RNA[1] | 0.7% | 0.0% | 0.3% | 74% | 1936 |
| 2'-OMe RNA[1] | 0.6% | 0.6% | 1.2% | 49% | 1584 |
| 2'-OMe RNA[2] | 0.0% | 0.0% | 0.23% | 93% | 1300 |

Figure 10

|  | Total | A | G | C | T | N |
|---|---|---|---|---|---|---|
| Starting library | 1206 | 21.9 % | 28.3 % | 24.1 % | 25.0 % | 0.66% |
| library after Transcription | 1386 | 25% | 25.3 % | 21.5 % | 28.1 % | 0.0 % |

Figure 13
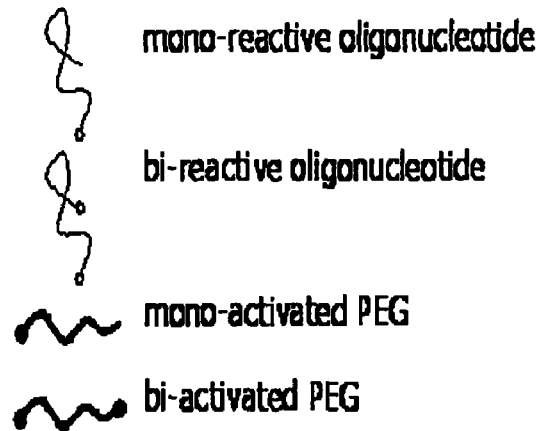
standard PEGylation
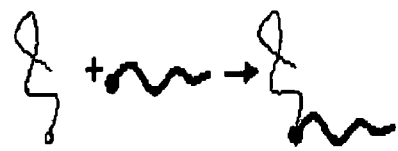
multiple PEGylation
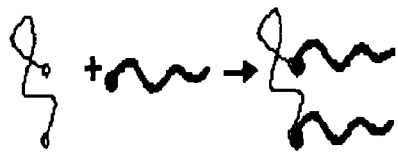
dimerization via PEGylation
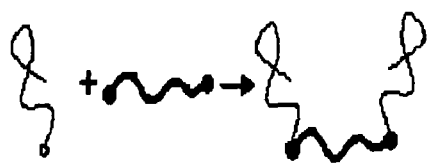

MATERIALS AND METHODS FOR THE GENERATION OF FULLY 2'-MODIFIED NUCLEIC ACID TRANSCRIPTS

REFERENCE TO RELATED APPLICATIONS

This non-provisional patent application claims priority under 35 U.S.C. §119(e) to the following provisional application: U.S. Provisional Patent Application Ser. No. 60/696,292 filed on Jun. 30, 2005 which is herein incorporated by reference in its entirety. The invention relates generally to the field of nucleic acids and more particularly to aptamers.

FIELD OF INVENTION

The invention relates to materials and methods for transcribing nucleic acids, particularly modified enzymes and materials and methods for using the modified enzymes in template directed polymerization to increase the incorporation of modified nucleotides into nucleic acids, particularly aptamers. Additionally, the invention relates to methods and materials for selecting transcription template component sequences and the use of such component sequences in enhancing transcript yield, particularly in enhancing transcript yield during the SELEX™ method.

BACKGROUND OF THE INVENTION

An aptamer by definition is an isolated nucleic acid molecule which binds with high specificity and affinity to some target such as a protein through interactions other than Watson-Crick base pairing. Although aptamers are nucleic acid based molecules, there is a fundamental difference between aptamers and other nucleic acid molecules such as genes and mRNA. In the latter, the nucleic acid structure encodes information through its linear base sequence and thus this sequence is of importance to the function of information storage. In complete contrast, aptamer function, which is based upon the specific binding of a target molecule, is not dependent on a conserved linear base sequence, but rather a particular secondary/tertiary structure. That is, aptamers are non-coding sequences. Any coding potential that an aptamer may possess is entirely fortuitous and plays no role whatsoever in the binding of an aptamer to its cognate target. Thus, while it may be that aptamers that bind to the same target, and even to the same site on that target, share a similar linear base sequence, most do not.

Aptamers must also be differentiated from the naturally occurring nucleic acid sequences that bind to certain proteins. These latter sequences are naturally occurring sequences embedded within the genome of the organism that bind to a specialized sub-group of proteins that are involved in the transcription, translation and transportation of naturally occurring nucleic acids, i.e., nucleic acid binding proteins. Aptamers on the other hand are short, isolated, non-naturally occurring nucleic acid molecules. While aptamers can be identified that bind nucleic acid binding proteins, in most cases such aptamers have little or no sequence identity to the sequences recognized by the nucleic acid binding proteins in nature. More importantly, aptamers can bind virtually any protein (not just nucleic acid binding proteins) as well as almost any target of interest including small molecules, carbohydrates, peptides, etc. For most targets, even proteins, a naturally occurring nucleic acid sequence to which it binds does not exist. For those targets that do have such a sequence, i.e., nucleic acid binding proteins, such sequences will differ from aptamers as a result of the relatively low binding affinity used in nature as compared to tightly binding aptamers.

Aptamers, like peptides generated by phage display or antibodies, are capable of specifically binding to selected targets and modulating the target's activity or binding interactions, e.g., through binding aptamers may block their target's ability to function. As with antibodies, this functional property of specific binding to a target is an inherent property. Also as with antibodies, although the skilled person may not know what precise structural characteristics an aptamer to a target will have, the skilled person knows how to identify, make and use such a molecule in the absence of a precise structural definition.

Aptamers also are analogous to small molecule therapeutics in that a single structural change, however seemingly minor, can dramatically effect (by several orders of magnitude) the binding and/or other activity (or activities) of the aptamer. On the other hand, some structural changes will have little or no effect whatsoever. This results from the importance of the secondary/tertiary structure of aptamers. In other words, an aptamer is a three dimensional structure held in a fixed conformation that provides chemical contacts to specifically bind its given target. Consequently: (1) some areas or particular sequences are essential as (a) specific points of contact with target, and/or as (b) sequences that position the molecules in contact with the target; (2) some areas or particular sequences have a range of variability, e.g., nucleotide X must be a pyrimidine, or nucleotide Y must be a purine, or nucleotides X and Y must be complementary; and (3) some areas or particular sequences can be anything, i.e., they are essentially spacing elements, e.g., they could be any string of nucleotides of a given length or even an non-nucleotide spacer such as a PEG molecule.

Discovered by an in vitro selection process from pools of random sequence oligonucleotides, aptamers have been generated for over 130 proteins including growth factors, transcription factors, enzymes, immunoglobulins, and receptors. A typical aptamer is 10-15 kDa in size (20-45 nucleotides), binds its target with nanomolar to sub-nanomolar affinity, and discriminates against closely related targets (e.g., aptamers will typically not bind other proteins from the same gene family). A series of structural studies have shown that aptamers are capable of using the same types of binding interactions (e.g., hydrogen bonding, electrostatic complementarities, hydrophobic contacts, steric exclusion) that drive affinity and specificity in antibody-antigen complexes.

Aptamers have a number of desirable characteristics for use as therapeutics and diagnostics including high specificity and affinity, biological efficacy, and excellent pharmacokinetic properties. In addition, they offer specific competitive advantages over antibodies and other protein biologics, for example:

1) Speed and control. Aptamers are produced by an entirely in vitro process, allowing for the rapid generation of initial leads, including therapeutic leads. In vitro selection allows the specificity and affinity of the aptamer to be tightly controlled and allows the generation of leads, including leads against both toxic and non-immunogenic targets.

2) Toxicity and Immunogenicity. Aptamers as a class have demonstrated therapeutically acceptable toxicity or lack of immunogenicity. Whereas the efficacy of many monoclonal antibodies can be severely limited by immune response to antibodies themselves, it is extremely difficult to elicit antibodies to aptamers most likely because aptamers cannot be presented by T-cells via the MHC and the immune response is generally trained not to recognize nucleic acid fragments.

3) Administration. Whereas most currently approved antibody therapeutics are administered by intravenous infusion (typically over 2-4 hours), aptamers can be administered by subcutaneous injection (aptamer bioavailability via subcutaneous administration is >80% in monkey studies (Tucker et al., J. Chromatography B. 732: 203-212, 1999)). This difference is primarily due to the comparatively low solubility and thus large volumes necessary for most therapeutic mAbs. With good solubility (>150 mg/mL) and comparatively low molecular weight (aptamer: 10-50 kDa; antibody: 150 kDa), a weekly dose of aptamer may be delivered by injection in a volume of less than 0.5 mL. In addition, the small size of aptamers allows them to penetrate into areas of conformational constrictions that do not allow for antibodies or antibody fragments to penetrate, presenting yet another advantage of aptamer-based therapeutics or prophylaxis.

4) Scalability and cost. Therapeutic aptamers are chemically synthesized and consequently can be readily scaled as needed to meet production demand. Whereas difficulties in scaling production are currently limiting the availability of some biologics and the capital cost of a large-scale protein production plant is enormous, a single large-scale oligonucleotide synthesizer can produce upwards of 100 kg/year and requires a relatively modest initial investment. The current cost of goods for aptamer synthesis at the kilogram scale is estimated at $500/g, comparable to that for highly optimized antibodies. Continuing improvements in process development are expected to lower the cost of goods to <$100/g in five years.

5) Stability. Therapeutic aptamers are chemically robust. They are intrinsically adapted to regain activity following exposure to factors such as heat and denaturants and can be stored for extended periods (>1 yr) at room temperature as lyophilized powders. In contrast, antibodies must be stored refrigerated.

In addition to the intrinsic stability of aptamers, modified nucleotides (e.g., 2'-modified nucleotides) which are inexpensive, non-toxic, and which can increase resistance to enzymatic, chemical, thermal, and physical degradation, can be incorporated during SELEX™ method as described in U.S. patent application Ser. No. 10/729,851 filed Dec. 3, 2002, and U.S. patent application Ser. No. 10/873,856, filed Jun. 21, 2004. While incorporation of modified nucleotides during SELEX™ process is oftentimes preferable to post-SELEX™ modification due to potential loss of binding affinity and activity that can occur post-SELEX™ selection, the incorporation of modified nucleotides, e.g. 2'-O-methyl nucleotides ("2-OMe"), during the SELEX™ process has been historically difficult because of low transcription yields. Solution conditions and transcription mixtures are described in U.S. patent application Ser. No. 10/729,851 filed Dec. 3, 2002, and U.S. patent application U.S. Ser. No. 10/873,856, filed Jun. 21, 2004, which give improved transcription yields for aptamers incorporating 2'-OMe nucleotides. However transcription yields for fully 2'-O-methylated aptamers remain problematic.

In addition to the advantages of aptamers as therapeutic agent, given the inexpensive nature, low toxicity, and increased nuclease resistance conferred by the incorporation of 2'-OMe nucleotides in aptamers, it would be beneficial to have materials and methods to increase transcript yields of fully 2'-O-methylated aptamers to, e.g., prolong or increase the stability of aptamer therapeutics in vivo. The present invention provides improved materials and methods to meet these and other needs.

SUMMARY OF THE INVENTION

The present relates to T7 RNA polymerases, which may be purified, isolated and/or recombinant. As used herein the term isolated encompasses polymerases of the invention when recombinantly expressed in a cell or tissue. As used herein the term isolated encompasses nucleic acid sequences of the invention when engineered into a cell or tissue In one embodiment, a T7 RNA polymerase comprising an altered amino acid at position 639 and position 784 wherein the altered amino acid at position 639 is not a phenylalanine when the altered amino acid at position 784 is an alanine is provided. In another embodiment, the above described T7 RNA polymerase further comprising an altered amino acid at position 378 is provided. In another embodiment, the above described T7 RNA polymerases further comprising an altered amino acid at position 266 is provided. In a particular embodiment the altered amino acid at position 639 is a leucine and the altered amino acid at position 784 is an alanine. In a further embodiment, the altered amino acid at position 266 is a leucine. In a further embodiment, the altered amino acid at position 378 is an arginine.

In preferred embodiments, the altered amino acids increase the transcriptional yield of nucleic acids comprising 2'-OMe modifications by the polymerase in a transcription reaction comprising only 2'-OMe nucleotide triphosphate. In a particular embodiment the increase in transcription yield is relative to a T7 RNA polymerase lacking the altered amino acids when transcription is carried out for both the altered amino acid T7 RNA polymerase and the T7 RNA polymerase lacking the altered amino acids under identical transcription conditions. In another embodiment, the altered amino acids decrease discrimination against 2'-OMe nucleotide triphosphates. In a particular embodiment, the decreased discrimination against 2'-OMe nucleotide triphosphates is relative to a T7 RNA polymerase lacking the altered amino acids when both polymerases are used under identical transcription conditions. In particular embodiments of this aspect, the T7 RNA polymerase lacking the altered amino acids is the wild type T7 RNA polymerase comprising an amino acid at position 639 altered to a phenylalanine and an amino acid at position 784 altered to alanine or a mutant polymerase having the wild type amino acid sequence except that a phenylalanine has been substituted for the tyrosine at position 639, and an alanine has been substituted for the histidine at position 784 and an arginine residue substituted for the lysine residue at position 378 (Y639F/H784A/K378R).

In a particular embodiment, an isolated polypeptide comprising an amino acid selected from the group consisting of: SEQ ID NO 1, SEQ ID NO 2, SEQ ID NO 102 and SEQ ID NO 103. In a particular embodiment, a kit comprising a container containing a T7 RNA polymerase of the invention is provided.

In some embodiments, a method of transcribing a single stranded nucleic acid comprising incubating a mutant T7 RNA polymerase with a template nucleic acid under reaction conditions sufficient to result in transcription is provided.

In another embodiment, an isolated nucleic acid encoding a polypeptide of the invention is provided. In a particular embodiment a nucleic acid sequence, selected from the group consisting of: SEQ ID NO 122, SEQ ID NO 123, SEQ ID NO 124 and SEQ ID NO 125 is provided. In some embodiments, a vector comprising an isolated nucleic acid sequence of the invention is provided. In a particular embodiment, an expression vector comprising a nucleic acid of the invention operably linked to a promoter is provided. In another embodiment of the invention, a cell comprising the expression vector of the invention is provided. In a particular embodiment, a cell wherein the mutant T7 RNA polymerase of the invention is expressed by the cell is provided. In some embodiments, a kit comprising a container containing a nucleic acid encoding a T7 RNA polymerase of the invention is provided.

In another embodiment, a method of transcribing a fully 2'-OMe nucleic acid comprising the steps of a) incubating a template nucleic acid in a reaction mixture under conditions comprising a mutant RNA polymerase, a nucleic acid transcription template and nucleoside triphosphates, wherein the nucleoside triphosphates are 2'OMe, and b) transcribing the transcription reaction mixture to result in single stranded nucleic acid, wherein all of the nucleotides of the single stranded nucleic acids are 2'-OMe modified except that the first nucleotide of the transcripts can be 2' unmodified, is provided. In some embodiments, the first nucleoside of the transcript may be 2'-OH guanosine. In some embodiments of the method, the mutant RNA polymerase is a mutant T7 RNA polymerase comprising an altered amino acid at position 639 and position 784, particularly a T7 RNA polymerase comprising an altered amino acid at position 639 and position 784 wherein the altered amino acid at position 639 is not a phenylalanine when the altered amino acid at position 784 is an alanine, particularly, a T7 RNA polymerase further comprising an altered amino acid at position 378 and/or an altered amino acid at position 266. In a particular embodiment the altered amino acid at position 639 is a leucine and the altered amino acid at position 784 is an alanine in the polymerase for use in the methods of the invention. In a further embodiment, the altered amino acid at position 266 is a leucine of the polymerase for use in the methods of the invention. In a further embodiment, the altered amino acid at position 378 is an arginine in the polymerase for use in the methods of the invention. In a particular embodiment, an isolated polypeptide comprising an amino acid selected from the group consisting of: SEQ ID NO 1, SEQ ID NO 2, SEQ ID NO 102 and SEQ ID NO 103 is provided.

In some embodiments of the method of the invention, the transcription reaction further comprises magnesium ions. In another embodiment, the transcription reaction further comprises manganese ions. In another embodiment, the magnesium ions are present in the transcription reaction at a concentration that is between 3.0 to 3.5 times greater than the manganese ions. In another embodiment, wherein each nucleotide triphosphate is present in the transcription reaction at a concentration of 1.0 mM, the concentration of magnesium ions is 6.5 mM, and the concentration of manganese ions is 2.0 mM. In another embodiment, wherein each nucleotide triphosphate is present in the transcription reaction at a concentration of 1.5 mM, the concentration of magnesium ions 8 mM, and the concentration of manganese ions is 2.5 mM. In another embodiment, wherein each nucleotide triphosphate is present in the transcription reaction at a concentration of 2.0 mM, the concentration of magnesium ions 9.5 mM and concentration of manganese ions is 3.0 mM.

In another embodiment, the transcription reaction further comprises a non 2'-OMe guanosine non-triphosphate residue, particularly wherein the non 2'-OMe guanosine non-triphosphate residue selected from the group consisting of: guanosine monophosphate, guanosine diphosphate, 2' flouro guanosine monophosphate, 2' flouro guanosine diphosphate, 2'-amino guanosine monophosphate, 2'-amino guanosine diphosphate, 2'-deoxy guanosine monophosphate, and 2'-deoxy guanosine diphosphate. In another embodiment, the transcription template comprises a T7 RNA polymerase promoter. In another embodiment, the transcription reaction further comprises polyethylene glycol. In another embodiment, the transcription reaction comprises inorganic pyrophosphatase.

In another aspect of the invention a method for identifying aptamers is provided. In one embodiment, a method for identifying an aptamer, comprising: a) preparing a transcription reaction mixture comprising a mutant polymerase of the invention, and one or more nucleic acid transcription templates) transcribing the transcription reaction mixture to result in a candidate mixture of single stranded nucleic acids, wherein all but optionally one of the nucleotides of the single stranded nucleic acids are 2'modified, c) contacting the candidate mixture with the target molecule, d) partitioning the nucleic acids having an increased affinity for the target molecule, relative to an affinity of the candidate mixture, from the candidate mixture, and e) amplifying the increased affinity nucleic acids to yield an aptamer enriched mixture, whereby aptamers to the target molecule comprise all 2'-modified nucleotide except that the first nucleotide of the aptamers can be 2'-unmodified are identified, is provided. In some embodiments, the amplifying step f) comprises (i) optionally dissociating the increased affinity nucleic acids from the target, ii) reverse transcribing the increased affinity nucleic acids dissociated from the nucleic acid-target complexes, iii) amplifying the reverse transcribed increased affinity nucleic acids; and (ii) preparing a transcription reaction mixture comprising the amplified reverse transcribed increased affinity nucleic acids as the transcription template and transcribing the transcription mixture.

In some embodiments of the aptamer identification method of the invention, the mutant RNA polymerase is a mutant T7 RNA polymerase comprising an altered amino acid at position 639 and position 784, particularly a T7 RNA polymerase comprising an altered amino acid at position 639 and position 784 wherein the altered amino acid at position 639 is not a phenylalanine when the altered amino acid at position 784 is an alanine, particularly, a T7 RNA polymerase further comprising an altered amino acid at position 378 and/or an altered amino acid at position 266. In a particular embodiment the altered amino acid at position 639 is a leucine and the altered amino acid at position 784 is an alanine in the polymerase for use in the methods of the invention. In a further embodiment, the altered amino acid at position 266 is a leucine of the polymerase for use in the methods of the invention. In a further embodiment, the altered amino acid at position 378 is an arginine in the polymerase for use in the methods of the invention. In a particular embodiment, an isolated polypeptide comprising an amino acid selected from the group consisting of: SEQ ID NO 1, SEQ ID NO 2, SEQ ID NO 102 and SEQ ID NO 103 is used in the aptamer identification method of the invention.

In some embodiments, the all the nucleotide triphosphates in the transcription reaction are 2'-OMe modified. In one embodiment, the one or more nucleic acid transcription template comprises a T7 RNA polymerase promoter and a leader sequence immediately 3' to the T7 RNA polymerase promoter. In some embodiments of this aspect, the method comprises repeating steps a) to e) iteratively.

In some embodiments of the aptamer identifying method of the invention, the transcription reaction further comprises magnesium ions. In another embodiment, the transcription reaction further comprises manganese ions. In another embodiment, the magnesium ions are present in the transcription reaction at a concentration that is between 3.0 to 3.5 times greater than the manganese ions. In another embodiment, wherein each nucleotide triphosphate is present in the transcription reaction at a concentration of 1.0 mM, the concentration of magnesium ions is 6.5 mM, and the concentration of manganese ions is 2.0 mM. In another embodiment, wherein each nucleotide triphosphate is present in the transcription reaction at a concentration of 1.5 mM, the concentration of magnesium ions 8 mM, and the concentration of manganese ions is 2.5 mM. In another embodiment, wherein each nucleotide triphosphate is present in the transcription reaction at a concentration of 2.0 mM, the concentration of magnesium ions 9.5 mM and concentration of manganese ions is 3.0 mM.

In another embodiment of this aspect, the transcription reaction for use in the aptamer identification method of the invention further comprises a non 2'-OMe guanosine non-triphosphate residue, particularly wherein the non 2'-OMe guanosine non-triphosphate residue selected from the group consisting of: guanosine monophosphate, guanosine diphosphate, 2' flouro guanosine monophosphate, 2' flouro guanosine diphosphate, 2'-amino guanosine monophosphate, 2'-amino guanosine diphosphate, 2'-deoxy guanosine monophosphate, and 2'-deoxy guanosine diphosphate. In another embodiment, the transcription template comprises a T7 RNA polymerase promoter. In another embodiment, the transcription reaction further comprises polyethylene glycol. In another embodiment, the transcription reaction comprises inorganic pyrophosphatase.

The present invention also relates to a method of selecting component sequences of nucleic acid templates for directing transcription. In one embodiment, the component sequence enhances the transcript yield of template directed transcription. In a particular embodiment, the invention relates to methods of selecting leader sequences to enhance transcript yield and to the leader sequences, nucleic acid templates comprising the leader sequences and methods of using the leader sequences and nucleic acid templates of the invention. The present invention also relates to novel mutant polymerases and their use in transcription, particularly its use to enhance transcript yield where 2'modified nucleotides are being incorporated, more particularly where all the nucleotides being incorporate are 2'modified, e.g. are 2'-OMe. The present invention also relates to modified transcription reaction conditions to enhance transcript yield. The present invention particularly relates to pair wise and triple combinations of the above aspects, particularly to improve transcript yield wherein in all but the starting nucleotide of the transcripts are 2'-modified, particularly 2'-OMe modified ("fully 2'-OMe" or "mRmY" or "MNA" transcripts).

In one embodiment of the first aspect of the invention a method of identifying a nucleic acid template component sequence for enhancing transcription, comprising: a) preparing a library of transcription template candidates, wherein the templates comprise a promoter, a first fixed region immediately 3' to the promoter, a degenerate region immediately 3' to the first fixed region and a second fixed region 3' to the degenerate region; b) transcribing the library of transcription template candidates in a transcription reaction to give a library of transcripts; c) reverse transcribing the transcription mixture to obtain a candidate mixture of cDNA wherein the cDNA templates comprise a 5' and 3' terminus; d) ligating a DNA sequence encoding the promoter to the 3' terminus of the cDNA templates in a ligation reaction; e) amplifying the cDNA templates to result in a library of transcription template candidates; and f) identifying a nucleic acid sequence component for enhancing transcription from the library of transcription template candidates, wherein the nucleic acid sequence component comprises a sequence derived from at least a portion of the degenerate region, is provided. In one embodiment of this method of the invention, step f) comprises i) cloning the library of transcription template candidates into individual transcription templates; ii) transcribing the individual transcription templates in a transcription reaction to result in a yield of transcripts; iii) assessing the transcript yield of the individual transcription templates; and iv) identifying the nucleic acid sequence component in a transcription template that results in a predetermined transcript yield. In a particular embodiment of this method of the invention, the predetermined transcript yield is a yield greater than the transcript yield obtained in step b) by transcribing the transcription template candidate mixture.

In another embodiment of this method of the invention step f) comprises analyzing the base composition of the degenerate region of the library of transcription template candidates and identifying the nucleic acid sequence component based on the average base composition of the transcription template candidate library.

In some embodiments of this aspect of the invention step b) of the method further comprises treating the transcribed transcription mixture with DNase. In further embodiments of this method of the invention, step b) further comprises purifying the transcribed transcription mixture by partitioning the transcribed transcription templates away from other components of the transcription reaction. In a particular embodiment of this method of the invention, the purification step comprises replacing the transcription reaction buffer by running the transcription reaction through a desalting column.

In another embodiment of this aspect of the invention, step d) of the method is done before step c). In another embodiment of this aspect of the invention the method comprises repeating steps b) to e) more than once prior to performing step f).

In a further embodiment of this aspect of the invention, the ligation reaction is a splinted ligation reaction and the ligation reaction comprises a nucleic acid splint and a 5'-monophosphorylated oligonucleotide encoding the promoter.

In a particular embodiment of this aspect of the invention, the transcription reaction used in the method comprises one or more modified nucleotide triphosphates and a mutated polymerase. In some embodiments the modified nucleotide triphosphate is a 2'-modified nucleotide triphosphate, particularly a 2'-OMe modified nucleotide triphosphate. In some embodiments, the mutated polymerase is a mutated T7 RNA polymerase. In some embodiments the transcription reaction used in the method of the invention comprises magnesium and manganese ions ($Mn^{2+}$) and the mutated T7 RNA polymerase is selected from the group consisting of: SEQ ID NO 1, SEQ ID NO 2, SEQ ID NO 100 and SEQ ID NO 101.

In some embodiments of this aspect of the invention, the magnesium ions are present in the transcription reaction at a concentration that is between 3.0 to 3.5 times greater than the manganese ions ($Mn^{2+}$). In further embodiments of this aspect of the invention, each nucleotide triphosphate is present in the transcription reaction at a concentration of 1.0 mM, the concentration of magnesium ions is 6.5 mM, and the concentration of manganese ions is 2.0 mM. In further embodiments of this aspect of the invention, each nucleotide triphosphate is present in the transcription reaction at a concentration of 1.5 mM, the concentration of magnesium ions 8 mM, and the concentration of manganese ions is 2.5 mM. In still further embodiments of this aspect of the invention, each nucleotide triphosphate is present in the transcription reaction at a concentration of 2.0 mM, the concentration of magnesium ions 9.5 mM and concentration of manganese ions is 3.0 mM. In some embodiments of the method, the transcription reaction further comprises a polyalkylene glycol, particularly polyethylene glycol. In some embodiments of the method, particularly embodiments in which fully 2'-OMe transcripts are desired, the transcription reaction further comprises a guanosine residue selected from the group consisting of: guanosine monophosphate, guanosine diphosphate, 2' fluoro guanosine monophosphate or diphosphate, 2'-amino guanosine monophosphate or diphosphate, 2'-deoxy guanosine monophosphate or diphosphate, or other modified nucleotides. In further embodiments, the transcription reaction of the method of the invention comprises inorganic pyrophosphatase. In further embodiments, the transcription reaction of the method of the invention optionally comprises combination from the group consisting of: buffer, detergent (e.g., Triton X-100), polyamine (e.g., spermine or spermidine), and reducing agent (e.g., DTT or βME). In yet further embodiments, the transcription reaction of the method of the invention comprises nucleotide triphosphates, magnesium ions, manganese ions (e.g. $Mn^{2+}$), polyethylene glycol, guanosine monophosphate, inorganic pyrophosphatase, buffer, detergent, polyamine, and DTT, and one or more oligonucleotide transcription templates. and a T7 RNA polymerase, e.g. a mutant T7 RNA polymerase, e.g. a mutant T7 RNA polymerase selected from the group consisting of: SEQ ID NO 1, 2, 100 and 101

In some embodiments of the identification method of the invention, the first fixed region of the library of transcription template candidates consists of 2, 3, 4 or 5 guanosine residues. In some embodiments of the invention, the degenerate region of the library of transcription template candidates comprises at least 4, 10, 20 or 30 nucleotides.

In some embodiments of the method, the nucleic acid template component sequence to be identified is a leader sequence. In some embodiments, the leader sequence comprises the first fixed region and a sequence derived from at least a portion of the degenerate region of the library of transcription template candidates. In some embodiments, the method of the invention further comprises incorporating the identified leader sequence into an oligonucleotide transcription template.

The invention also provides leaders sequence identified by the identification method of the invention. In some embodiments, the leader sequence of the invention comprises the nucleic acid sequence from nucleotide 22 to nucleotide 32 in any one of the sequences selected from the group consisting of: SEQ ID NOs 10 to 99. In some embodiments, the leader sequence of the invention comprises the nucleic acid sequence from nucleotide 18 to nucleotide 32 in any one of the sequences selected from the group consisting of: SEQ ID NOs 10-99. The invention also provides an oligonucleotide transcription template comprising a leader sequence of the invention. In particular embodiments the invention provides oligonucleotide transcription template is selected from the group consisting of: SEQ ID NO 3 to 6 and SEQ ID NO 106.

In another aspect of the invention, a method for increasing transcript yield of a nucleic acid where transcription is directed by an oligonucleotide transcription template is provided. In some embodiments of this aspect of the invention, the method of increasing transcript yield comprises directing transcription with an oligonucleotide transcription template that comprises a leader sequence, wherein the leader sequence has been identified by the identification method of the invention using the same nucleotide composition and/or polymerase and/or conditions as used in the transcription reaction for which enhancement of transcript yield is desired.

BRIEF DESCRIPTION OF THE DRAWINGS

FIG. 4 shows the relative transcript yield quantitated from UV-shadowing of PAGE-gel analysis for ARC2118, ARC2119, ARC2120, and ARC2121 using the Y639F/H784A/K378R ("FAR") and Y639L/H784A/K378R ("LAR") mutant T7 RNA polymerases with a 2'-OH GTP spike in the transcription mixture. * indicates that the given yields are relative to ARC2118 transcribed with the LAR mutant polymerase, which gave the highest quantitated yield by UV-shadow.

FIG. 5A shows the nucleic acid (SEQ ID NO 120) and FIG. 5B gives the amino acid sequence of the wild type T7 RNA polymerase (SEQ ID NO 121).

FIG. 6A shows the nucleic acid sequence (SEQ ID NO 122) of mutant T7 RNA polymerase Y639L/H784A. FIG. 6B shows the nucleic acid sequence (SEQ ID NO 123) of T7 mutant polymerase Y639L/H784A/K378R. FIG. 6C shows the nucleic acid sequence (SEQ ID NO 124) of mutant T7 polymerase P266L/Y639L/H784A. FIG. 6D shows the nucleic acid sequence (SEQ ID NO 125) of mutant T7 polymerase P266L/Y639L/H784A/K378R.

FIG. 7 shows the relative transcript yield quantitated from UV-shadowing of PAGE-gel analysis for ARC2118 and ARC2119 using the Y639L/H784A/K378R mutant T7 RNA polymerase with a titration of rGTP (2'-OH GTP) in the transcription mixture. * indicates that the given yields are relative to ARC2118 transcribed with 20 uM rGTP, which gave the highest quantitated yield by UV-shadow.

FIG. 8 shows the relative transcript yield quantitated from UV-shadowing of PAGE-gel analysis for ARC2119 using the Y639L/H784A/K378R mutant T7 RNA polymerase with a varying concentrations of 2'-OMe NTPs (A, U, C, and G), $MgCl_2$ and $MnCl_2$ and no rGTP (2'-OH GTP) in the transcription mixture. The given yields are relative to the 1 mM each 2'-OMe NTP, 6.5 mM $MgCl_2$, and 2 mM $MnCl_2$ transcription condition.

FIG. 9 is a table that shows an analysis of the nucleotide insertions, deletions and substitutions of fully 2'-OMe transcription (100% 2'-OMe A, U, C, G) with the Y639L/H784A/K378R mutant T7 RNA polymerase, compared to the fidelity of all RNA or 2'-OMe transcription using the Y639F/K378R mutant T7 RNA polymerase. In the table, (1) indicates data from "Direct in Vitro Selection of a 2'-O-Methyl Aptamer to VEGF" Burmeister et. al., (2005) Chemistry and Biology, 12: 25-33 where transcriptions were done with FAR T7 mutant polymerase and (2) indicates that transcription was done with LAR T7 mutant polymerase.

FIG. 10 is a table that shows an analysis of the percent nucleotide composition of fully 2'-OMe transcripts (100% 2'-OMe A, T, C, G) before and after one round of fully 2'-OMe transcription using the Y639L/H784A/K378R mutant T7 RNA polymerase followed by DNase treatment, reverse transcription, splinted ligation, and PCR amplification.

FIG. 13 is an illustration depicting various PEGylation strategies representing standard mono-PEGylation, multiple PEGylation, and dimerization via PEGylation.

DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

The SELEX™ Method

Figure 1:
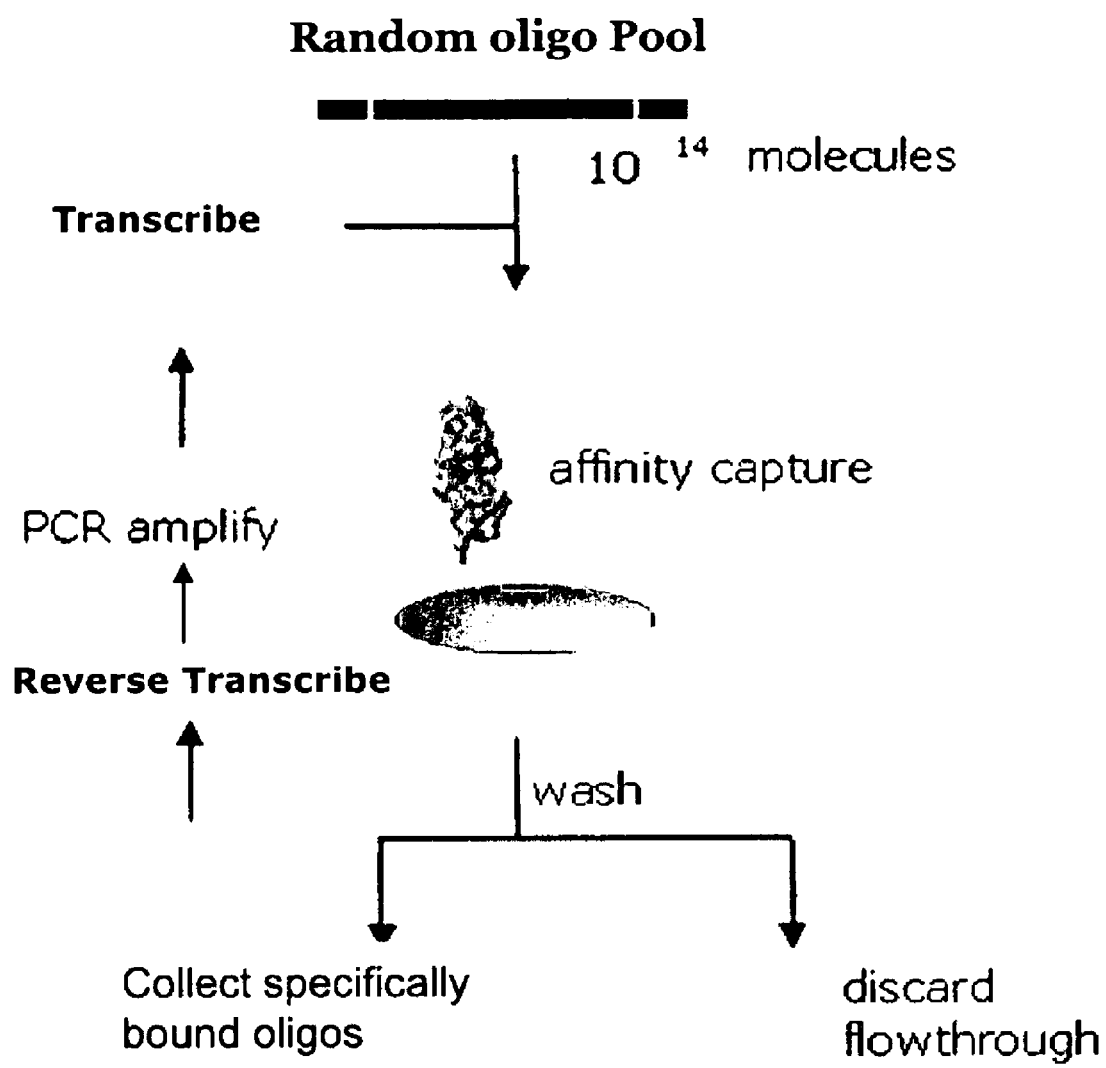
FIG. 1 is a schematic representation of the in vitro aptamer selection (SELEX™) process from pools of random sequence oligonucleotides.

The preferred method for generating an aptamer is with the process entitled "Systematic Evolution of Ligands by Exponential Enrichment" ("SELEX™") generally depicted in FIG. 1 and also referred to as in vitro selection. The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". By performing iterative cycles of selection and amplification SELEX™ may be used to obtain aptamers, also referred to herein as "nucleic acid ligands" with any desired level of target binding affinity.

The SELEX™ process is based on the unique insight that nucleic acids have sufficient capacity for forming a variety of two- and three-dimensional structures and sufficient chemical versatility available within their monomers to act as ligands (i.e., form specific binding pairs) with virtually any chemical compound, whether monomeric or polymeric. Molecules of any size or composition can serve as targets.

The SELEX™ process is based on the ability to bind a target. Aptamers obtained through the SELEX™ procedure will thus have the property of target binding. Mere target binding, however provides no information on the functional effect, if any, which may be exerted on the target by the action of aptamer binding.

Alteration of a property of the target molecule requires the aptamer to bind at a certain location on the target in order to effect a change in a property of the target. In theory, the SELEX™ method may result in the identification of a large number of aptamers, where each aptamer binds at a different site on the target. In practice, aptamer-target binding interactions often occur at one or a relatively small number of preferred binding sites on the target which provide stable and accessible structural interfaces for the interaction. Furthermore, when the SELEX™ method is performed on a physiological target molecule the skilled person is generally not able to control the location of aptamer to the target. Accordingly, the location of the aptamer binding site on the target may or may not be at, or close to, one of potentially several binding sites that could lead to the desired effect, or may not have any effect on the target molecule.

Even where an aptamer, by virtue of its ability to bind the target, is found to have an effect there is no way of predicting the existence of that effect or of knowing in advance what the effect will be. In performing a SELEX™ experiment the skilled person can only know with any certainty that aptamers, to the extent it is possible to obtain an aptamer against a target, will have the property of target binding. One may perform a SELEX™ experiment in the hope that some of the aptamers identified will also have an effect on the target beyond binding to it, but this is uncertain.

The SELEX™ process relies as a starting point upon a large library or pool of single stranded oligonucleotides comprising randomized sequences. The oligonucleotides can be modified or unmodified DNA, RNA, or DNA/RNA hybrids. In some examples, the pool comprises 100% degenerate or partially degenerate oligonucleotides. In other examples, the pool comprises degenerate or partially degenerate oligonucleotides containing at least one fixed sequence and/or conserved sequence incorporated within randomized sequence. In other examples, the pool comprises degenerate or partially degenerate oligonucleotides containing at least one fixed sequence and/or conserved sequence at its 5' and/or 3' end which may comprise a sequence shared by all the molecules of the oligonucleotide pool. Fixed sequences are sequences common to oligonucleotides in the pool which are incorporated for a preselected purpose such as, CpG motifs described further below, hybridization sites for PCR primers, promoter sequences for RNA polymerases (e.g., T3, T4, T7, and SP6), restriction sites, or homopolymeric sequences, such as poly A or poly T tracts, catalytic cores, sites for selective binding to affinity columns, leader sequences which promote transcription, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a degenerate sequence portion as well as fixed sequences necessary for efficient amplification. Typically the oligonucleotides of the starting pool contain fixed 5' and 3' terminal sequences which flank an internal region of 30-40 random nucleotides. The degenerate nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The degenerate sequence portion of the oligonucleotide can be of any length and can comprise ribonucleotides and/or deoxyribonucleotides and can include modified or non-natural nucleotides or nucleotide analogs. See, e.g., U.S. Pat. No. 5,958,691; U.S. Pat. No. 5,660,985; U.S. Pat. No. 5,958,691; U.S. Pat. No. 5,698,687; U.S. Pat. No. 5,817,635; U.S. Pat. No. 5,672,695, and PCT Publication WO 92/07065. Degenerate oligonucleotides can be synthesized from phosphodiester-linked nucleotides using solid phase oligonucleotide synthesis techniques well known in the art. See, e.g., Froehler et al., Nucl. Acid Res. 14:5399-5467 (1986) and Froehler et al., Tet. Lett. 27:5575-5578 (1986). Random oligonucleotides can also be synthesized using solution phase methods such as triester synthesis methods. See, e.g., Sood et al., Nucl. Acid Res. 4:2557 (1977) and Hirose et al., Tet. Lett., 28:2449 (1978). Typical syntheses carried out on automated DNA synthesis equipment yield $10^{16}$-$10^{17}$ individual molecules, a number sufficient for most SELEX™ experiments. Sufficiently large regions of degenerate sequence in the sequence design increases the likelihood that each synthesized molecule is likely to represent a unique sequence.

The starting library of oligonucleotides may be generated by automated chemical synthesis on a DNA synthesizer. To synthesize degenerate sequences, mixtures of all four nucleotides are added at each nucleotide addition step during the synthesis process, allowing for stochastic incorporation of nucleotides. As stated above, in one embodiment, random oligonucleotides comprise entirely degenerate sequences; however, in other embodiments, degenerate oligonucleotides can comprise stretches of nonrandom or partially random sequences. Partially random sequences can be created by adding the four nucleotides in different molar ratios at each addition step.

In those instances where an RNA library is to be used as the starting library it is typically generated by synthesizing a DNA library, optionally PCR amplifying, then transcribing the DNA library in vitro using T7 RNA polymerase or a modified T7 RNA polymerase, and purifying the transcribed library. The RNA or DNA library is then mixed with the target under conditions favorable for binding and subjected to stepwise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding; (b) partitioning unbound nucleic acids from those nucleic acids which have bound specifically to target molecules; (c) optionally dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. A nucleic acid mixture comprising, for example, a 20 nucleotide randomized segment can have $4^{20}$ candidate possibilities. Those which have the higher affinity (lower dissociation constants) for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested as ligands or aptamers for 1) target binding affinity; and/or 2) ability to effect target function Cycles of selection and amplification are repeated until a desired goal is achieved. In the most general case, selection/amplification is continued until no significant improvement in binding strength is achieved on repetition of the cycle. The method is typically used to sample approximately $10^{14}$ different nucleic acid species but may be used to sample as many as about $10^{18}$ different nucleic acid species. Generally, nucleic acid aptamer molecules are selected in a 5 to 20 cycle procedure. In one embodiment, heterogeneity is introduced only in the initial selection stages and does not occur throughout the replicating process.

In one embodiment of the SELEX™ method, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of the SELEX™ process until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX™ process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX™ procedures with contiguous randomized segments be initiated with nucleic acid sequences containing a randomized segment of between about 20 to about 50 nucleotides and in some embodiments, about 30 to about 40 nucleotides. In one example, the 5'-fixed:random:3'-fixed sequence comprises a random sequence of about 30 to about 40 nucleotides.

The core SELEX™ method has been modified to achieve a number of specific objectives. For example, U.S. Pat. No. 5,707,796 describes the use of the SELEX™ process in conjunction with gel electrophoresis to select nucleic acid molecules with specific structural characteristics, such as bent DNA. U.S. Pat. No. 5,763,177 describes SELEX™ based methods for selecting nucleic acid ligands containing photoreactive groups capable of binding and/or photo-crosslinking to and/or photo-inactivating a target molecule. U.S. Pat. No. 5,567,588 and U.S. Pat. No. 5,861,254 describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target.

The SELEX™ method can also be used to obtain nucleic acid ligands that bind to more than one site on the target molecule, and to obtain nucleic acid ligands that include non-nucleic acid species that bind to specific sites on the target. The SELEX™ method provides means for isolating and identifying nucleic acid ligands which bind to any envisionable target, including large and small biomolecules such as nucleic acid-binding proteins and proteins not known to bind nucleic acids as part of their biological function as well as cofactors and other small molecules. For example, U.S. Pat. No. 5,580,737 discloses nucleic acid sequences identified through the SELEX™ method which are capable of binding with high affinity to caffeine and the closely related analog, theophylline.

The Counter-SELEX™ process is a method for improving the specificity of nucleic acid ligands to a target molecule by eliminating nucleic acid ligand sequences with cross-reactivity to one or more non-target molecules. The Counter-SELEX™ process is comprised of the steps of: (a) preparing a candidate mixture of nucleic acids; (b) contacting the candidate mixture with the target, wherein nucleic acids having an increased affinity to the target relative to the candidate mixture may be partitioned from the remainder of the candidate mixture; (c) partitioning the increased affinity nucleic acids from the remainder of the candidate mixture; (d) optionally dissociating the increased affinity nucleic acids from the target; (e) contacting the increased affinity nucleic acids with one or more non-target molecules such that nucleic acid ligands with specific affinity for the non-target molecule(s) are removed; and (f) amplifying the nucleic acids with specific affinity only to the target molecule to yield a mixture of nucleic acids enriched for nucleic acid sequences with a relatively higher affinity and specificity for binding to the target molecule. As described above for the SELEX™ method, cycles of selection and amplification are repeated as necessary until a desired goal is achieved.

One potential problem encountered in the use of nucleic acids as therapeutics and vaccines is that oligonucleotides in their phosphodiester form may be quickly degraded in body fluids by intracellular and extracellular enzymes such as endonucleases and exonucleases before the desired effect is manifest. The SELEX™ method thus encompasses the identification of high-affinity nucleic acid ligands containing modified nucleotides conferring improved characteristics on the ligand, such as improved in vivo stability or improved delivery characteristics. Examples of such modifications include chemical substitutions at the sugar and/or phosphate and/or base positions. SELEX™-identified nucleic acid ligands containing modified nucleotides are described, e.g., in U.S. Pat. No. 5,660,985, which describes oligonucleotides containing nucleotide derivatives chemically modified at the 2'-position of ribose, 5-position of pyrimidines, and 8-position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-O-methyl (2'-OMe) substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Modifications to generate oligonucleotide populations which are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, and unusual base-pairing combinations such as the isobases isocytidine and isoguanosine. Modifications can also include 3' and 5' modifications such as capping. Modifications can also include 3' and 5' modifications such as capping, e.g., addition of a 3'-3'-dT cap to increase exonuclease resistance (see, e.g., U.S. Pat. Nos. 5,674,685; 5,668,264; 6,207,816; and 6,229,002, each of which is incorporated by reference herein in its entirety).

In one embodiment, oligonucleotides are provided in which the P(O)O group is replaced by P(O)S ("thioate"), P(S)S ("dithioate"), P(O)$NR_2$ ("amidate"), P(O)R, P(O)OR', CO or $CH_2$ ("formacetal") or 3'-amine (—NH—$CH_2$—$CH_2$—), wherein each R or R' is independently H or substituted or unsubstituted alkyl. Linkage groups can be attached to adjacent nucleotides through an —O—, —N—, or —S— linkage. Not all linkages in the oligonucleotide are required to be identical.

In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat, et al., Nucl. Acid Res. 19:733-738 (1991); Cotten, et al., Nucl. Acid Res. 19:2629-2635 (1991); and Hobbs, et al., Biochemistry 12:5138-5145 (1973). Other modifications are known to one of ordinary skill in the art. Such modifications may be pre-SELEX™ process modifications or post-SELEX™ process modifications (modification of previously identified unmodified ligands) or may be made by incorporation into the SELEX™ process.

Pre-SELEX™ process modifications or those made by incorporation into the SELEX™ process yield nucleic acid ligands with both specificity for their SELEX™ target and improved stability, e.g., in vivo stability. Post-SELEX™ process modifications ((e.g., truncation, deletion, substitution or additional nucleotide modifications of previously identified ligands having nucleotides incorporated by pre-SELEX™ process modification) to nucleic acid ligands can result in improved stability, e.g., in vivo stability without adversely affecting the binding capacity of the nucleic acid ligand. Optionally, aptamers in which modified nucleotides have been incorporated by pre-SELEX™ process modification can be further modified by post-SELEX™ process modification (i.e., a post-SELEX™ modification process after SELEX).

The SELEX™ method encompasses combining selected oligonucleotides with other selected oligonucleotides and non-oligonucleotide functional units as described in U.S. Pat. No. 5,637,459 and U.S. Pat. No. 5,683,867. The SELEX™ method further encompasses combining selected nucleic acid ligands with lipophilic or non-immunogenic high molecular weight compounds in a diagnostic or therapeutic complex, as described, e.g., in U.S. Pat. No. 6,011,020, U.S. Pat. No. 6,051,698, and PCT Publication No. WO 98/18480. These patents and applications teach the combination of a broad array of shapes and other properties, with the efficient amplification and replication properties of oligonucleotides, and with the desirable properties of other molecules.

The identification of nucleic acid ligands to small, flexible peptides via the SELEX™ method has also been explored. Small peptides have flexible structures and usually exist in solution in an equilibrium of multiple conformers, and thus it was initially thought that binding affinities may be limited by the conformational entropy lost upon binding a flexible peptide. However, the feasibility of identifying nucleic acid ligands to small peptides in solution was demonstrated in U.S. Pat. No. 5,648,214. In this patent, high affinity RNA nucleic acid ligands to substance P, an 11 amino acid peptide, were identified.

As part of the SELEX™ process, the sequences selected to bind to the target are then optionally minimized to determine the minimal sequence having the desired binding affinity. The selected sequences and/or the minimized sequences are optionally modified by performing random or directed mutagenesis of the sequence to, e.g., increase binding affinity or alternatively to determine which positions in the sequence are essential for binding activity.

The 2'-Modified SELEX™ Method

In order for an aptamer to be suitable for use as a therapeutic and/or for particular types of diagnostics, it is preferably inexpensive to synthesize, safe and stable in vivo. Wild-type RNA and DNA aptamers are typically not stable in vivo because of their susceptibility to degradation by nucleases. Resistance to nuclease degradation can be greatly increased by the incorporation of modifying groups at the 2'-position.

2'-fluoro and 2'-amino groups have been successfully incorporated into oligonucleotide pools from which aptamers have been subsequently selected. However, these modifications greatly increase the cost of synthesis of the resultant aptamer, and may introduce safety concerns in some cases because of the possibility that the modified nucleotides could be recycled into host DNA by degradation of the modified oligonucleotides and subsequent use of the nucleotides as substrates for DNA synthesis.

Aptamers that contain 2'-O-methyl ("2'-OMe") nucleotides, as provided herein, overcome many of these drawbacks. Oligonucleotides containing 2'-OMe nucleotides are nuclease-resistant and inexpensive to synthesize. Although 2'-OMe nucleotides are ubiquitous in biological systems, natural polymerases do not accept 2'-OMe NTPs as substrates under physiological conditions, thus there are no safety concerns over the recycling of 2'-OMe nucleotides into host DNA. SELEX™ methods used to generate 2'-modified aptamers are described, e.g., in U.S. Provisional Patent Application Ser. No. 60/430,761, filed Dec. 3, 2002, U.S. Provisional Patent Application Ser. No. 60/487,474, filed Jul. 15, 2003, U.S. Provisional Patent Application Ser. No. 60/517, 039, filed Nov. 4, 2003, U.S. patent application Ser. No. 10/729,581, filed Dec. 3, 2003, and U.S. patent application Ser. No. 10/873,856, filed Jun. 21, 2004, entitled "Method for in vitro Selection of 2'-O-methyl Substituted Nucleic Acids," each of which is herein incorporated by reference in its entirety.

The present invention includes aptamers that bind to and modulate the function of the aptamer target and which contain modified nucleotides (e.g., nucleotides which have a modification at the 2'-position) to make the oligonucleotide more stable than the unmodified oligonucleotide to enzymatic and chemical degradation as well as thermal and physical degradation. Although there are several examples of 2'-OMe containing aptamers in the literature (see, e.g., Ruckman et al., J.Biol.Chem, 1998 273, 20556-20567-695) these were generated by the in vitro selection of libraries of modified transcripts in which the C and U residues were 2'-fluoro (2'-F) substituted and the A and G residues were 2'-OH. Once functional sequences were identified then each A and G residue was tested for tolerance to 2'-OMe substitution, and the aptamer was re-synthesized having all A and G residues which tolerated 2'-OMe substitution as 2'-OMe residues. Most of the A and G residues of aptamers generated in this two-step fashion tolerate substitution with 2'-OMe residues, although, on average, approximately 20% do not. Consequently, aptamers generated using this method tend to contain from two to four 2'-OH residues, and stability and cost of synthesis are compromised as a result. By incorporating modified nucleotides into the transcription reaction which generate stabilized oligonucleotides used in oligonucleotide pools from which aptamers are selected and enriched by the SELEX™ method (and/or any of its variations and improvements, including those described herein), the methods of the present invention eliminate the need for stabilizing the selected aptamer oligonucleotides by resynthesizing the aptamer oligonucleotides with 2'-OMe modified nucleotides.

In one embodiment, the present invention provides aptamers comprising combinations of 2'-OH, 2'-F, 2'-deoxy, and 2'-OMe modifications of the ATP, GTP, CTP, TTP, and UTP nucleotides. In another embodiment, the present invention provides aptamers comprising combinations of 2'-OH, 2'-F, 2'-deoxy, 2'-OMe, 2'-NH$_2$, and 2'-methoxyethyl modifications of the ATP, GTP, CTP, TTP, and UTP nucleotides. In a preferred embodiment, the present invention provides aptamers comprising all or substantially all 2'-OMe modified ATP, GTP, CTP, TTP, and/or UTP nucleotides.

Modified Polymerases

2'-modified aptamers of the invention are created using modified polymerases, e.g., a modified T7 polymerase, having a rate of incorporation of modified nucleotides having bulky substituents at the furanose 2' position that is higher than that of wild-type polymerases. For example, a mutant T7 polymerase in which the tyrosine residue at position 639 has been changed to phenylalanine (Y639F) readily utilizes 2'deoxy, 2'amino-, and 2'fluoro-nucleotide triphosphates (NTPs) as substrates and has been widely used to synthesize modified RNAs for a variety of applications. However, this mutant T7 polymerase reportedly can not readily utilize (i.e., incorporate) NTPs with bulky 2'-substituents such as 2'-OMe or 2'-azido (2'-N$_3$) substituents. For incorporation of bulky 2' substituents, a mutant T7 polymerase having the histidine at position 784 changed to an alanine residue in addition to the Y639F mutation has been described (Y639F/H784A) and has been used in limited circumstances to incorporate modified pyrimidine NTPs. See Padilla, R. and Sousa, R., Nucleic Acids Res., 2002, 30(24): 138. A mutant T7 RNA polymerase in which the tyrosine residue at position 639 has been changed to phenylalanine, the histidine residue at position 784 has been changed to an alanine, and the lysine residue at position 378 has been changed to arginine (Y639F/H784A/ K378R) has been used in limited circumstances to incorporate modified purine and pyrimidine NTPs, e.g., 2'-OMe NTPs, but includes a spike of 2'-OH GTP for transcription. See Burmeister et. al., (2005) Chemistry and Biology, 12: 25-33. The inclusion of a 2'-OH GTP spike for transcription may result in aptamers that are not fully 2'-OMe but rather may depend on the presence of 2'-OH GTPs.

A mutant T7 polymerase having the histidine at position 784 changed to an alanine residue (H784A) has also been described. Padilla et al., Nucleic Acids Research, 2002, 30: 138. In both the Y639F/H784A mutant and H784A mutant T7 polymerases, the change to a smaller amino acid residue such as alanine allows for the incorporation of bulkier nucleotide substrates, e.g., 2'-OMe substituted nucleotides. See Chelliserry, K. and Ellington, A. D., (2004) Nature Biotech, 9:1155-60. Additional T7 RNA polymerases have been described with mutations in the active site of the T7 RNA polymerase which more readily incorporate bulky 2'-modified substrates, e.g., a mutant T7 RNA polymerase having the tyrosine residue at position 639 changed to a leucine (Y639L). However activity is often sacrificed for increased substrate specificity conferred by such mutations, leading to low transcript yields. See Padilla R and Sousa, R., (1999) Nucleic Acids Res., 27(6): 1561. The T7 RNA polymerase mutant P266L has been described to facilitate promoter clearance (Guillerez et al. (2005) Proc. Nat. Acad. Sci. USA, 102 (17) 5958). The polymerase makes a transition from the initiation conformation, in which it is bound to the promoter, to the elongation conformation in which it is not. None of the above mutant polymerases were reported to result in fully 2'-OMe transcripts.

The present invention provides materials and methods for increasing the transcription yield of oligonucleotides. In one embodiment, the present invention provides methods and conditions for using modified T7 RNA polymerases to enzymatically incorporate modified nucleotides into oligonucleotides. In a preferred embodiment, the modified T7 RNA polymerase used with the transcription methods of the invention does not require the presence of 2'-OH GTP. In a preferred embodiment, the modified polymerase is a mutant T7 RNA polymerase having the tyrosine residue at position 639 changed to a leucine residue and the histidine residue at position 784 changed to an alanine residue (Y639L/H784A). In another preferred embodiment, the modified polymerase is a mutant T7 RNA polymerase having the tyrosine residue at position 639 changed to a leucine residue, the histidine residue at position 784 changed to an alanine residue, and the lysine residue at position 378 changed to an arginine residue (Y639L/H784A/K378R). In another embodiment, the modified polymerase for use in the methods of the invention is a mutant T7 RNA polymerase having the tyrosine residue at position 639 changed to a leucine (Y639L) while in yet another embodiment the mutant T7 RNA polymerase has the tyrosine residue at position 639 changed to a leucine residue and the lysine residue at position 378 changed to an arginine residue (Y639L/K378R). While not wishing to be bound by any theory, the K378R mutation is not near the active site of the polymerase and thus is believed to be a silent mutation. In another embodiment, the modified polymerase for use in the methods of the invention is a mutant T7 RNA polymerase having the proline residue at position 266 changed to a leucine, the tyrosine residue at position 639 changed to a leucine and the histidine residue at position 784 changed to an alanine residue, (P266L/Y639L/H784A) while in yet another embodiment the mutant T7 RNA polymerase has the proline residue at position 266 changed to a leucine, the tyrosine residue at position 639 changed to a leucine residue, the histidine residue at position 784 changed to an alanine residue and the lysine residue at position 378 changed to an arginine residue (P266L/Y639L/H784A/K378R).

The amino acid sequences of the mutant T7 RNA polymerases are shown below:

Y639L/H784A (SEQ ID NO 1):
MNTINIAKNDFSDIELAAIPFNTLADHYGERLAREQLALEHESYEMGEAR

FRKMFERQLKAGEVADNAAAKPLITTLLPKMIARINDWFEEVKAKRGKRP

TAFQFLQEIKPEAVAYITIKTTLACLTSADNTTVQAVASAIGRAIEDEAR

FGRIRDLEAKHFKKNVEEQLNKRVGHVYKKAFMQVVEADMLSKGLLGGEA

WSSWHKEDSIHVGVRCIEMLIESTGMVSLHRQNAGVVGQDSETIELAPEY

AEAIATRAGALAGISPMFQPCVVPPKPWTGITGGGYWANGRRPLALVRTH

SKKALMRYEDVYMPEVYKAINIAQNTAWKINKKVLAVANVITKWKHCPVE

DIPAIEREELPMKPEDIDMNPEALTAWKRAAAAVYRKDKARKSRRISLEF

MLEQANKFANHKAIWFPYNMDWRGRVYAVSMFNPQGNDMTKGLLTLAKGK

PIGKEGYYWLKIHGANCAGVDKVPFPERIKFIEENHENIMACAKSPLENT

WWAEQDSPFCFLAFCFEYAGVQHHGLSYNCSLPLAFDGSCSGIQHFSAML

RDEVGGRAVNLLPSETVQDIYGIVAKKVNEILQADAINGTDNEVVTVTDE

NTGEISEKVKLGTKALAGQWLAYGVTRSVTKRSVMTLALGSKEFGFRQQV

LEDTIQPAIDSGKGLMFTQPNQAAGYMAKLIWESVSVTVVAAVEAMNWLK

SAAKLLAAEVKDKKTGEILRKRCAVHWVTPDGFPVWQEYKKPIQTRLNLM

FLGQFRLQPTINTNKDSEIDAHKQESGIAPNFVASQDGSHLRKTVVWAHE

KYGIESFALIHDSFGTIPADAANLFKAVRETMVDTYESCDVLADFYDQFA

DQLHESQLDKMPALPAKGNLNLRDILESDFAFA

Y639L/H784A/K378R (SEQ ID NO 2):
MNTINIAKNDFSDIELAAIPFNTLADHYGERLAREQLALEHESYEMGEAR

FRKMFERQLKAGEVADNAAAKPLITTLLPKMIARINDWFEEVKAKRGKRP

TAFQFLQEIKPEAVAYITIKTTLACLTSADNTTVQAVASAIGRAIEDEAR

FGRIRDLEAKHFKKNVEEQLNKRVGHVYKKAFMQVVEADMLSKGLLGGEA

WSSWHKEDSIHVGVRCIEMLIESTGMVSLHRQNAGVVGQDSETIELAPEY

AEAIATRAGALAGISPMFQPCVVPPKPWTGITGGGYWANGRRPLALVRTH

SKKALMRYEDVYMPEVYKAINIAQNTAWKINKKVLAVANVITKWKHCPVE

DIPAIEREELPMKPEDIDMNPEALTAWRRAAAAVYRKDKARKSRRISLEF

MLEQANKFANHKAIWFPYNMDWRGRVYAVSMFNPQGNDMTKGLLTLAKGK

PIGKEGYYWLKIHGANCAGVDKVPFPERIKFIEENHENIMACAKSPLENT

WWAEQDSPFCFLAFCFEYAGVQHHGLSYNCSLPLAFDGSCSGIQHFSAML

RDEVGGRAVNLLPSETVQDIYGIVAKKVNEILQADAINGTDNEVVTVTDE

NTGEISEKVKLGTKALAGQWLAYGVTRSVTKRSVMTLALGSKEFGFRQQV

LEDTIQPAIDSGKGLMFTQPNQAAGYMAKLIWESVSVTVVAAVEAMNWLK

SAAKLLAAEVKDKKTGEILRKRCAVHWVTPDGFPVWQEYKKPIQTRLNLM

FLGQFRLQPTINTNKDSEIDAHKQESGIAPNFVASQDGSHLRKTVVWAHE

KYGIESFALIHDSFGTIPADAANLFKAVRETMVDTYESCDVLADFYDQFA

DQLHESQLDKMPALPAKGNLNLRDILESDFAFA

Y639L (SEQ ID NO 100):
MNTINIAKNDFSDIELAAIPFNTLADHYGERLAREQLALEHESYEMGEAR

FRKMFERQLKAGEVADNAAAKPLITTLLPKMIARINDWFEEVKAKRGKRP

TAFQFLQEIKPEAVAYITIKTTLACLTSADNTTVQAVASAIGRAIEDEAR

FGRIRDLEAKHFKKNVEEQLNKRVGHVYKKAFMQVVEADMLSKGLLGGEA

WSSWHKEDSIHVGVRCIEMLIESTGMVSLHRQNAGVVGQDSETIELAPEY

AEAIATRAGALAGISPMFQPCVVPPKPWTGITGGGYWANGRRPLALVRTH

SKKALMRYEDVYMPEVYKAINIAQNTAWKINKKVLAVANVITKWKHCPVE

DIPAIEREELPMKPEDIDMNPEALTAWKRAAAAVYRKDKARKSRRISLEF

MLEQANKFANHKAIWFPYNMDWRGRVYAVSMFNPQGNDMTKGLLTLAKGK

PIGKEGYYWLKIHGANCAGVDKVPFPERIKFIEENHENIMACAKSPLENT

WWAEQDSPFCFLAFCFEYAGVQHHGLSYNCSLPLAFDGSCSGIQHFSAML

RDEVGGRAVNLLPSETVQDIYGIVAKKVNEILQADAINGTDNEVVTVTDE

NTGEISEKVKLGTKALAGQWLAYGVTRSVTKRSVMTLALGSKEFGFRQQV

LEDTIQPAIDSGKGLMFTQPNQAAGYMAKLIWESVSVTVVAAVEAMNWLK

SAAKLLAAEVKDKKTGEILRKRCAVHWVTPDGFPVWQEYKKPIQTRLNLM

FLGQFRLQPTINTNKDSEIDAHKQESGIAPNFVHSQDGSHLRKTVVWAHE

KYGIESFALIHDSFGTIPADAANLFKAVRETMVDTYESCDVLADFYDQFA

DQLHESQLDKMPALPAKGNLNLRDILESDFAFA

Y639L/K378R (SEQ ID NO 101):
MNTINIAKNDFSDIELAAIPFNTLADHYGERLAREQLALEHESYEMGEAR

FRKMFERQLKAGEVADNAAAKPLITTLLPKMIARINDWFEEVKAKRGKRP

TAFQFLQEIKPEAVAYITIKTTLACLTSADNTTVQAVASAIGRAIEDEAR

FGRIRDLEAKHFKKNVEEQLNKRVGHVYKKAFMQVVEADMLSKGLLGGEA

WSSWHKEDSIHVGVRCIEMLIESTGMVSLHRQNAGVVGQDSETIELAPEY

AEAIATRAGALAGISPMFQPCVVPPKPWTGITGGGYWANGRRPLALVRTH

SKKALMRYEDVYMPEVYKAINIAQNTAWKINKKVLAVANVITKWKHCPVE

DIPAIEREELPMKPEDIDMNPEALTAWRRAAAAVYRKDKARKSRRISLEF

MLEQANKFANHKAIWFPYNMDWRGRVYAVSMFNPQGNDMTKGLLTLAKGK

PIGKEGYYWLKIHGANCAGVDKVPFPERIKFIEENHENIMACAKSPLENT

WWAEQDSPFCFLAFCFEYAGVQHHGLSYNCSLPLAFDGSCSGIQHFSAML

RDEVGGRAVNLLPSETVQDIYGIVAKKVNEILQADAINGTDNEVVTVTDE

NTGEISEKVKLGTKALAGQWLAYGVTRSVTKRSVMTLALGSKEFGFRQQV

LEDTIQPAIDSGKGLMFTQPNQAAGYMAKLIWESVSVTWAAVEAMNWLKS

AAKLLAAEVKDKKTGEILRKRCAVHWVTPDGFPVWQEYKKPIQTRLNLMF

LGGQFRLQPTINTNKDSEIDAHKQESGIAPNFVHSQDGSHLRKTVVWAHEK

YGIESFALIHDSFGTIPADAANLFKAVRETMVDTYESCDVLADFYDQFAD

QLHESQLDKMPALPAKGNLNLRDILESDFAFA

P266L/Y639L/H784A (SEQ ID NO 102)
MNTINIAKNDFSDIELAAIPFNTLADHYGERLAREQLALEHESYEMGEAR

FRKMFERQLKAGEVADNAAAKPLITTLLPKMIARINDWFEEVKAKRGKRP

TAFQFLQEIKPEAVAYITIKTTLACLTSADNTTVQAVASAIGRAIEDEAR

FGRIRDLEAKHFKKNVEEQLNKRVGHVYKKAFMQVVEADMLSKGLLGGEA

WSSWHKEDSIHVGVRCIEMLIESTGMVSLHRQNAGVVGQDSETIELAPEY

AEAIATRAGALAGISLMFQPCVVPPKPWTGITGGGYWANGRRPLALVRTH

SKKALMRYEDVYMPEVYKAINIAQNTAWKINKKVLAVANVITKWKHCPVE

DIPAIEREELPMKPEDIDMNPEALTAWKRAAAAVYRKDKARKSRRISLEF

MLEQANKFANHKAIWFPYNMDWRGRVYAVSMFNPQGNDMTKGLLTLAKGK

PIGKEGYYWLKIHGANCAGVDKVPFPERIKFIEENHENIMACAKSPLENT

WWAEQDSPFCFLAFCFEYAGVQHHGLSYNCSLPLAFDGSCSGIQHFSAML

RDEVGGRAVNLLPSETVQDIYGIVAKKVNEILQADAINGTDNEVVTVTDE

NTGEISEKVKLGTKALAGQWLAYGVTRSVTKRSVMTLALGSKEFGFRQQV

LEDTIQPAIDSGKGLMFTQPNQAAGYMAKLIWESVSVTVVAAVEAMNWLK

SAAKLLAAEVKDKKTGEILRKRCAVHWVTPDGFPVWQEYKKPIQTRLNLM

FLGQFRLQPTINTNKDSEIDAHKQESGIAPNFVASQDGSHLRKTVVWAHE

KYGIESFALIHDSFGTIPADAANLFKAVRETMVDTYESCDVLADFYDQFA

DQLHESQLDKMPALPAKGNLNLRDILESDFAFA

P266L/Y639L/H784A/K378R (SEQ ID NO 103)
MNTINIAKNDFSDIELAAIPFNTLADHYGERLAREQLALEHESYEMGEAR

FRKMFERQLKAGEVADNAAAKPLITTLLPKMIARINDWFEEVKAKRGKRP

TAFQFLQEIKPEAVAYITIKTTLACLTSADNTTVQAVASAIGRAIEDEAR

FGRIRDLEAKHFKKNVEEQLNKRVGHVYKKAFMQVVEADMLSKGLLGGEA

WSSWHKEDSIHVGVRCIEMLIESTGMVSLHRQNAGVVGQDSETIELAPEY

AEAIATRAGALAGISLMFQPCVVPPKPWTGITGGGYWANGRRPLALVRTH

SKKALMRYEDVYMPEVYKAINIAQNTAWKINKKVLAVANVITKWKHCPVE

DIPAIEREELPMKPEDIDMNPEALTAWRRAAAAVYRKDKARKSRRISLEF

MLEQANKFANHKAIWFPYNMDWRGRVYAVSMFNPQGNDMTKGLLTLAKGK

PIGKEGYYWLKIHGANCAGVDKVPFPERIKFIEENHENIMACAKSPLENT

WWAEQDSPFCFLAFCFEYAGVQHHGLSYNCSLPLAFDGSCSGIQHFSAML

RDEVGGRAVNLLPSETVQDIYGIVAKKVNEILQADAINGTDNEVVTVTDE

NTGEISEKVKLGTKALAGQWLAYGVTRSVTKRSVMTLALGSKEFGFRQQV

LEDTIQPAIDSGKGLMFTQPNQAAGYMAKLIWESVSVTVVAAVEAMNWLK

SAAKLLAAEVKDKKTGEILRKRCAVHWVTPDGFPVWQEYKKPIQTRLNLM

FLGQFRLQPTINTNKDSEIDAHKQESGIAPNFVASQDGSHLRKTVVWAHE

KYGIESFALIHDSFGTIPADAANLFKAVRETMVDTYESCDVLADFYDQFA

DQLHESQLDKMPALPAKGNLNLRDILESDFAFA

To generate pools of 2'-modified (e.g., 2'-OMe) RNA transcripts under conditions in which a polymerase accepts 2'-modified NTPs, the Y639F, Y639F/K378R, Y639F/H784A, Y639F/H784A/K378R, Y639L/H784A, Y639L/H784A/K378R, Y639L, Y639L/K378R, P266L/Y639L/H784A or P266L/Y639L/H784A/K378R mutant T7 RNA polymerases can be used. A preferred polymerase is the Y639L/H784A mutant T7 RNA polymerase. Another preferred polymerase is the Y639L/H784A/K378R mutant T7 RNA polymerase. Another preferred polymerase of the invention is the P266L/Y639L/H784A or P266L/Y639L/H784A/K378R mutant T7 RNA polymerase. Other T7 RNA polymerases, particularly those that exhibit a high tolerance for bulky 2'-substituents, may also be used in the methods of the present invention. When used in a template-directed polymerization using the conditions disclosed herein, the Y639L/H784A, the Y639L/H784A/K378R, P266L/Y639L/H784A or P266L/Y639L/H784A/K378R mutant T7 RNA polymerase can be used for the incorporation of all 2'-OMe NTPs, including 2'-OMe GTP, with higher transcript yields than achieved by using the Y639F, Y639F/K378R, Y639F/H784A, Y639F/H784A/K378R, Y639L, or the Y639L/K378R mutant T7 RNA polymerases. The Y639L/H784A, Y639L/H784A/K378R, P266L/Y639L/H784A or P266L/Y639L/H784A/K378R mutant T7 RNA polymerases can be used with but does not require 2'-OH GTP to achieve high yields of 2'-modified, e.g., 2'-OMe containing oligonucleotides.

In a preferred embodiment, the Y639L/H784A or the Y639L/H784A/K378R mutant T7 RNA polymerases of the invention are used with an MNA transcription mixture to promote higher fully 2'-OMe transcript yields. In some embodiments, Y639L/H784A or the Y639L/H784A/K378R mutant T7 RNA polymerases may be used with an rRmY, dRmY, rGmH, fGmH, dGmH, dAmB, rRdY, dRdY or rN transcription mixture.

As used herein, a transcription mixture containing only 2'-OMe A, G, C, and U triphosphates is referred to as an MNA mixture, and aptamers selected therefrom are referred to as MNA aptamers and contains only 2'-O-methyl nucleotides. A transcription mixture containing 2'-OMe C and U and 2'-OH A and G is referred to as an "rRmY" mixture and aptamers selected therefrom are referred to as "rRmY" aptamers. A transcription mixture containing deoxy A and G and 2'-OMe U and C is referred to as a "dRmY" mixture and aptamers selected therefrom are referred to as "dRmY" aptamers. A transcription mixture containing 2'-OMe A, C, and U, and 2'-OH G is referred to as a "rGmH" mixture and aptamers selected therefrom are referred to as "rGmH" aptamers. A transcription mixture alternately containing 2'-OMe A, C, U and G and 2'-OMe A, U and C and 2'-F G is referred to as an "alternating mixture" and aptamers selected therefrom are referred to as "alternating mixture" aptamers. A transcription mixture containing 2'-OMeA, U, and C, and 2'-F G is referred to as a "fGmH" mixture and aptamers selected therefrom are referred to as "fGmH" aptamers. A transcription mixture containing 2'-OMe A, U, and C, and deoxy G is referred to as a "dGmH" mixture and aptamers selected therefrom are referred to as "dGmH" aptamers. A transcription mixture containing deoxy A, and 2'-OMe C, G and U is referred to as a "dAmB" mixture and aptamers selected therefrom are referred to as "dAmB" aptamers. A transcription mixture containing 2'-OH A and 2'-OMe C, G and U is referred to as a "rAmB" mixture and aptamers selected therefrom are referred to as "rAmB" aptamers. A transcription mixture containing 2'-OH adenosine triphosphate and guanosine triphosphate and deoxy cytidine triphosphate and thymidine triphosphate is referred to as an rRdY mixture and aptamers selected therefrom are referred to as "rRdY" aptamers. A transcription mixture containing all 2'-OH nucleotides is referred to as a "rN" mixture and aptamers selected therefrom are referred to as "rN", "rRrY" or RNA aptamers, and a transcription mixture containing all deoxy nucleotides is referred to as a "dN" mixture and aptamers selected therefrom are referred to as "dN" or "dRdY" or DNA aptamers.

2'-modified oligonucleotides may be synthesized entirely of modified nucleotides, or with a subset of modified nucleotides. All nucleotides may be modified, and all may contain the same modification. All nucleotides may be modified, but contain different modifications, e.g., all nucleotides containing the same base may have one type of modification, while nucleotides containing other bases may have different types of modification. All purine nucleotides may have one type of modification (or are unmodified), while all pyrimidine nucleotides have another, different type of modification (or are unmodified). In this manner, transcripts, or pools of transcripts are generated using any combination of modifications, including for example, ribonucleotides (2'-OH), deoxyribonucleotides (2'-deoxy), 2'-F, and 2'-OMe nucleotides. Additionally modified oligonucleotides may contain nucleotides bearing more than one modification simultaneously such as a modification at the internucleotide linkage (eg phosphorothioate) and at the sugar (eg 2'-OMe) and the base (eg inosine).

Transcription Conditions

A number of factors have been determined to be important for the transcription conditions of the 2'-modified SELEX™ method, which may also apply to the Terminal Region SELEX™ methods described below. For example, increases in the yields of modified transcript may be observed under some conditions when a particular leader sequence/mutant polymerase combination is used. A leader sequence is a sequence that can be incorporated into the 3' end of a fixed sequence at the 5' end of the DNA transcription template. The leader sequence is typically 6-15 nucleotides long, and may be composed of a predetermined nucleotide composition, for example it may be all purines, or a particular mixture of purine and pyrimidine nucleotides.

Examples of templates that may be used with the mutant polymerases and transcription conditions of the invention, particularly in combination with Y639L/H784A, Y639L/H784A/K378R, P266L/Y639L/H784A or P266L/Y639L/H784A/K378R, are ARC2118 (SEQ ID NO 3), ARC2119 (SEQ ID NO 4), and
ARC3428
GGGAGACAAGAATAAAGCGAGTT-

NNNNNNNNNNNNNNNNNNNNNNNNNNNNNNAAGAGTCGATGA TGCT-
TAGCTAG (SEQ ID NO 137).

In addition, the presence of 2'-OH GTP has historically been an important factor in obtaining transcripts incorporating modified nucleotides. Transcription can be divided into two phases: the first phase is initiation, during which an NTP is added to the 3'-end of GTP (or another substituted guanosine) to yield a dinucleotide which is then extended by about 10-12 nucleotides; the second phase is elongation, during which transcription proceeds beyond the addition of the first about 10-12 nucleotides. It was previously found that small amounts of 2'-OH GTP added to a transcription mixture containing Y639F/K378R mutant or Y639F/H784A/K378R mutant T7 RNA polymerase and an excess of 2'-OMe GTP was sufficient to enable the polymerase to initiate transcription using 2'-OH GTP (and gave a higher yield of 2'-OMe containing transcript than without 2'-OH GTP), but once transcription enters the elongation phase the reduced discrimination between 2'-OMe and 2'-OH GTP, and the excess of 2'-OMe GTP over 2'-OH GTP allows the incorporation of principally the 2'-OMe GTP.

The present invention provides mutant T7 RNA polymerases, e.g Y639L/H784A, Y639L/H784A/K378R, P266L/Y639L/H784A or P266L/Y639L/H784A/K378R which do not require 2'-OH GTP in the transcription mixture for a high yield of 2'-OMe transcription. In one embodiment, high yield means on average at least one transcript per input transcription template.

Another factor in the incorporation of 2'-OMe substituted nucleotides into transcripts is the use of both divalent magnesium and manganese ($Mn^{2+}$) in the transcription mixture. Different combinations of concentrations of magnesium chloride and manganese chloride have been found to affect yields of 2'-O-methylated transcripts, the optimum concentration of the magnesium and manganese chloride being dependent on the concentration in the transcription reaction mixture of NTPs which complex divalent metal ions. To obtain the greatest yields of all 2'-O-methylated transcripts (i.e., all 2'-OMe A, C, U and G nucleotides), concentrations of approximately 5 mM magnesium chloride and 1.5 mM manganese chloride are preferred when each NTP is present at a concentration of 0.5 mM. When the concentration of each NTP is 1.0 mM, concentrations of approximately 6.5 mM magnesium chloride and 2.0 mM manganese chloride are preferred. When each NTP is present at a concentration of 1.5 mM, concentrations of approximately 8 mM magnesium chloride and 2.5 mM manganese chloride are preferred. When the concentration of each NTP is 2.0 mM, concentrations of approximately 9.5 mM magnesium chloride and 3.0 mM manganese chloride are preferred. In any case, departures from these concentrations of up to two-fold still give significant amounts of modified transcripts.

Priming transcription with 2'-OH GMP, guanosine, or other 2'-OH guanosines substituted at a position other than the 2'-OH sugar position is also important for transcription mixtures which do not contain 2'-OH GTP. This effect results from the specificity of the polymerase for the initiating nucleotide. As a result, the 5'-terminal nucleotide of any transcript generated in this fashion is likely to be 2'-OH G. A preferred concentration of GMP (or guanosine) is 0.5 mM and even more preferably 1 mM. It has also been found that including PEG, preferably PEG-8000, in the transcription reaction is useful to maximize incorporation of modified nucleotides.

For maximum incorporation of 2'-OMe ATP (100%), 2'-OMe UTP (100%), 2'-OMe CTP (100%) and 2'-OMe GTP (100%) ("MNA") into transcripts the following conditions may be used: HEPES buffer 200 mM, DTT 40 mM, spermidine 2 mM, PEG-8000 10% (w/v), Triton X-100 0.01% (w/v), $MgCl_2$ 8 mM, $MnCl_2$ 2.5 mM, 2'-OMe NTP (each) 1.5 mM, 2'-OH GMP 1 mM, pH 7.5, Y639L/H784A/K378R mutant T7 RNA Polymerase 200 nM, inorganic pyrophosphatase 5 units/ml, and a DNA template. In some embodiments, the DNA template may be present in a concentration of preferably about 5 to 500 nM. Optionally, the DNA template used with the above transcription conditions comprises an all purine leader sequence that increases the transcription yield relative to a template that does not comprise such a leader sequence when both templates are transcribed under identical conditions. In another embodiment, the leader sequence is a mixture of purines and pyrimidines that increases the transcription yield relative to a template that does not comprise such a leader sequence when both are transcribed under identical conditions. As used herein, one unit of inorganic pyrophosphatase is defined as the amount of enzyme that will liberate 1.0 mole of inorganic orthophosphate per minute at pH 7.2 and 25° C. The reaction may be carried out from about 1 to 24 hours.

In each case, the transcription products can then be used for input into the SELEX™ process to identify aptamers and/or to determine a conserved sequence that has binding specificity to a given target. The resulting sequences are already stabilized, eliminating this step from the post-SELEX™ modification process and giving a more highly stabilized aptamer as a result.

As described below, useful yields of transcripts fully incorporating 2' substituted nucleotides can be obtained under conditions other than the conditions described above. For example, variations to the above transcription conditions include:

The HEPES buffer concentration can range from 0 to 1 M. The present invention also contemplates the use of other buffering agents having a pKa between 5 and 10 including, for example, Tris-hydroxymethyl-aminomethane.

The DTT concentration can range from 0 to 400 mM. The methods of the present invention also provide for the use of other reducing agents including, for example, mercaptoethanol.

The spermidine and/or spermine concentration can range from 0 to 20 mM.

The PEG-8000 concentration can range from 0 to 50% (w/v). The methods of the present invention also provide for the use of other hydrophilic polymer including, for example, other molecular weight PEG or other polyalkylene glycols.

The Triton X-100 concentration can range from 0 to 0.1% (w/v). The methods of the present invention also provide for the use of other non-ionic detergents including, for example, other detergents, including other Triton-X detergents.

The $MgCl_2$ concentration can range from 0.5 mM to 50 mM. The $MnCl_2$ concentration can range from 0.15 mM to 15 mM. Both $MgCl_2$ and $MnCl_2$ must be present within the ranges described and in a preferred embodiment are present in about a 10 to about 3 ratio of $MgCl_2$:$MnCl_2$, preferably, the ratio is about 3-5:1, more preferably, the ratio is about 3-4:1.

The 2'-OMe NTP concentration (each NTP) can range from 5 μM to 5 mM.

The 2'-OH GTP concentration can range from 0 μM to 300 μM. In a preferred embodiment, transcription occurs in the absence of 2'-OH GTP (0 μM).

The concentration of 2'-OH GMP, guanosine or other 2'-OH G substituted at a position other than the 2'sugar position, can range from 0 to 5 mM. Where 2'-OH GTP is not included in the reaction 2'-OH GMP is required and may range from 5 nM to 5 μM.

The DNA template concentration can range from 5 nM to 5 μM.

The mutant polymerase concentration can range from 2 nM to 20 μM.

The inorganic pyrophosphatase can range from 0 to 100 units/ml.

The pH can range from pH 6 to pH 9. The methods of the present invention can be practiced within the pH range of activity of most polymerases that incorporate modified nucleotides.

The transcription reaction may be allowed to occur from about one hour to weeks, preferably from about 1 to about 24 hours.

In addition, the methods of the present invention provide for the optional use of chelating agents in the transcription reaction condition including, for example, EDTA, EGTA, and DTT.

Terminal Region SELEX™ Method

A method for the discovery of nucleic acid transcription template sequences that in some embodiments are used to program a template-directed nucleotide triphosphate polymerization will increase the transcript yield, is a variant of the SELEX™ method known as the Terminal Region SELEX™ method (TR-SELEX™ method). The present invention provides a method for identifying nucleic acid transcription template component sequences, e.g. leader sequences, the use of which increases transcript yield, particularly the yield of transcripts containing 2'-modified nucleotides (e.g., 2'-OMe nucleotides), when used to program a template-directed polymerization, using the TR-SELEX™ method.

To select for leader sequences which promote an increased yield of transcripts containing 2'-modified nucleotides, a candidate library of oligonucleotide transcription templates is generated which contains a promoter sequence which allows for transcription in a template dependent manner, a first fixed region comprising greater than one fixed nucleotide immediately 3' to the promoter to allow for splinted ligations to occur, thereby permitting amplification by the extension of primers bound to primer binding sites on the ligated template; a degenerate region from which the leader sequence will be selected; and a fixed sequence at the 3' terminus to allow for amplification. In a preferred embodiment, the degenerate region of the library template is close to the 5'-terminus thereby reducing the length of the 5' fixed sequence.

Figure 2:
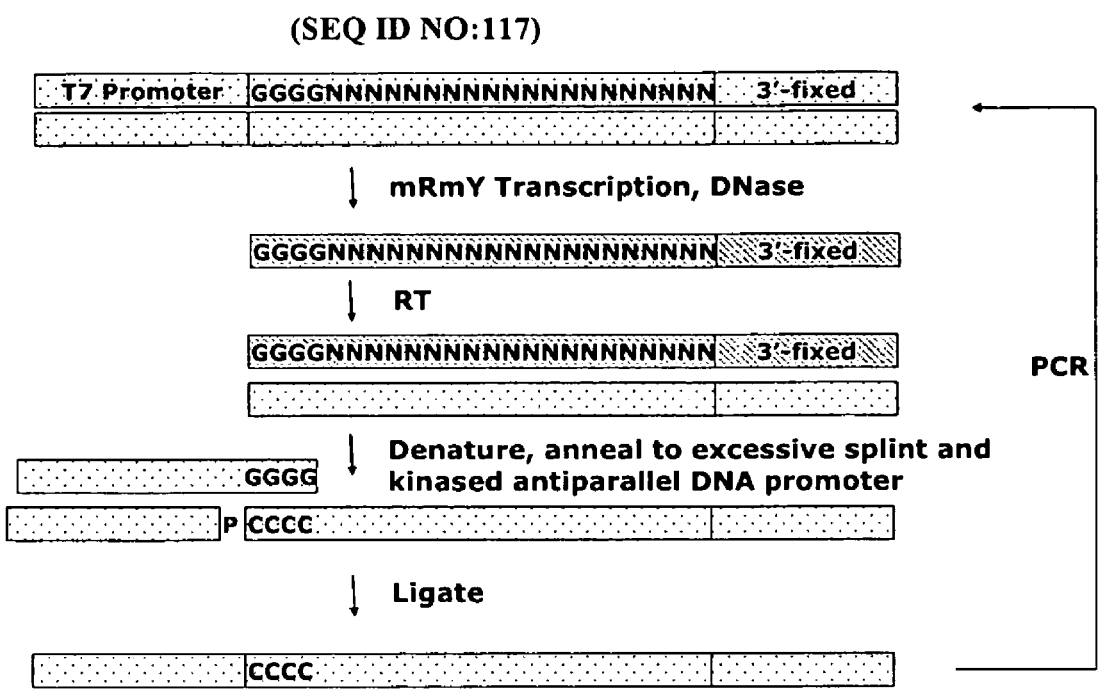
FIG. 2 shows a flow diagram of a Terminal Region SELEX™ (TR-SELEX™) method.

This library of transcription templates is optionally PCR amplified, and then used to program transcription using a transcription reaction mixture comprising a polymerase, (including without limitation, a mutated T7 RNA polymerase), nucleotide triphosphates (NTPs) (including without limitation one or more 2'-modified NTPs), and magnesium ions, under conditions disclosed herein. The resulting transcript mixture is reverse transcribed to obtain a candidate mixture of cDNA sequences which are then ligated to a DNA sequence encoding the T7 promoter. Optionally, the resulting transcript mixture first undergoes ligation, and is then reverse transcribed. The cDNA which encodes the transcripts are then amplified by PCR, and clones are assayed for transcription yield using gel analysis. Transcription templates amplified in this manner can optionally be used to perform further rounds of the TR-SELEX™ process if necessary to achieve greater transcript yield (See FIG. 2).

Clone sequences of the amplified transcripts can be analyzed to identify the 5'-leader sequence element which allows for transcription (including without limitation transcription incorporating one or more 2'-modified nucleotides). These 5' leader sequence elements are useful for designing candidate libraries of oligonucleotide transcription templates which may be used in SELEX™ to promote an increased yield of nucleic acid transcripts which contain 2'-modified nucleotides. Examples of preferred libraries of DNA transcription templates which incorporate 5'-leader sequence elements identified by the TR-SELEX™ method (shown underlined) and promote higher yields of transcripts containing 2'-modified nucleotides, e.g., 2'-OMe nucleotides, using the conditions disclosed herein are described below.

For each of the sequences of the libraries of DNA transcription templates listed below, the 5'-leader sequence element is shown underlined, and all sequences are in the 5'-3' direction.

```
ARC 2118 (SEQ ID NO 3)
TAATACGACTCACTATAGGGGAGTACAATAACGTTCTCGNNNNNNNNNNNN

NNNNNNNNNNNNNNNNNNNGGATCGTTACGACTAGCATCGATG

ARC2119 (SEQ ID NO 4)
TAATACGACTCACTATAGGGGGTGATATTGACGTTCTCGNNNNNNNNNNNN

NNNNNNNNNNNNNNNNNNNGGATCGTTACGACTAGCATCGATG

ARC2120 (SEQ ID NO 5)
TAATACGACTCACTATAGGGGTGCGCGGTTACGTTCTCGNNNNNNNNNNNN

NNNNNNNNNNNNNNNNNNNGGATCGTTACGACTAGCATCGATG

ARC2121 (SEQ ID NO 6)
TAATACGACTCACTATAGGGGGAGGGGTGCCGTTCTCGNNNNNNNNNNNN

NNNNNNNNNNNNNNNNNNNGGATCGTTACGACTAGCATCGATG
```

To generate transcript mixtures of 2'-modified (e.g., 2'-OMe) RNA transcripts under conditions in which a polymerase accepts 2'-modified NTPs, the Y639F, Y639F/K378R, Y639F/H784A, Y639F/H784A/K378R, Y639L/H784A, Y639L/H784A/K378R, P266L/Y639L/H784A) or P266L/Y639L/H784A/K378R) mutant T7 RNA polymerase can be used with the 5'-leader sequences identified by the methods provided by the present invention. A preferred polymerase to be used with the 5' leader sequences of the present invention, giving the highest yield of nucleic acid transcripts containing 2'-modified nucleotides, is the Y639L/H784A mutant RNA polymerase previously described. Another preferred polymerase to be used with the 5'-leader sequences of the invention is the Y639L/H784A/K378R mutant T7 RNA polymerase. Other T7 RNA polymerases, particularly those that exhibit a high tolerance for bulky 2'-substituents, may also be used in the present invention.

In addition to incorporating leader sequences in candidate libraries and mutant polymerases which promote increased yields of nucleic acid transcripts containing 2'-modified nucleotides (e.g., Y639L/H784A and Y639L/H784A/K378R mutant T7 RNA polymerases), the numerous factors described above which have been determined to be important for the transcription conditions can be used to further increase the yield of transcripts containing 2'-modified nucleotides.

The identified leader sequences and the Y639F/H784A, Y639F/H784A/K378R, Y639L, Y639L/K378R, Y639L/H874A, Y639L/H874A/K378R, P266L/Y639L/H784A or P266L/Y639L/H784A/K378R mutant T7 RNA polymerases, can be used in SELEX™ with the conditions described herein to generate aptamers comprising any combination of 2'-modified nucleotides, e.g., 2'-OH, 2'-F, 2'-deoxy, 2'-OMe, and 2'-NH$_2$ modifications of the ATP, GTP, CTP, TTP, and UTP nucleotides. The 2'-modified nucleotides incorporated are preferably 2'-O-methyl nucleotides. An aptamer composition comprising one or more 2'-O-methyl nucleotides is preferred. An aptamer composition comprising 100% 2'-O-methyl purines and pyrimidines, except for the starting nucleotide, is more preferred. In one preferred embodiment, one of the identified leader sequences and the Y639L/H874A, Y639L/H784A/K378R, P266L/Y639L/H784A or P266L/Y639L/H784A/K378R mutant T7 RNA polymerases are used in the SELEX™ method with the conditions described herein to generate higher transcript yields of aptamers comprising fully 2'-OMe nucleotides.

For maximum incorporation of 2'-OMe ATP (100%), UTP (100%), CTP (100%) and GTP (100%) (MNA") into transcripts the following conditions are preferred: HEPES buffer 200 mM, DTT 40 mM, spermidine 2 mM, PEG-8000 10% (w/v), Triton X-100 0.01% (w/v), MgCl$_2$ 8 mM, MnCl$_2$ 2.5 mM, 2'-OMe NTP (each) 1.5 mM, 2'-OH GMP 1 mM, pH 7.5, Y639L/H784A/K378R T7 RNA Polymerase 200 nM, inorganic pyrophosphatase 5 units/ml, and a leader sequence that increases the transcription yield under the derived transcription conditions. In one embodiment, the leader sequence is an all purine leader sequence. In another embodiment, the leader sequence is a mixture of purines and pyrimidines. As used herein, one unit of inorganic pyrophosphatase is defined as the amount of enzyme that will liberate 1.0 mole of inorganic orthophosphate per minute at pH 7.2 and 25° C.

Aptamer Medicinal Chemistry

Once aptamers that bind to a desired target are identified, several techniques may be optionally performed to further increase binding and/or functional characteristics of the identified aptamer sequences. Aptamers, e.g. MNA aptamers, that bind to a desired target identified through the SELEX™ process, (e.g. the 2'-Modified SELEX™ method) may be optionally truncated to obtain the minimal aptamer sequence (also referred to herein as "minimized construct") having the desired binding and/or functional characteristics. One method of accomplishing this is by using folding programs and sequence analysis (e.g., aligning clone sequences resulting from a selection to look for conserved motifs and/or covariation) to inform the design of minimized constructs. Biochemical probing experiments can also be performed to determine the 5' and 3' boundaries of an aptamer sequence to inform the design of minimized constructs. Minimized constructs can then be chemically synthesized and tested for binding and functional characteristics as compared to the non-minized sequence from which they were derived. Variants of an aptamer sequence containing a series of 5', 3' and/or internal deletions may also be directly chemically synthesized and tested for binding and/or functional characteristics as compared to the non-minimized aptamer sequence from which they were derived.

Additionally, doped reselections may be used to explore the sequence requirements within a single active aptamer sequence such as an MNA aptamer (i.e., an aptamer that binds to a desired target identified through the SELEX™ process, (including 2'-Modified SELEX™ process), or a single minimized aptamer sequence. Doped reselections are carried out using a synthetic, degenerate pool that has been designed based on the single sequence of interest. The level of degeneracy usually varies 70% to 85% from the wild type nucleotide, i.e., the single sequence of interest. In general, sequences with neutral mutations are identified through the doped reselection process, but in some cases sequence changes can result in improvements in affinity. The composite sequence information from clones identified using doped reselections can then be used to identify the minimal binding motif and aid in Medicinal Chemistry efforts.

Aptamer sequences identified using the SELEX™ process such as MNA aptamers (including the 2'-Modified SELEX™ process and doped reselections) and/or minimized aptamer sequences may also be optionally modified post-SELEX™ selection using Aptamer Medicinal Chemistry to perform random or directed mutagenesis of the sequence to increase binding affinity and/or functional characteristics, or alternatively to determine which positions in the sequence are essential for binding activity and/or functional characteristics.

Aptamer Medicinal Chemistry is an aptamer improvement technique in which sets of variant aptamers are chemically synthesized. These sets of variants typically differ from the parent aptamer by the introduction of a single substituent, and differ from each other by the location of this substituent. These variants are then compared to each other and to the parent. Improvements in characteristics may be profound enough that the inclusion of a single substituent may be all that is necessary to achieve a particular therapeutic criterion.

Alternatively the information gleaned from the set of single variants may be used to design further sets of variants in which more than one substituent is introduced simultaneously. In one design strategy, all of the single substituent variants are ranked, the top 4 are chosen and all possible double (6), triple (4) and quadruple (1) combinations of these 4 single substituent variants are synthesized and assayed. In a second design strategy, the best single substituent variant is considered to be the new parent and all possible double substituent variants that include this highest-ranked single substituent variant are synthesized and assayed. Other strategies may be used, and these strategies may be applied repeatedly such that the number of substituents is gradually increased while continuing to identify further-improved variants.

Aptamer Medicinal Chemistry may be used particularly as a method to explore the local, rather than the global, introduction of substituents. Because aptamers are discovered within libraries that are generated by transcription, any substituents that are introduced during the SELEX™ process must be introduced globally. For example, if it is desired to introduce phosphorothioate linkages between nucleotides then they can only be introduced at every A (or every G, C, T, U etc.) (globally substituted). Aptamers which require phosphorothioates at some As (or some G, C, T, U etc.) (locally substituted) but cannot tolerate it at other As cannot be readily discovered by this process.

The kinds of substituent that can be utilized by the Aptamer Medicinal Chemistry process are only limited by the ability to generate them as solid-phase synthesis reagents and introduce them into an oligomer synthesis scheme. The process is certainly not limited to nucleotides alone. Aptamer Medicinal Chemistry schemes may include substituents that introduce steric bulk, hydrophobicity, hydrophilicity, lipophilicity, lipophobicity, positive charge, negative charge, neutral charge, zwitterions, polarizability, nuclease-resistance, conformational rigidity, conformational flexibility, protein-binding characteristics, mass etc. Aptamer Medicinal Chemistry schemes may include base-modifications, sugar-modifications or phosphodiester linkage-modifications.

When considering the kinds of substituents that are likely to be beneficial within the context of a therapeutic aptamer, it may be desirable to introduce substitutions that fall into one or more of the following categories:
(1) Substituents already present in the body, e.g., 2'-deoxy, 2'-ribo, 2'-O-methyl purines or pyrimidines or 5-methyl cytosine.
(2) Substituents already part of an approved therapeutic, e.g., phosphorothioate-linked oligonucleotides.
(3) Substituents that hydrolyze or degrade to one of the above two categories, e.g., methylphosphonate-linked oligonucleotides.
(4) The aptamers of the present invention include aptamers developed through aptamer medicinal chemistry as described herein.

Target binding affinity of the aptamers of the present invention can be assessed through a series of binding reactions between the aptamer and target (e.g., a protein) in which trace $^{32}$P-labeled aptamer is incubated with a dilution series of the target in a buffered medium then analyzed by nitrocellulose filtration using a vacuum filtration manifold. Referred to herein as the dot blot binding assay, this method uses a three layer filtration medium consisting (from top to bottom) of nitrocellulose, nylon filter, and gel blot paper. RNA that is bound to the target is captured on the nitrocellulose filter whereas the non-target bound RNA is captured on the nylon filter. The gel blot paper is included as a supporting medium for the other filters. Following filtration, the filter layers are separated, dried and exposed on a phosphor screen and quantified using a phosphorimaging system from which. The quantified results can be used to generate aptamer binding curves from which dissociation constants ($K_D$) can be calculated. In a preferred embodiment, the buffered medium used to perform the binding reactions is 1× Dulbecco's PBS (with $Ca^{++}$ and $Mg^{++}$) plus 0.1 mg/mL BSA.

Generally, the ability of an aptamer to modulate the functional activity of a target, i.e., the functional activity of the aptamer, can be assessed using in vitro and in vivo models, which will vary depending on the biological function of the target. In some embodiments, the aptamers of the present invention may inhibit a known biological function of the target, while in other embodiments the aptamers of the invention may stimulate a known biological function of the target. The functional activity of aptamers of the present invention can be assessed using in vitro and in vivo models designed to measure a known function of the aptamer target.

The aptamers of the present invention may be routinely adapted for diagnostic purposes according to any number of techniques employed by those skilled in the art. Diagnostic utilization may include both in vivo or in vitro diagnostic applications. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any aptamer by procedures known in the art to incorporate a labeling tag in order to track the presence of such ligand. Such a tag could be used in a number of diagnostic procedures.

Apatamers Having Immunostimulatory Motifs

Recognition of bacterial DNA by the vertebrate immune system is based on the recognition of unmethylated CG dinucleotides in particular sequence contexts ("CpG motifs"). One receptor that recognizes such a motif is Toll-like receptor 9 ("TLR 9"), a member of a family of Toll-like receptors (~10 members) that participate in the innate immune response by recognizing distinct microbial components. TLR 9 binds unmethylated oligodeoxynucleotide ("ODN") CpG sequences in a sequence-specific manner. The recognition of CpG motifs triggers defense mechanisms leading to innate and ultimately acquired immune responses. For example, activation of TLR 9 in mice induces activation of antigen presenting cells, up regulation of MHC class I and II molecules and expression of important co-stimulatory molecules and cytokines including IL-12 and IL-23. This activation both directly and indirectly enhances B and T cell responses, including robust up regulation of the TH1 cytokine IFN-gamma. Collectively, the response to CpG sequences leads to: protection against infectious diseases, improved immune response to vaccines, an effective response against asthma, and improved antibody-dependent cell-mediated cytotoxicity. Thus, CpG ODNs can provide protection against infectious diseases, function as immuno-adjuvants or cancer therapeutics (monotherapy or in combination with a mAb or other therapies), and can decrease asthma and allergic response.

Aptamers of the present invention, e.g. MNA aptamers, may comprise one or more CpG or other immunostimulatory sequence. Such aptamers can be identified or generated by a variety of strategies using, e.g., the SELEX™ process described herein. In general the strategies can be divided into two groups. In group one, the strategies are directed to identifying or generating aptamers comprising both a CpG motif or other immunostimulatory sequence as well as a binding site for a target, where the target (hereinafter "non-CpG target") is a target other than one known to recognize CpG motifs or other immunostimulatory sequences and known to stimulates an immune response upon binding to a CpG motif. The first strategy of this group comprises performing SELEX™ to obtain an aptamer to a specific non-CpG target, using an oligonucleotide pool wherein a CpG motif has been incorporated into each member of the pool as, or as part of, a fixed region, e.g., in some embodiments the randomized region of the pool members comprises a fixed region having a CpG motif incorporated therein, and identifying an aptamer comprising a CpG motif. The second strategy of this group comprises performing SELEX™ to obtain an aptamer to a specific non-CpG target preferably a target and following selection appending a CpG motif to the 5' and/or 3' end or engineering a CpG motif into a region, preferably a non-essential region, of the aptamer. The third strategy of this group comprises performing SELEX™ to obtain an aptamer to a specific non-CpG target, wherein during synthesis of the pool the molar ratio of the various nucleotides is biased in one or more nucleotide addition steps so that the randomized region of each member of the pool is enriched in CpG motifs, and identifying an aptamer comprising a CpG motif. The fourth strategy of this group comprises performing SELEX™ to obtain an aptamer to a specific non-CpG target, and identifying an aptamer comprising a CpG motif. The fifth strategy of this group comprises performing SELEX™ to obtain an aptamer to a specific non-CpG target and identifying an aptamer which, upon binding, stimulates an immune response but which does not comprise a CpG motif.

In group two, the strategies are directed to identifying or generating aptamers comprising a CpG motif and/or other sequences that are bound by the receptors for the CpG motifs (e.g., TLR9 or the other toll-like receptors) and upon binding stimulate an immune response. The first strategy of this group comprises performing SELEX™ to obtain an aptamer to a target known to bind to CpG motifs or other immunostimulatory sequences and upon binding stimulate an immune response using an oligonucleotide pool wherein a CpG motif has been incorporated into each member of the pool as, or as part of, a fixed region, e.g., in some embodiments the randomized region of the pool members comprise a fixed region having a CpG motif incorporated therein, and identifying an aptamer comprising a CpG motif. The second strategy of this group comprises performing SELEX™ to obtain an aptamer to a target known to bind to CpG motifs or other immunostimulatory sequences and upon binding stimulate an immune response and then appending a CpG motif to the 5' and/or 3' end or engineering a CpG motif into a region, preferably a non-essential region, of the aptamer. The third strategy of this group comprises performing SELEX™ to obtain an aptamer to a target known to bind to CpG motifs or other immunostimulatory sequences and upon binding stimulate an immune response wherein during synthesis of the pool, the molar ratio of the various nucleotides is biased in one or more nucleotide addition steps so that the randomized region of each member of the pool is enriched in CpG motifs, and identifying an aptamer comprising a CpG motif. The fourth strategy of this group comprises performing SELEX™ to obtain an aptamer to a target known to bind to CpG motifs or other immunostimulaory sequences and upon binding stimulate an immune response and identifying an aptamer comprising a CpG motif. The fifth strategy of this group comprises performing SELEX™ to obtain an aptamer to a target known to bind to CpG motifs or other immunostimulatory sequences, and identifying an aptamer which upon binding, stimulate an immune response but which does not comprise a CpG motif.

A variety of different classes of CpG motifs have been identified, each resulting upon recognition in a different cascade of events, release of cytokines and other molecules, and activation of certain cell types. See, e.g., CpG Motifs in Bacterial DNA and Their Immune Effects, Annu. Rev. Immunol. 2002, 20:709-760, incorporated herein by reference. Additional immunostimulatory motifs are disclosed in the following U.S. Patents, each of which is incorporated herein by reference: U.S. Pat. No. 6,207,646; U.S. Pat. No. 6,239,116; U.S. Pat. No. 6,429,199; U.S. Pat. No. 6,214,806; U.S. Pat. No. 6,653,292; U.S. Pat. No. 6,426,434; U.S. Pat. No. 6,514,948 and U.S. Pat. No. 6,498,148. Any of these CpG or other immunostimulatory motifs can be incorporated into an aptamer. The choice of aptamers is dependent on the disease or disorder to be treated. Preferred immunostimulatory motifs are as follows (shown 5' to 3' left to right) wherein "r" designates a purine, "y" designates a pyrimidine, and "X" designates any nucleotide: AACGTTCGAG (SEQ ID NO:136); AACGTT; ACGT, rCGy; rrCGyy, XCGX, XXCGXX, and $X_1X_2CGY_1Y_2$ wherein $X_1$ is G or A, $X_2$ is not C, $Y_1$ is not G and $Y_2$ is preferably T.

In those instances where a CpG motif is incorporated into an aptamer that binds to a specific target other than a target known to bind to CpG motifs and upon binding stimulate an immune response (a "non-CpG target"), the CpG is preferably located in a non-essential region of the aptamer. Non-essential regions of aptamers can be identified by site-directed mutagenesis, deletion analyses and/or substitution analyses. However, any location that does not significantly interfere with the ability of the aptamer to bind to the non-CpG target may be used. In addition to being embedded within the aptamer sequence, the CpG motif may be appended to either or both of the 5' and 3' ends or otherwise attached to the aptamer. Any location or means of attachment may be used so long as the ability of the aptamer to bind to the non-CpG target is not significantly interfered with.

As used herein, "stimulation of an immune response" can mean either (1) the induction of a specific response (e.g., induction of a Th1 response) or of the production of certain molecules or (2) the inhibition or suppression of a specific response (e.g., inhibition or suppression of the Th2 response) or of certain molecules.

Modulation of Pharmacokinetics and Biodistribution of Aptamer Therapeutics

It is important that the pharmacokinetic properties for all oligonucleotide-based therapeutics, including aptamers, be tailored to match the desired pharmaceutical application. While aptamers directed against extracellular targets do not suffer from difficulties associated with intracellular delivery (as is the case with antisense and RNAi-based therapeutics), such aptamers must still be able to be distributed to target organs and tissues, and remain in the body (unmodified) for a period of time consistent with the desired dosing regimen.

Thus, the present invention provides materials and methods to affect the pharmacokinetics of aptamer compositions, and, in particular, the ability to tune aptamer pharmacokinetics. The tunability of (i.e., the ability to modulate) aptamer pharmacokinetics is achieved through conjugation of modifying moieties (e.g., PEG polymers) to the aptamer and/or the incorporation of modified nucleotides (e.g., 2'-fluoro or 2'-O-methyl) to alter the chemical composition of the nucleic acid. The ability to tune aptamer pharmacokinetics is used in the improvement of existing therapeutic applications, or alternatively, in the development of new therapeutic applications. For example, in some therapeutic applications, e.g., in anti-neoplastic or acute care settings where rapid drug clearance or turn-off may be desired, it is desirable to decrease the residence times of aptamers in the circulation. Alternatively, in other therapeutic applications, e.g., maintenance therapies where systemic circulation of a therapeutic is desired, it may be desirable to increase the residence times of aptamers in circulation.

In addition, the tunability of aptamer pharmacokinetics is used to modify the biodistribution of an aptamer therapeutic in a subject. For example, in some therapeutic applications, it may be desirable to alter the biodistribution of an aptamer therapeutic in an effort to target a particular type of tissue or a specific organ (or set of organs). In these applications, the aptamer therapeutic preferentially accumulates in a specific tissue or organ(s). In other therapeutic applications, it may be desirable to target tissues displaying a cellular marker or a symptom associated with a given disease, cellular injury or other abnormal pathology, such that the aptamer therapeutic preferentially accumulates in the affected tissue. For example, as described in the provisional application U.S. Ser. No. 60/550,790, filed on Mar. 5, 2004, and entitled "Controlled Modulation of the Pharmacokinetics and Biodistribution of Aptamer Therapeutics", and in the non-provisional application U.S. Ser. No. 11/075,648, filed on Mar. 7, 2005, and entitled "Controlled Modulation of the Pharmacokinetics and Biodistribution of Aptamer Therapeutics", PEGylation of an aptamer therapeutic (e.g., PEGylation with a 20 kDa PEG polymer) is used to target inflamed tissues, such that the PEGylated aptamer therapeutic preferentially accumulates in inflamed tissue.

To determine the pharmacokinetic and biodistribution profiles of aptamer therapeutics (e.g., aptamer conjugates or aptamers having altered chemistries, such as modified nucleotides) a variety of parameters are monitored. Such parameters include, for example, the half-life ($t_{1/2}$), the plasma clearance (Cl), the volume of distribution (Vss), the area under the concentration-time curve (AUC), maximum observed serum or plasma concentration ($C_{max}$), and the mean residence time (MRT) of an aptamer composition. As used herein, the term "AUC" refers to the area under the plot of the plasma concentration of an aptamer therapeutic versus the time after aptamer administration. The AUC value is used to estimate the bioavailability (i.e., the percentage of administered aptamer therapeutic in the circulation after aptamer administration) and/or total clearance (Cl) (i.e., the rate at which the aptamer therapeutic is removed from circulation) of a given aptamer therapeutic. The volume of distribution relates the plasma concentration of an aptamer therapeutic to the amount of aptamer present in the body. The larger the Vss, the more an aptamer is found outside of the plasma (i.e., the more extravasation).

The present invention provides materials and methods to modulate, in a controlled manner, the pharmacokinetics and biodistribution of stabilized aptamer compositions, e.g. MNA aptamers, in vivo by conjugating an aptamer, e.g. an MNA aptamer, to a modulating moiety such as a small molecule, peptide, or polymer terminal group, or by incorporating modified nucleotides into an aptamer. As described herein, conjugation of a modifying moiety and/or altering nucleotide(s) chemical composition alters fundamental aspects of aptamer residence time in circulation and distribution to tissues.

In addition to clearance by nucleases, oligonucleotide therapeutics are subject to elimination via renal filtration. As such, a nuclease-resistant oligonucleotide administered intravenously typically exhibits an in vivo half-life of <10 min, unless filtration can be blocked. This can be accomplished by either facilitating rapid distribution out of the blood stream into tissues or by increasing the apparent molecular weight of the oligonucleotide above the effective size cut-off for the glomerulus. Conjugation of small therapeutics to a PEG polymer (PEGylation), described below, can dramatically lengthen residence times of aptamers in circulation, thereby decreasing dosing frequency and enhancing effectiveness against vascular targets.

Aptamers can be conjugated to a variety of modifying moieties, such as high molecular weight polymers, e.g., PEG; peptides, e.g., Tat (a 13-amino acid fragment of the HIV Tat protein (Vives, et al. (1997), J. Biol. Chem. 272(25): 16010-7)), Ant (a 16-amino acid sequence derived from the third helix of the *Drosophila* antennapedia homeotic protein (Pietersz, et al. (2001), Vaccine 19(11-12): 1397-405)) and Arg7 (a short, positively charged cell-permeating peptides composed of polyarginine ($Arg_7$) (Rothbard, et al. (2000), Nat. Med. 6(11): 1253-7; Rothbard, J et al. (2002), J. Med. Chem. 45(17): 3612-8)); and small molecules, e.g., lipophilic compounds such as cholesterol. Among the various conjugates described herein, in vivo properties of aptamers are altered most profoundly by complexation with PEG groups. For example, complexation of a mixed 2'F and 2'-OMe modified aptamer therapeutic with a 20 kDa PEG polymer hinders renal filtration and promotes aptamer distribution to both healthy and inflamed tissues. Furthermore, the 20 kDa PEG polymer-aptamer conjugate proves nearly as effective as a 40 kDa PEG polymer in preventing renal filtration of aptamers. While one effect of PEGylation is on aptamer clearance, the prolonged systemic exposure afforded by presence of the 20 kDa moiety also facilitates distribution of aptamer to tissues, particularly those of highly perfused organs and those at the site of inflammation. The aptamer-20 kDa PEG polymer conjugate directs aptamer distribution to the site of inflammation, such that the PEGylated aptamer preferentially accumulates in inflamed tissue. In some instances, the 20 kDa PEGylated aptamer conjugate is able to access the interior of cells, such as, for example, kidney cells.

Modified nucleotides can also be used to modulate the plasma clearance of aptamers. For example, an unconjugated aptamer which incorporates both 2'-F and 2'-OMe stabilizing chemistries, which is typical of current generation aptamers as it exhibits a high degree of nuclease stability in vitro and in vivo, displays rapid loss from plasma (i.e., rapid plasma clearance) and a rapid distribution into tissues, primarily into the kidney, when compared to unmodified aptamer.

Peg-Derivatized Nucleic Acids

As described above, derivatization of nucleic acids with high molecular weight non-immunogenic polymers has the potential to alter the pharmacokinetic and pharmacodynamic properties of nucleic acids making them more effective therapeutic agents. Favorable changes in activity can include increased resistance to degradation by nucleases, decreased filtration through the kidneys, decreased exposure to the immune system, and altered distribution of the therapeutic through the body.

The aptamer compositions of the invention may be derivatized with polyalkylene glycol ("PAG") moieties. Examples of PAG-derivatized nucleic acids are found in U.S. patent application Ser. No. 10/718,833, filed on Nov. 21, 2003, which is herein incorporated by reference in its entirety. Typical polymers used in the invention include polyethylene glycol ("PEG"), also known as polyethylene oxide ("PEO") and polypropylene glycol (including poly isopropylene glycol). Additionally, random or block copolymers of different alkylene oxides (e.g., ethylene oxide and propylene oxide) can be used in many applications. In its most common form, a polyalkylene glycol, such as PEG, is a linear polymer terminated at each end with hydroxyl groups: HO—$CH_2CH_2O$—($CH_2CH_2O)_n$—$CH_2CH_2$—OH. This polymer, alpha-, omega-dihydroxylpolyethylene glycol, can also be represented as HO-PEG-OH, where it is understood that the -PEG- symbol represents the following structural unit: —$CH_2CH_2O$—($CH_2CH_2O)_n$—$CH_2CH_2$— where n typically ranges from about 4 to about 10,000.

As shown, the PEG molecule is di-functional and is sometimes referred to as "PEG diol." The terminal portions of the PEG molecule are relatively non-reactive hydroxyl moieties, the —OH groups, that can be activated, or converted to functional moieties, for attachment of the PEG to other compounds at reactive sites on the compound. Such activated PEG diols are referred to herein as bi-activated PEGs. For example, the terminal moieties of PEG diol have been functionalized as active carbonate ester for selective reaction with amino moieties by substitution of the relatively non-reactive hydroxyl moieties, —OH, with succinimidyl active ester moieties from N-hydroxy succinimide.

In many applications, it is desirable to cap the PEG molecule on one end with an essentially non-reactive moiety so that the PEG molecule is mono-functional (or mono-activated). In the case of protein therapeutics which generally display multiple reaction sites for activated PEGs, bi-functional activated PEGs lead to extensive cross-linking, yielding poorly functional aggregates. To generate mono-activated PEGs, one hydroxyl moiety on the terminus of the PEG diol molecule typically is substituted with non-reactive methoxy end moiety, —$OCH_3$. The other, un-capped terminus of the PEG molecule typically is converted to a reactive end moiety that can be activated for attachment at a reactive site on a surface or a molecule such as a protein.

PAGs are polymers which typically have the properties of solubility in water and in many organic solvents, lack of toxicity, and lack of immunogenicity. One use of PAGs is to covalently attach the polymer to insoluble molecules to make the resulting PAG-molecule "conjugate" soluble. For example, it has been shown that the water-insoluble drug paclitaxel, when coupled to PEG, becomes water-soluble. Greenwald, et al., *J. Org. Chem.*, 60:331-336 (1995). PAG conjugates are often used not only to enhance solubility and stability but also to prolong the blood circulation half-life of molecules.

Polyalkylated compounds of the invention are typically between 5 and 80 kDa in size however any size can be used, the choice dependent on the aptamer and application. Other PAG compounds of the invention are between 10 and 80 kDa in size. Still other PAG compounds of the invention are between 10 and 60 kDa in size. For example, a PAG polymer may be at least 10, 20, 30, 40, 50, 60, or 80 kDa in size. Such polymers can be linear or branched. In some embodiments the polymers are PEG.

In contrast to biologically-expressed protein therapeutics, nucleic acid therapeutics are typically chemically synthesized from activated monomer nucleotides. PEG-nucleic acid conjugates may be prepared by incorporating the PEG using the same iterative monomer synthesis. For example, PEGs activated by conversion to a phosphoramidite form can be incorporated into solid-phase oligonucleotide synthesis. Alternatively, oligonucleotide synthesis can be completed with site-specific incorporation of a reactive PEG attachment site. Most commonly this has been accomplished by addition of a free primary amine at the 5'-terminus (incorporated using a modifier phosphoramidite in the last coupling step of solid phase synthesis). Using this approach, a reactive PEG (e.g., one which is activated so that it will react and form a bond with an amine) is combined with the purified oligonucleotide and the coupling reaction is carried out in solution.

The ability of PEG conjugation to alter the biodistribution of a therapeutic is related to a number of factors including the apparent size (e.g., as measured in terms of hydrodynamic radius) of the conjugate. Larger conjugates (>10 kDa) are known to more effectively block filtration via the kidney and to consequently increase the serum half-life of small macromolecules (e.g., peptides, antisense oligonucleotides). The ability of PEG conjugates to block filtration has been shown to increase with PEG size up to approximately 50 kDa (further increases have minimal beneficial effect as half life becomes defined by macrophage-mediated metabolism rather than elimination via the kidneys).

Production of high molecular weight PEGs (>10 kDa) can be difficult, inefficient, and expensive. As a route towards the synthesis of high molecular weight PEG-nucleic acid conjugates, previous work has been focused towards the generation of higher molecular weight activated PEGs. One method for generating such molecules involves the formation of a branched activated PEG in which two or more PEGs are attached to a central core carrying the activated group. The terminal portions of these higher molecular weight PEG molecules, i.e., the relatively non-reactive hydroxyl (—OH) moieties, can be activated, or converted to functional moieties, for attachment of one or more of the PEGs to other compounds at reactive sites on the compound. Branched activated PEGs will have more than two termini, and in cases where two or more termini have been activated, such activated higher molecular weight PEG molecules are referred to herein as, multi-activated PEGs. In some cases, not all termini in a branch PEG molecule are activated. In cases where any two termini of a branch PEG molecule are activated, such PEG molecules are referred to as bi-activated PEGs. In some cases where only one terminus in a branch PEG molecule is activated, such PEG molecules are referred to as mono-activated. As an example of this approach, activated PEG prepared by the attachment of two monomethoxy PEGs to a lysine core which is subsequently activated for reaction has been described (Harris et al., Nature, vol. 2: 214-221, 2003).

The present invention provides another cost effective route to the synthesis of high molecular weight PEG-nucleic acid (preferably, aptamer) conjugates including multiply PEGylated nucleic acids. The present invention also encompasses PEG-linked multimeric oligonucleotides, e.g., dimerized aptamers. The present invention also relates to high molecular weight compositions where a PEG stabilizing moiety is a linker which separates different portions of an aptamer, e.g., the PEG is conjugated within a single aptamer sequence, such that the linear arrangement of the high molecular weight aptamer composition is, e.g., nucleic acid-PEG-nucleic acid (-PEG-nucleic acid)$_n$ where n is greater than or equal to 1.

High molecular weight compositions of the invention include those having a molecular weight of at least 10 kDa. Compositions typically have a molecular weight between 10 and 80 kDa in size. High molecular weight compositions of the invention are at least 10, 20, 30, 40, 50, 60, or 80 kDa in size.

A stabilizing moiety is a molecule, or portion of a molecule, which improves pharmacokinetic and pharmacodynamic properties of the high molecular weight aptamer compositions of the invention. In some cases, a stabilizing moiety is a molecule or portion of a molecule which brings two or more aptamers, or aptamer domains, into proximity, or provides decreased overall rotational freedom of the high molecular weight aptamer compositions of the invention. A stabilizing moiety can be a polyalkylene glycol, such a polyethylene glycol, which can be linear or branched, a homopolymer or a heteropolymer. Other stabilizing moieties include polymers such as peptide nucleic acids (PNA). Oligonucleotides can also be stabilizing moieties; such oligonucleotides can include modified nucleotides, and/or modified linkages, such as phosphorothioates. A stabilizing moiety can be an integral part of an aptamer composition, i.e., it is covalently bonded to the aptamer.

Compositions of the invention include high molecular weight aptamer compositions in which two or more nucleic acid moieties are covalently conjugated to at least one polyalkylene glycol moiety. The polyalkylene glycol moieties serve as stabilizing moieties. In compositions where a polyalkylene glycol moiety is covalently bound at either end to an aptamer, such that the polyalkylene glycol joins the nucleic acid moieties together in one molecule, the polyalkylene glycol is said to be a linking moiety. In such compositions, the primary structure of the covalent molecule includes the linear arrangement nucleic acid-PAG-nucleic acid. One example is a composition having the primary structure nucleic acid-PEG-nucleic acid. Another example is a linear arrangement of: nucleic acid-PEG-nucleic acid-PEG-nucleic acid.

To produce the nucleic acid-PEG-nucleic acid conjugate, the nucleic acid is originally synthesized such that it bears a single reactive site (e.g., it is mono-activated). In a preferred embodiment, this reactive site is an amino group introduced at the 5'-terminus by addition of a modifier phosphoramidite as the last step in solid phase synthesis of the oligonucleotide. Following deprotection and purification of the modified oligonucleotide, it is reconstituted at high concentration in a solution that minimizes spontaneous hydrolysis of the activated PEG. In a preferred embodiment, the concentration of oligonucleotide is 1 mM and the reconstituted solution contains 200 mM NaHCO$_3$-buffer, pH 8.3. Synthesis of the conjugate is initiated by slow, step-wise addition of highly purified bi-functional PEG. In a preferred embodiment, the PEG diol is activated at both ends (bi-activated) by derivatization with succinimidyl propionate. Following reaction, the PEG-nucleic acid conjugate is purified by gel electrophoresis or liquid chromatography to separate fully-, partially-, and un-conjugated species. Multiple PAG molecules concatenated (e.g., as random or block copolymers) or smaller PAG chains can be linked to achieve various lengths (or molecular weights). Non-PAG linkers can be used between PAG chains of varying lengths.

The 2'-O-methyl, 2'-fluoro and other modified nucleotide modifications stabilize the aptamer against nucleases and increase its half life in vivo. The 3'-3'-dT cap also increases exonuclease resistance. See, e.g., U.S. Pat. Nos. 5,674,685; 5,668,264; 6,207,816; and 6,229,002, each of which is incorporated by reference herein in its entirety.

Pag-Derivatization of a Reactive Nucleic Acid

High molecular weight PAG-nucleic acid-PAG conjugates can be prepared by reaction of a mono-functional activated PEG with a nucleic acid containing more than one reactive site. In one embodiment, the nucleic acid is bi-reactive, or bi-activated, and contains two reactive sites: a 5'-amino group and a 3'-amino group introduced into the oligonucleotide through conventional phosphoramidite synthesis, for example: 3'-5'-di-PEGylation as illustrated in FIG. 13. In alternative embodiments, reactive sites can be introduced at internal positions, using for example, the 5-position of pyrimidines, the 8-position of purines, or the 2'-position of ribose as sites for attachment of primary amines. In such embodiments, the nucleic acid can have several activated or reactive sites and is said to be multiply activated. Following synthesis and purification, the modified oligonucleotide is combined with the mono-activated PEG under conditions that promote selective reaction with the oligonucleotide reactive sites while minimizing spontaneous hydrolysis. In the preferred embodiment, monomethoxy-PEG is activated with succinimidyl propionate and the coupled reaction is carried out at pH 8.3. To drive synthesis of the bi-substituted PEG, stoichiometric excess PEG is provided relative to the oligonucleotide. Following reaction, the PEG-nucleic acid conjugate is purified by gel electrophoresis or liquid chromatography to separate fully, partially, and un-conjugated species.

The linking domains can also have one or more polyalkylene glycol moieties attached thereto. Such PAGs can be of varying lengths and may be used in appropriate combinations to achieve the desired molecular weight of the composition.

The effect of a particular linker can be influenced by both its chemical composition and length. A linker that is too long, too short, or forms unfavorable steric and/or ionic interactions with the target will preclude the formation of complex between aptamer and the target. A linker, which is longer than necessary to span the distance between nucleic acids, may reduce binding stability by diminishing the effective concentration of the ligand. Thus, it is often necessary to optimize linker compositions and lengths in order to maximize the affinity of an aptamer to a target.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Identification of 5'-Leader Sequences Using the TR-SELEX™ Method

A degenerate DNA library with the following design (shown in the 5' to 3' direction): T7 Promoter/G$_4$/degenerate 20 nucleotides/3'-Fixed sequence was synthesized with the following sequence:

```
(ARC 1140, SEQ ID NO 7))
5'TAATACGACTCACTATAGGGGNNNNNNNNNNNNNNNNNNNNACGTAAC

CGGTTAAACCCGGGTCGATGCAGTAAGCTAGCT3'.
```

This library was amplified using the 3'-primer AGCTAGCTTACTGCATCGAC (SEQ ID NO 104) and the 5'-primer TAATACGACTCACTATAG (SEQ ID NO 105). The double-stranded library was then transcribed using 1× Transcription Buffer (HEPES 200 mM, DTT 40 mM, spermidine 2 mM, Triton X-100 0.01%) at 37° C. overnight under the following conditions: 2'-OMe ATP CTP, UTP, GTP 1 mM each, 2'-OH GTP 30 µM, MgCl$_2$, 6.5 mM, MnCl$_2$ 2.0 mM, 10% w/v PEG-8000, 1 mM GMP, inorganic pyrophosphatase 0.5 units per 100 µL reaction, and Y639F/H784A/K378R T7 RNA polymerase 200 nM.

The resultant mixture was then precipitated (isopropanol, sodium chloride, EDTA), gel-purified (10% PAGE), excised and extracted from the gel, treated with DNase (RQ1, Promega, Madison Wis.), reverse-transcribed at 65° C. (Thermoscript, Invitrogen, Carlsbad, Calif.) using the 3'-primer used for PCR, and diluted directly into a splinted ligation reaction with the following oligonucleotides.

5' phosphorylated oligonucleotide encoding a T7 promoter (where p stands for 5'-phosphorylation):

```
    pTATAGTGAGTCGTATTA 3'        (SEQ ID NO 8)
```

Splint for ligation:

```
    5'TAATACGACTCACTATAGGGG 3'    (SEQ ID NO 9)
```

This mixture was heat-denatured, annealed, and then T4 DNA ligase (NEB, Beverley Mass.) was added followed by incubation at 16° C. overnight. Subsequent to the ligation step, the reaction was directly diluted into a PCR with the primers already described to amplify the transcribed sequences for input into the next round of the SELEX™ method. This scheme is presented in FIG. 2.

Figure 3:
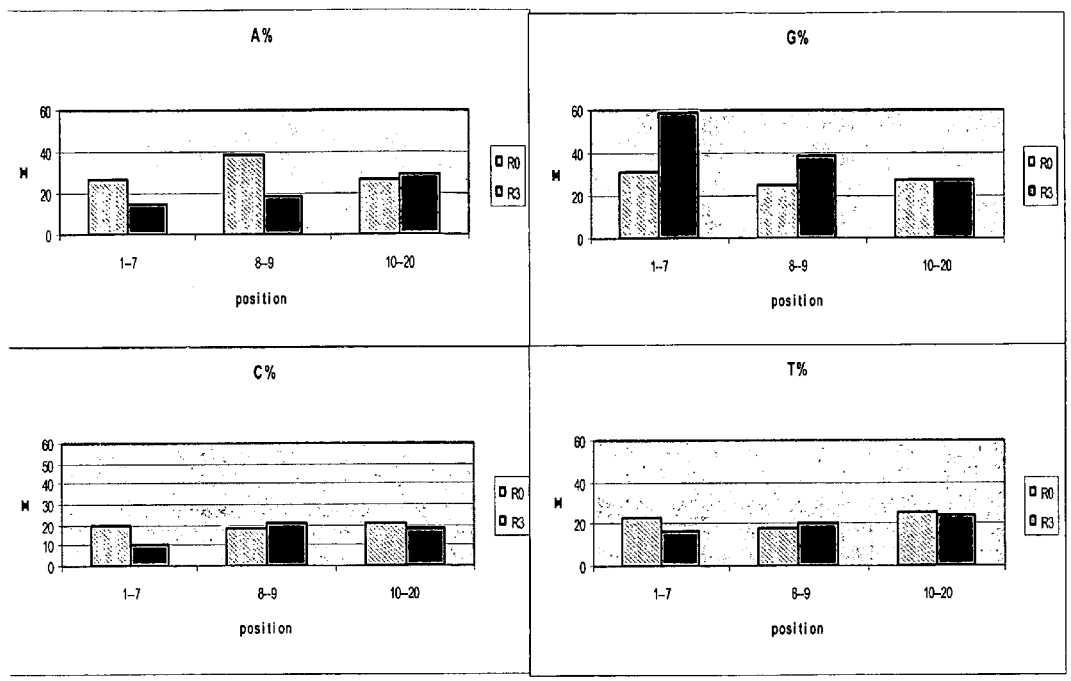
FIG. 3 shows a graphical analysis of the combined average nucleotide composition of regions selected from the twenty degenerate positions of a library of transcription template candidates before (R0) and after (R3) TR-SELEX™ selection.

After three rounds of TR-SELEX™ selection, the library was cloned using a TOPO TA cloning kit per manufacturer's instructions (Invitrogen, Carlsbad, Calif.), sequenced, and the statistics of nucleotide occurrence in the degenerate region were analyzed. Individual clones were assessed by PAGE-gel analysis for their ability to template the transcription of large concentrations of transcript, and the sequences of those that produced the highest yields of transcript were then utilized in the design of libraries that were in turn assayed by gel analysis for their ability to template the transcription of high yields of transcript. FIG. 3 shows the average percentage of nucleotide composition of regions of the twenty degenerate positions before and after 3 rounds of TR-SELEX™ selection. As indicated by FIG. 3, a strong preference for G from positions 5 to 13 in the transcript (1 to 9 in the degenerate region) was transcribed, thereafter no nucleotide is preferentially transcribed.

The clones discovered by sequencing after 3 Rounds of TR-SELEX™ selection were screened by PAGE-gel analysis for their ability to transcribe 2'-OMe nucleotides using ~200 nM template, 1× Transcription Buffer (HEPES 200 mM, DTT 40 mM, spermidine 2 mM, Triton X-100 0.01%), 2'-OMe ATP CTP, UTP, GTP at 1 mM each, 2'-OH GTP 30 uM, MgCl$_2$, 6.5 mM, MnCl$_2$ 2 mM, 10% w/v PEG-8000, 1 mM GMP, inorganic pyrophosphatase 0.5 units per 100 µL reaction, and Y639F/H784A/K378R mutant T7 RNA polymerase 200 nM, at 37° C. overnight. An example of one clone from Round 3, clone AMX411.D6 gave significantly more MNA transcript, as visualized by PAGE-gel, when compared to clones from Round 0. The DNA sequences of the clones generated from Round 3 are listed below (all sequences listed are in the 5'-3' direction):

```
SEQ ID NO 10 > AMX(411)_A1 ARC 1140 Rd 3_411-A1
TAATACGACTCACTATAGGGGGTGGGGCCAATGGCGGGATATACGTAACC

GGTTATACCCGGGTCGATGCAGTAAGCTAGCT

SEQ ID NO 11 > AMX(411)_B1 ARC 1140 Rd 3_411-B1
TAATACGACTCACTATAGGGGATGTACATATGTATTCGTGACGTGACCGG

TTAAACCCGGGTCGATGCAGTAAGCTAGCT

SEQ ID NO 12 > AMX(411)_C1 ARC 1140 Rd 3_411-C1
TAATACGACTCACTATAGGGGGAGCGGGGAGACGTAGTCATCACGTAGCC

GGTTAAACCCGGGTCGATGCAGTAAGCTAGCT

SEQ ID NO 13 > AMX(411)_D1 ARC 1140 Rd 3_411-D1
TAATACNACTCACTATAGGGGGTGGGGGTGGTGGTGATAACGTAACCGGT

TAAACCCGGGTCGATGCAGTAAGCTAGCT

SEQ ID NO 14 > AMX(411)_E1 ARC 1140 Rd 3_411-E1
TAATACGACTCACTATAGGGGGGTGTCACCAGATATGCCTTGAACGTAAC

CCGTTAAACCCGGGTCGATGCAGTAAGCTAGCT

SEQ ID NO 15 > AMX(411)_F1 ARC 1140 Rd 3_411-F1
TAATACGACTCACTATAGGGGGTAGGGGCACGCACTAACCAACGTAACC

GGTTAAACCCGGGTCGATGCAGTAAGCTAGCT
```

SEQ ID NO 16 > AMX(411)_G1 ARC 1140 Rd 3_411-G1
TAATACGACTCACTATAGGGGGAGGGGGTGCTGACCNCAAACA

SEQ ID NO 17 > AMX(411)_H1 ARC 1140 Rd 3_411-H1
TAATACGACTCACTATAGGGGTGGGGCTCGGATGAGACAATACGTAACCG
GTTAAACCCGGGTCGATGCAGTAAGCTAGCT

SEQ ID NO 18 > AMX(411)_A2 ARC 1140 Rd 3_411-A2
TAATACGACTCACTATAGGGGGGGGTGGGTAGGCGAGCACTCCACGTAAC
CAGTTAAACCCGGGTCGATGCAGTAAGCTAGCT

SEQ ID NO 19 > AMX(411)_B2 ARC 1140 Rd 3_411-B2
TAATACGACTCACTATAGGGGGAAGGACGAGCAGACGAGCAACGTAACC
TGTTAAACCCGGGTCGATGCAGTAAGCTAGCT

SEQ ID NO 20 > AMX(411)_C2 ARC 1140 Rd 3_411-C2
TAATACGACTCACTATAGGGGGGGCGGTTAGAGTGTAAGTACCGACGTA
ACCGGTTAAACCCGGGTCGATGCAGTAAGCTAGCT

SEQ ID NO 21 > AMX(411)_D2 ARC 1140 Rd 3_411-D2
TAATACGACTCACTATAGGGGGGTTGCTGTTAGTAACGCCACGTAACCGG
TTAAACTTGGTCGATGCAGTAAGCTAGCT

SEQ ID NO 22 > AMX(411)_E2 ARC 1140 Rd 3_411-E2
TAATACGACTCACTATAGGGGGGCGGGAGAATGTTATATAGTTACGGTAA
CCGGTTAAACCCGGGTCGATGCAGTAAGCTAGCT

SEQ ID NO 23 > AMX(411)_F2 ARC 1140 Rd 3_411-F2
TAATACGACTCACTATAGGGGAAAGGGGCGGTATGGTACACACGTAACAG
GTTAAACCCGGGTCGATGCAGTAAGCTAGCT

SEQ ID NO 24 > AMX(411)_G2 ARC 1140 Rd 3_411-G2
TAATACGACTCACTATAGGGGGGACGTGTTAGCATTCCAGAATTCGTAAC
CTAAACCCGGGTCGATGCAGTAAGCTAGCT

SEQ ID NO 25 > AMX(411)_H2 ARC 1140 Rd 3_411-H2
TAATACGACTCACTATAGGGGGCGTGGGAGATAGGTTCAAGGACGTACCG
GTTATACCCGGGTCGATGCAGTAAGCTAGCT

SEQ ID NO 26 > AMX(411)_A3 ARC 1140 Rd 3_411-A3
TAATACGACTCACTATAGGGGGCTCCGTGCTATCGTCGGATAACGTAAC
CCGTTAAACCCGGGTCGATGCAGTAAGCTAGCT

SEQ ID NO 27 > AMX(411)_B3 ARC 1140 Rd 3_411-B3
TAATACGACTCACTATAGGGGGGAGAAGGTCTTAAGGTCGCCAACGTAA
CTGTTAAACCCGGGTCGATGCAGTAAGCTAGCT

SEQ ID NO 28 > AMX(411)_C3 ARC 1140 Rd 3_411-C3
TAATACGACTCACTATAGGGGGGGCATACGAGTTTAGGTGGAGACGTAAC
CGGTTAAACCCGGGTCGATGCAGTAAGCTAGCT

SEQ ID NO 29 > AMX(411)_D3 ARC 1140 Rd 3_411-D3
TAATACGACTCACTATAGGGGGATGATGACTTCCGCGTTAATACGTTACC
GGTTAAACCCGGGTCGATGCAGTAAGCTAGCT

SEQ ID NO 30 > AMX(411)_E3 ARC 1140 Rd 3_411-E3
TAATACGACTCACTATAGGGGTGGGACGCCGTCTGAGTATAACGTACCCG
GTCGGGTCGATGCAGTAAGCTAGCT

SEQ ID NO 31 > AMX(411)_G3 ARC 1140 Rd 3_411-G3
TAATACGACTCACTATAGGGGGGGGGGACGTAATCGGCTATCGTTCACG
TAACCGGTTAAACCCGGGTCGATGCAGTAAAGGGCGA

SEQ ID NO 32 > AMX(411)_H3 ARC 1140 Rd 3_411-H3
TAATACGACTCACTATAGGGTGGGACGGGCAGCGTGGATGTAGGACGTAA
CCGGTTAAACGCGGGTCGATGCAGTAAGCTAGCT

SEQ ID NO 33 > AMX(411)_A4 ARC 1140 Rd 3_411-A4
TAATACGACTCACTATAGGGGGGTTTGTCTGAAGTGAAGCAGAACGTAAC
CGGTTAATCCCGGGTCGATGCAGTAAGCTAGCT

SEQ ID NO 34 > AMX(411)_B4 ARC 1140 Rd 3_411-B4
TAATACGACTCACTATAGGGGGGGAGGGCACATCATCGTATCAAACGTAA
CCAGTTAATCCCGGGTCGATGCAGTAAGCTAGCT

SEQ ID NO 35 > AMX(411)_C4 ARC 1140 Rd 3_411-C4
TAATACGACTCACTATAGGGGAGGCTAGAGGACGCGACAGAACGTAACCG
GTTAAACCCGGGTCGATGCAGTAAGCTAGCT

SEQ ID NO 36 > AMX(411)_D4 ARC 1140 Rd 3_411-D4
TAATACGACTCACTATAGGGGCGATCGCGAAGGGATTTCAACGTAACCG
GTTAAACCCGGGTCGATGCAGTAAGCTAGCT

SEQ ID NO 37 > AMX(411)_E4 ARC 1140 Rd 3_411-E4
TAATACGACTCACTATAGGGGGGTAGGGAAAGATTACGGGGCTACGTAAC
CGGTTATACCTGGGTCGATGCAGTAAGCTAGCT

SEQ ID NO 38 > AMX(411)_F4 ARC 1140 Rd 3_411-F4
TAATACGACTCACTATAGGGGTGGCTATGGCTAACACGTAACCGGTTATA
CCCGGGTCGATGCAGTAAGCTAGCT

SEQ ID NO 39 > AMX(411)_G4 ARC 1140 Rd 3_411-G4
TAATACGACTCACTATAGGGGGGGGCGGTGGCTGTGCAAGCGGAAACGT
AACCGGTTAAACCCGGGTCGATGCAGTAAGCTAGCT

SEQ ID NO 40 > AMX(411)_H4 ARC 1140 Rd 3_411-H4
TAATACGACTCACTATAGGGGGGTGGGGCACGGTACTGAGTTACGTTAC
CGGTTAAACCCGGGTCGATGCAGTAAGCTAGCT

SEQ ID NO 41 > AMX(411)_A5 ARC 1140 Rd 3_411-A5
TAATACGACTCACTATAGGGGGGAGTGGGACAATTAGAAGATGACGTAA
CCGTCCGGGTCGATGCAGTAAGCTAGCT

SEQ ID NO 42 > AMX(411)_B5 ARC 1140 Rd 3_411-B5
TAATACNACTCACTATAGGGGTGCAGTGAGGAGCGACNAGTACGTTACCG
GTTAAATCCGAGTCGATGCAGTAAGCTAGCT

SEQ ID NO 43 > AMX(411)_C5 ARC 1140 Rd 3 411-C5
TAATACNACTCACTATAGGGGGACGGGCACTGTGGATGATTTAACGTTAC
CGGTTAAACCCGAGTCGATGCAGTAAGCTAGCT

SEQ ID NO 44 > AMX(411)_D5 ARC 1140 Rd 3_411-D5
TAATACNACTCACTATAGGGGTCGATGCAGTAAGCTAGCT

SEQ ID NO 45 > AMX(411)_E5 ARC 1140 Rd 3_411-E5
TAATACNACTCACTATAGGGGGTGATATTGACCTCTAACAGCACGTAACC
GGTTAAACCCGGTCGATGCAGTAAGCTAGCT

SEQ ID NO 46 > AMX(411)_F5 ARC 1140 Rd 3_411-F5
TAATACGACTCACTATAGGGGGGGGGTGCAGAGGATGCATCCAAGCTCG
TAATCGGTGGTCGATGCAGTAAGCTAGCT

SEQ ID NO 47 > AMX(411)_G5 ARC 1140 Rd 3_411-G5
TAATACGACTCACTATAGGGGGGGCGGGTGCTTGTGCCTAATCACGTAA
CCGGTTAAACCCGGGTCGATGCAGTAAGCTAGCT

SEQ ID NO 48 > AMX(411)_H5 ARC 1140 Rd 3_411-H5
TAATACGACTCACTATAGGGGTTTGGTAATCGAACGTGGAACGCAACCGG

TTTAACCGGGTCGATGCAGTAAGCTAGCT

SEQ ID NO 49 > AMX(411)_A6 ARC 1140 Rd 3_411-A6
TAATACGACTCACTATAGGGGGATGGAAGAGGCTTGATATCACGTAACC

GGTTAAACCTGGGTCGATGCAGTAAGCTAGCT

SEQ ID NO 50 > AMX(411)_B6 ARC 1140 Rd 3_411-B6
TAATACGACTCACTATAGGGGTTATACTAACTCTGTACACAACGTAACC

GGCCGGGTCGATGCAGTAAGCTAGCT

SEQ ID NO 51 > AMX(411)_C6 ARC 1140 Rd 3_411-C6
TAATACGACTCACTATAGGGGTATAGGGGGGGTATCGGTGTACGTAACCG

GTTAAACCCGGGTCGATGCAGTAAGCTAGCT

SEQ ID NO 52 > AMX(411)_D6 ARC 1140 Rd 3_411-D6
TAATACGACTCACTATAGGGGAGTACAATAAGGTTCCGAGAACGCGACCG

GTTAAACCCGGGTCGATGCAGTAAGCTAGCT

SEQ ID NO 53 > AMX(411)_E6 ARC 1140 Rd 3_411-E6
TAATACGACTCACTATAGGGGTGCGCGGTTACAAGGCAACATACGTAACC

GGTTAAACCCGGGTCGATGCAGTAAGCTAGCT

SEQ ID NO 54 > AMX(411)_F6 ARC 1140 Rd 3_411-F6
TAATACNACTCACTATAGGGGGACGGGGTGACAAAGTGTCNAACGTAAC

CGGTTAAACCCGGGTCGATGCAGTAAGCTAGCT

SEQ ID NO 55 > AMX(411)_G6 ARC 1140 Rd 3_411-G6
TAATACGACTCACTATAGGGGAGACGGCGGTACAAGTCCATATGTAACCG

GTTAAACCCGGGTCGATGCAGTAAGCTAGCT

SEQ ID NO 56 > AMX(411)_H6 ARC 1140 Rd 3_411-H6
TAATACGACTCACTATAGGGGAGTGGGGCTTCTCGTTGCCACGTAACCG

CTTAAACCCGGGTCGATGCAGTAAGCTAGCT

SEQ ID NO 57 > AMX(423)_A7 ARC 1140 R3_423-A7
TAATACGACTCACTATAGGGGGCTGAGCGTGTTTGAGGGACCACGTTAC

CGGTTAAACCCGGGTCGATGCAGTAAGCTAGCT

SEQ ID NO 58 > AMX(423)_B7 ARC 1140 R3_423-B7
TAATACGACTCACTATAGGGGGTGGGCGCAATGAAAAGTTGGGCGTAAC

CGGTTCAACCCGGGTCGATGCAGTAAGCTAGCT

SEQ ID NO 59 > AMX(423)_C7 ARC 1140 R3_423-C7
TAATACGACTCACTATAGGGGGTAGTGAAGTAAGGCAGTGTTACGTAACC

GGTGAACCCGGGTCGATGCAGTAAGCTAGCT

SEQ ID NO 60 > AMX(423)_D7 ARC 1140 R3_423-D7
TAATACGACTCACTATAGGGGGAGGGTGGGCTAGAACACAACGTAAC

CGGTTAAACCCGGGTCGATGCAGTAAGCTAGCT

SEQ ID NO 61 > AMX(423)_E7 ARC 1140 R3_423-E7
TAATACGACTCACTATAGGGGGGAGAGAGGCGGTTACGTAGGGACGTTA

CCGATTGAACTCAGGTCGATGCAGTAAGCTAGCT

SEQ ID NO 62 > AMX(423)_F7 ARC 1140 R3 423-F7
TAATACGACTCACTATAGGGGGGGGGCGAATAGGTAGGGCGACGAACG

TTACCGGTTAAACCCGGGTCGATGCAGTAAGCTAGCT

SEQ ID NO 63 > AMX(423)_G7 ARC 1140 R3_423-G7
TAATACGACTCACTATAGGGGGAGAGGAGGTCCGGCTAGACAACGTAACC

GGTTAAACCCGGGTCGATGCAGTAAGCTAGCT

SEQ ID NO 64 > AMX(423)_H7 ARC 1140 R3_423-H7
TAATACGACTCACTATAGGGGGGAGGACGGGTCGTACTGTTAAACCTGGG

TCGATGCAGTAAGCTAGCT

SEQ ID NO 65 > AMX(423)_B8 ARC 1140 R3_423-B8
TAATACGACTCACTATAGGGGCGCAACAACGGGAAGTATACGTAACCGG

TTTAAACCCGGGTCGATGCAGTAAGCTAGCT

SEQ ID NO 66 > AMX(423)_C8 ARC 1140 R3_423-C8
TAATACGACTCACTATAGGGGAAGGAACACGCACATGCATAACGTAACT

GGTTGACCCCGGGTCGATGCAGTAAGCTAGCT

SEQ ID NO 67 > AMX(423)_D8 ARC 1140 R3_423-D8
TAATACGACTCACTATAGGGGAGTGGGGAGTACTGTGGACAACGTGACCG

GTTAAACCCGGGTCGATGCAGTAAGCTAGCT

SEQ ID NO 68 > AMX(423)_E8 ARC 1140 R3_423-E8
TAATACGACTCACTATAGGGGTCGATGCAGTAAGCTAGCT

SEQ ID NO 69 > AMX(423)_F8 ARC 1140 R3_423-F8
TAATACGACTCACTATAGGGGGGGGGCTAGGGCGGTCGGATCGGACGTA

ACCAGTTAAACCCGGGTCGATGCAGTAAGCTAGCT

SEQ ID NO 70 > AMX(423)_G8 ARC 1140 R3_423-G8
TAATACGACTCACTATAGGGGGGGTGGGGGTTGCTACATGCCCTCGTAAC

CGGTTAAGCCCAGGTCGATGCAGTAAGCTAGCT

SEQ ID NO 71 > AMX(423)_H8 ARC 1140 R3_423-H8
TAATACGACTCACTATAGGGGGGTGGCGACGATGGAGAGAATAACGTAAT

CGGTTAAACCCGGGTCGATGCAGTAAGCTAGCT

SEQ ID NO 72 > AMX(423)_A9 ARC 1140 R3_423-A9
TAATACGACTCACTATAGGGGGTAGGCGGGCCTCATCAACAACGCAACCG

GTTAAACCCGGGTCGATGCAGTAAGCTAGCT

SEQ ID NO 73 > AMX(423)_B9 ARC 1140 R3_423-B9
TAATACGACTCACTATAGGGGGGTGGCTGGTAAGGACACAAACACGTAACT

CGTTAAACCCGGGTCGATGCAGTAAGCTAGCT

SEQ ID NO 74 > AMX(423)_C9 ARC 1140 R3_423-C9
TAATACGACTCACTATAGGGGGGCGGGCAGCGCTTATAGATCCACGTAAC

CGGTTAAACCCGGGTCGATGCAGTAAGCTAGCT

SEQ ID NO 75 > AMX(423)_D9 ARC 1140 R3_423-D9
TAATACGACTCACTATAGGGGGGGGGGTATCTGCGGTTAGGCTATCGACGT

ACCCAGTTAAACCCGGGTCGATGCAGTAAGCTAGCT

SEQ ID NO 76 > AMX(423)_F9 ARC 1140 R3_423-F9
TAATACGACTCACTATAGGGGGGGTAGGGGACATCATAGGTATACGTAAC

CGGTTAACCCGGGTCGATGCAGTAAGCTAGCT

SEQ ID NO 77 > AMX(423)_H9 ARC 1140 R3_423-H9
TAATACGACTCACTATAGGGGCGCGTGCGTGTATCCATTAAACGTGACTG

GTTAAACCCGGGTCGATGCAGTAAGCTAGCT

SEQ ID NO 78 > AMX(423)_A10 ARC 1140 R3_423-A10
TAATACGACTCACTATAGGGGGGGAGCGTGGATCTTGAGTGTATACGT

AACCGGTTAAACCCGGTCGATGCAGTAAGCTAGCT

SEQ ID NO 79 > AMX(423)_B10 ARC 1140 R3_423-B10
TAATACGACTCACTATAGGGGATGGAGAGGAGTGTACGCATATACAACCG

GTTAAACCCGGGTCGATGCAGTAAGCTAGCT

SEQ ID NO 80 > AMX(423)_C10 ARC 1140 R3_423-C10
TAATACGACTCACTATAGGGGCGGGTGGTCGCGATGGTTAACGTAACTGG

TTAAACCCGGGTCGATGCAGTAAGCTAGCT

SEQ ID NO 81 > AMX(423)_D10 ARC 1140 R3_423-D10
TAATACGACTCACTATAGGGGGGGGGGGGACGTTAGCTTCTCTGTATTT

ACGTAACCGGTTAAGCCCGGGTCGATGCAGTAAGCTAGCT

SEQ ID NO 82 > AMX(423)_E10 ARC 1140 R3_423-E10
TAATACGACTCACTATAGGGGTCGATGCAGTAAGCTAGCT

SEQ ID NO 83 > AMX(423)_F10 ARC 1140 R3 423-F10
TAATACGACTCACTATAGGGGGATGGAGTGGGTGCAAATAANACGTAAC

TGGTTAAACCCGGGTCGATGCAGTAAGCTAGCT

SEQ ID NO 84 > AMX(423)_G10 ARC 1140 R3_423-G10
TAATACGACTCACTATAGGGGAGNGTGAGGGGTGAATANTAANGTAANCN

GTTAAACCTGGGTCGATGNNNTANNCTNGNT

SEQ ID NO 85 > AMX(423)_H10 ARC 1140 R3_423-H10
NAATNNGACTCACAANAGGGGTCGATGCAGTAAGCTAGCT

SEQ ID NO 86 > AMX(423)_A11 ARC 1140 R3_423-A11
TAATACGACTCACTATAGGGGGGGTGACGTACGGATCTAAGTAACGTAA

CCGGTTAAACCCGGGTCGATGCAGTAAGCTAGCT

SEQ ID NO 87 > AMX(423)_B11 ARC 1140 R3_423-B11
TAATACGACTCACTATAGGGGAGGGACAGACACTTTGTAGACGTAACCAG

TTAAACCCGGGTCGATGCAGTAAGCTAGCT

SEQ ID NO 88 > AMX(423)_C11 ARC 1140 R3_423-C11
TAATACGACTCACTATAGGGGGGGGACTTGGCACTACGTAACAACGTAAC

CGCTTAAACCCGGGTCGATGCAGTAAGCTAGCT

SEQ ID NO 89 > AMX(423)_D11 ARC 1140 R3_423-D11
TAATACGACTCACTATAGGGGGGGGGGCCTCTCGACCAAAAGCCCAACGT

AACCGGTTAAACCCGGGTCGATGCAGTAAGCTAGCT

SEQ ID NO 90 > AMX(423)_E11 ARC 1140 R3_423-E11
TAATACNACTCACTATAGGGGGGGGGGGATAGTCATGACTGATAAAACGT

AACTGTTGAGCCCGGGTCGATGCAGTAAGCTAGCT

SEQ ID NO 91 > AMX(423)_F11 ARC 1140 R3_423-F11
TAATACGACTCACTATAGGGGACAGTGCTAGTGGAATAGCAACGTAACCA

GTTAAACCCGGGTCGATGCAGTAAGCTAGCT

SEQ ID NO 92 > AMX(423)_G11 ARC 1140 R3_423-G11
TAATACGACTCACTATAGGGGACGACCACTATACTCCGAGAACGTAACCG

GTTAAACCCGGGTCGATGCAGTAAGCTAGCT

SEQ ID NO 93 > AMX(423)_H11 ARC 1140 R3_423-H11
TAATACGACTCACTATAGGGGGATGGAGGCGTAGTGTAGTCAACGTTACC

GGTTAAACCCGGGTCGATGCAGTAAGCTAGCT

SEQ ID NO 94 > AMX(423)_A12 ARC 1140 R3_423-A12
TAATACGACTCACTATAGGGGGGAGGTATAGATGGAATGGTTATGTAACC

TGTTAAACCCGGGTCGATGCAGTAAGCTAGCT

SEQ ID NO 95 > AMX(423)_B12 ARC 1140 R3_423-B12
TAATACGACTCACTATAGGGGTGGGGAGGACCACTTAGATAACGTCACCG

GTTAAACCCGGGTCGATGCAGTAAGCTAGCT

SEQ ID NO 96 > AMX(423)_C12 ARC 1140 R3_423-C12
TAATACGACTCACTATAGGGGGGGATAGGGGCGAGAGAGTCACAACGTAAC

CGGTTAATCCCGGGTCGATGCAGTAAGCTAGCT

SEQ ID NO 97 > AMX(423)_E12 ARC 1140 R3_423-E12
TAATACGACTCACTATAGGGGGGGGATGGCCGAATCATAAAATAACGTAA

CCGTTAGACCCGGGTCGATGCAGTAAGCTAGCT

SEQ ID NO 98 > AMX(423)_F12 ARC 1140 R3_423-F12
TAATACGACTCACTATAGGGGGCGATTGCTGAGTCAGTTCGTAATCGGTT

AAACCCGGGTCGATGCAGTAAGCTAGCT

SEQ ID NO 99 > AMX(423)_G12 ARC 1140 R3_423-G12
TAATACGACTCACTATAGGGGGGGGAGGATCCGAAACACAGGGATCCGTA

ACCGGTTAAAGCCGGGTCGATGCAGTAAGCTAGCT

Example 2

Libraries Incorporating Leader Sequences Identified by the TR-SELEX™ Method

The identified 5'-leader sequence elements (the first 10 nucleotides of the degenerate region) from higher 2'-modified transcript-yielding clones identified using TR-SELEX™ selection as described in Example 1 were utilized to design libraries which incorporate the leader sequence elements into the 5'-fixed region, with the goal of promoting an increase in transcript yield containing 2'-modified nucleotides. In one embodiment, the design strategy incorporates the first 14 nucleotides of the identified clones (the 4 guanosines comprising the 5' fixed region plus the first 10 nucleotides of the degenerate region) as the 5'-leader sequence immediately followed by an additional 6-8 fixed nucleotides to facilitate subsequent PCR amplification, immediately followed by a degenerate region 30-40 nucleotides in length, immediately followed by a 3'-fixed region to also facilitate subsequent PCR amplification.

Examples of the DNA sequences of the libraries designed which incorporate the identified leader sequence elements are listed below.

For each of the sequences of the libraries of DNA transcription templates listed below, the 5'-leader sequence element is shown underlined, and all sequences are in the 5'-3' direction.

ARC 2118 (SEQ ID NO 3)
TAATACGACTCACTATAGGGGAGTACAATAACGTTCTCGNNNNNNNNNNN

NNNNNNNNNNNNNNNNNNNGGATCGTTACGACTAGCATCGATG

ARC2119 (SEQ ID NO 4)
TAATACGACTCACTATAGGGGGTGATATTGACGTTCTCGNNNNNNNNNNN

NNNNNNNNNNNNNNNNNNNGGATCGTTACGACTAGCATCGATG

ARC2120 (SEQ ID NO 5)
TAATACGACTCACTATAGGGGTGCGCGGTTACGTTCTCGNNNNNNNNNNN

NNNNNNNNNNNNNNNNNNNGGATCGTTACGACTAGCATCGATG

ARC2121 (SEQ ID NO 6)
TAATACGACTCACTATAGGGGGAGGGGTGCCGTTCTCGNNNNNNNNNNN

NNNNNNNNNNNNNNNNNNNGGATCGTTACGACTAGCATCGATG

A control DNA transcription templates without a leader sequence is listed below, in the 5'-3' direction.

(ARC2117, SEQ ID NO 106)
TAATACGACTCACTATAGGGGAGAGGAGAGAACGTTCTCGNNNNNNNNNNN

NNNNNNNNNNNNNNNNNNNNNNNGGATCGTTACGACTAGCATCGATG

To test whether the newly designed libraries promote an increased yield of transcripts containing 2'-O-methyl nucleotides, the libraries were transcribed using two different modified T7 RNA polymerases for comparison, the Y639F/H784A/K378R mutant T7 RNA polymerase, and the Y639L/H784A/K378R mutant polymerase (transcription reaction mixtures without polymerase was used as a negative control), in a transcription mixture containing ~200 nM template, 1× transcription buffer (HEPES 200 mM, DTT 40 mM, spermidine 2 mM, Triton X-100 0.01%), 2'-OMe ATP, CTP, UTP, and GTP 1 mM each, 2'-OH GTP at 30 uM, MgCl$_2$ 6.5 mM, MnCl$_2$ 2.0 mM, PEG-8000 w/v 10%, GMP 1 mM, Y639F/H784A/K378R mutant T7 RNA polymerase or Y639L/H784A/K378R mutant T7 RNA polymerase 200 nM, inorganic pyrophosphatase 5 units/mL, at 37° C. overnight. Transcript yield for each condition was assayed by PAGE-gel analysis using 200 uL of reaction mixture, and transcript yield for each condition was quantitated from UV-shadowing of the PAGE-gel analysis using ImageQuant version 5.2 software (Molecular Dynamics).

FIG. 4 summarizes the quantitated results of the PAGE-gel analysis, showing the fold-increase of transcript yield with both Y639F/H784A/K378R ("FAR") and Y639L/H784A/K378R ("LAR") mutant T7 RNA polymerases relative to the no polymerase negative control. As can be seen in FIG. 4, a significant improvement in the yield of fully 2'-OMe containing transcripts was seen when the Y639L/H784A/K378R mutant T7 RNA polymerase was used to transcribe the new libraries incorporating the new leader sequence elements as compared to the Y639F/H784A/K378R mutant polymerase. Notably, ARC2118, ARC2119, ARC2120 gave significantly higher yields of 2'-OMe containing transcripts when combined with the Y639L/H784A/K378R mutant T7 RNA polymerase as compared to the Y639F/H784A/K378R mutant T7 RNA polymerase. An increase in transcript yield by using the Y639L/H784A/K378R mutant T7 RNA polymerase was also seen with ARC2117, a library formerly designed which lacks the newly identified leader sequence elements, known to transcribe under the given conditions with the Y639F/H794A/K378R mutant polymerase, which was used as a control. These results indicate that the yields of 2'-OMe-containing transcript may be increased by utilizing the Y639L/H784A/K378R mutant T7 RNA polymerase as compared to the Y639F/H784A/K378R mutant T7 RNA polymerase. In addition, several of the new libraries (ARC2118 and ARC2119) incorporating the leader sequence elements identified through the TR-SELEX™ method also gave higher yields of 2'-OMe containing transcripts than the control library, ARC2117, when using the Y639L/H784A/K378R mutant T7 RNA polymerase, indicating that an improvement in the yield of 2'-OMe containing transcript can be achieved by utilizing the Y639L/H784A/K378R mutant in combination with the particular newly identified leader sequences of the present invention.

Example 3

Polymerase Expression and Purification

Mutant T7 RNA polymerase, for use in the methods of the invention may be prepared as follows. T7 RNA polymerase (nucleic acid and amino acid sequence shown in FIGS. 5A and 5B respectively and described in Bull, J. J et al., *J. Mol. Evol.*, 57 (3), 241-248 (2003) may be mutated to result in the LA mutant (Y639L/H784A), the LAR mutant (Y639L/H784A/K378R), the LLA mutant (P266L/Y639L/H784A) or the LLAR mutant P266L/Y639L/H784A/K378R). T7 RNA polymerase may be comprised in an expression vector (an example of a T7 RNA polymerase expression vector is described in U.S. Pat. No. 5,869,320 herein incorporated by reference in its entirety) or may be inserted into an expression vector following mutagenesis. The mutated T7 RNA polymerase may be engineered to optionally comprise a His-tag for ease during protein purification.

Complementary oligonucleotide sequences that contain the Leucine mutation for position 639 (agtcatgacgctg-gctCTGgggtccaaagagttcg (SEQ ID NO 107 and gaactctttg-gacccCAGagccagcgtcatgact (SEQ ID NO 108) may be synthesized. Complementary oligonucleotide sequences (ggctggcatctctcTgatgttccaaccttgc (SEQ ID NO 109) and gcaaggttggaacatcAgagagatgccagcc (SEQ ID NO 110) for P266L mutation may be synthesized. Complementary oligonucleotide sequences (cgctcctaactttgtaGCcagccaagacggtagc (SEQ ID NO 111) and gctaccgtcttggctgGCtacaaagttaggagcg (SEQ ID NO 112)) for H784A mutation may be synthesized. Complementary oligonucleotide sequences (gctctcaccgcgtg-gaGacgtgctgccgctgct (SEQ ID NO 113) and agcagcggcag-cacgtCtccacgcggtgagagc (SEQ ID NO 114)) for K378R mutation may be synthesized. Site-directed mutagenesis may be performed using QuikChanges® Site-Directed Mutagenesis Kit (Stratagene, La Jolla, Calif.) according to the manufacturer's instructions to result in nucleic acid sequences (FIG. 6) encoding mutant polymerases having the above indicated combination of mutations. The resulting nucleic acid sequence encoding a mutant polymerase of the invention may be inserted into the desired expression vector using standard techniques for expression and purification.

Expression and Purification

The expression vector comprising the mutant T7 polymerase nucleic acid sequence is is transformed int BL21 (DE3) competent cells (Stratagene, Calif.) and incubated on ice for 20 min. Heat shock is performed by putting the tube in 42° C. for 2 min. After putting the tube on ice for 1 minute, 1 ml L broth ("LB") is added and incubated in 37° C. shaker for 45 min. 100 ul of culture liquid is plated on LB+Amp agar plate and incubated at 37° C. overnight.

A single colony from the overnight cultured plate is inoculated into 100 ml LB-Amp+ (150 ug/ml), 37° C. overnight. On the second day, two 4-liter flasks containing 2 liters of pre-warmed LB+Amp are inoculated with 50 ml of overnight culture and grown at 37° C. until OD600 reaches between 0.6-0.8. 200 ul of 1M IPTG is added to each 2 L cell culture with final concentration of 100 uM and grow for another 3 hrs at 37° C. The cells are pelleted by spinning at 5000 rpm for 10 min. Cells are resuspended in 200 ml lysis buffer (Lysis buffer: 50 mM Tris-Cl, pH 8.0, 100 mM NaCl, 5% Glycerol, 1 mM imidazole, betamercaptoethanol ("BME") 5 mM) and divided into 6 conical 50 ml tubes. The cells are sonicated at power level 8, 3×30" for each tube and then bacterial debris is spun down at 11,000 rpm for 60 min and the supernatant filtered through 0.22 uM filter. Imidazole is added to the filtrate to a final concentration of 10 mM.

The filtrate is loaded onto a 5 ml Ni-NTA column (GE Healthcare Bio-Sciences, NJ) with sample pump. The column is washed with 10 column volumes (CV) of buffer A (Buffer A: 50 mM Tris-Cl, pH 8.0, 100 mM NaCl, 5% Glycerol, 10 mM imidazole, BME 10 mM) containing 20 mM imidazole. The column is then washed with 10 CV of buffer with a linear gradient of imidazole concentration from 40 mM to 70 mM in buffer A. The protein is eluted with 6 CV of Buffer B (Buffer B: 50 mM Tris-Cl, pH 8.0, 100 mM NaCl, 5% Glycerol, 250 mM imidazole, BME 10 mM). After checking the collection fractions with 5 µl of sample on 4-12% SDS-PAGE, all the fractions of interest are combined and dialyzed (dialysis tubing: Spectrum Spectra/por Molecular porous membrane (VWR) MWCO: 12-14000) in 1 L of dialysis buffer (Dialysis buffer: 50 mM Tris-Cl, pH 7.9, 100 mM NaCl, 50% Glycerol, 0.1 mM EDTA, 0.1% Triton X-100, BME 20 mM) overnight. The dialysis buffer is changed after 12 hours and dialysis is carried out for an additional 4 hours. The concentration of T7 RNA polymerase is measured using the Bradford assay as described in Bradford, M. M. (1976) *Anal. Biochem.* 72, 248.

Example 4

Transcription incorporating 100% 2'-O-methyl nucleotides

Example 4A

2'-O-methyl transcription without 2'-OH GTP

An experiment was performed to test the sensitivity of Y639L/H784A/K378R mutant polymerase to the concentration of 2'-OH GTP by using a titration of 2'-OH GTP.

ARC2118 and ARC2119, two libraries incorporating the new leader sequence elements identified through TR-SELEX™ selection (described in Example 1), which showed high transcript yields when used with the Y639L/H784A/K378R mutant T7 RNA polymerase (see Example 2), were used to test the sensitivity of transcription of the Y639L/H784A/K378R mutant T7 RNA polymerase to the concentration of 2'-OH GTP. Transcriptions were performed using a titration of 2'-OH GTP (0-160 uM) with 1× transcription buffer (HEPES 200 mM, DTT 40 mM, spermidine 2 mM, Triton X-100 0.01%), ~200 nM template, 2'-OMe ATP, CTP, UTP, and GTP 1 mM each, MgCl$_2$ 6.5 mM, MnCl$_2$ 2.0 mM, PEG-8000 w/v 10%, GMP 1 mM, inorganic pyrophosphatiase 5 units/mL, Y639L/H784A/K378R mutant T7 RNA polymerase 200 nM, at 37° C. overnight.

Transcript yield under each condition was assayed by PAGE-gel analysis using 200 uL of reaction mixture, and transcript yield for each condition was quantitated from UV-shadowing of the PAGE-gel analysis using ImageQuant version 5.2 software (Molecular Dynamics). FIG. 7 summarizes the quantitated results of the PAGE-gel analysis, showing the fold-increase of transcript yield with of each condition relative to the background. As can be seen in FIG. 7, ARC2118 and ARC2119 transcribed with Y639L/H784A/K378R under all conditions, including no 2'-OH GTP, and the yield in the absence of 2'-OH GTP was comparable to transcription yield where 2'-OH GTP was included in the reaction mixture. These results indicate that the Y639L/H784A/K378R mutant T7 RNA polymerase does not require the presence of 2'-OH GTP for increased transcript yield, as opposed to the Y639F/H784A/K378R mutant T7 RNA polymerase, which requires 2'-OH GTP for transcription (data not shown).

An experiment was subsequently performed to determine the optimal transcription conditions to be used with the Y639L/H784A/K378R mutant T7 RNA polymerase when combined with the leader sequences identified by TR-SELEX™ selection, (described in Example 1). ARC2119, a library incorporating the new leader sequence elements identified through TR-SELEX™ selection which showed significantly higher transcript yield when used with the Y639L/H784A/K378R mutant T7 RNA polymerase (see Example 2) was used to test the effect of varying the 2'-OMe NTP, magnesium and manganese concentrations on transcript yield.

Transcriptions were performed using 1× transcription buffer (HEPES 200 mM, DTT 40 mM, spermidine 2 mM, Triton X-100 0.01%), ~200 nM template, 2'-OMe ATP, CTP, UTP, and GTP (0.5 mM, 1 mM, 1.5 mM, and 2 mM each), MgCl$_2$ (5 mM, 6.5 mM, 8 mM, and 9.5 mM), MnCl$_2$ (1.5 mM, 2 mM, 2.5 mM, 3 mM), PEG-8000 w/v 10%, GMP 1 mM, inorganic pyrophosphatase 5 units/mL, Y639L/H784A/K378R mutant T7 RNA polymerase 200 nM, at 37° C. overnight.

Transcript yield under each condition was assayed by PAGE-gel analysis using 200 uL of reaction mixture, and transcript yield for each condition was quantitated from UV-shadowing of the PAGE-gel analysis using ImageQuant version 5.2 software (Molecular Dynamics). FIG. 8 summarizes the quantitated results of the PAGE-gel analysis, showing the fold-increase of transcript yield with of each condition relative to background. Based on the cost of 2'-OMe NTPs, and the results of this experiment, 1.5 mM each 2'-OMe NTP (and 8 mM MgCl$_2$, 2.5 mM MnCl$_2$) was adopted as the preferred conditions to use with the leader sequences and the Y639L/H784A/K378R mutant T7 RNA polymerase of the present invention.

Example 4B

Fidelity and Bias of MNA Transcription Using Y639L/H784A/K378R Mutant T7 RNA Polymerase Additional experiments were performed to assess the fidelity and bias of MNA transcription using the Y639L/H784A/K378R mutant T7 RNA polymerase and no 2'-OH GTP. To test fidelity, a single cloned sequence identified by TR-SELEX™ selection (described in Example 1) was amplified by PCR, used to program a MNA transcription using the Y639L/H784A/K378R polymerase and no 2'-OH GTP, purified by PAGE, remaining DNA template was digested using RQ1 DNase (the absence of DNA template was then assayed by PCR) and the transcribed material was reverse-transcribed (Thermoscript, Invitrogen, Carlsbad, Calif.) and then amplified by PCR. This PCR product was sequenced and the statistics of deletions, insertions and substitutions was then calculated. Of the 1300 bases sequenced in this experiment, no deletions and insertions were observed, and three substitutions were observed (see FIG. 9). These numbers suggest that the sequence information encoded within a 30-nucleotide degenerate region would have a 93% chance of being faithfully transmitted to the next round of SELEX™, this number is so high that it exceeds that measured for wild-type RNA.

To test for nucleotide bias, library ARC2118 was transcribed under the following conditions: HEPES 200 mM, DTT 40 mM, spermidine 2 mM, Triton X-100 0.01%, ~200 nM template, 2'-OMe ATP, CTP, UTP, and GTP 1 mM each (no 2'-OH GTP), MgCl$_2$ (6.5 mM), MnCl$_2$ (2 mM), PEG-8000 w/v 10%, GMP 1 mM, inorganic pyrophosphatase 5 units/mL, Y639L/H784A/K378R mutant T7 RNA polymerase 200 nM, at 37° C. overnight, purified by PAGE, the remaining DNA template was digested using RQ1 DNase (the absence of DNA template was then assayed by PCR) and the transcribed material was reverse-transcribed and amplified using PCR before cloning and sequencing. 48 clones from the amplified library and 48 clones from the starting library were sequenced. The statistics of nucleotide occurrence in the degenerate region were examined to see if bias occurred. As indicated by FIG. 10, the percentage of nucleotide composition after transcription was very similar to the percentage of nucleotide composition of the starting library in which the percentage of each nucleotide (A, T, C and G) was approximately equal, indicating that no nucleotide bias occurs with the Y639L/H784A/K378R mutant T7 RNA polymerase is used for transcription.

Example 4C

Comparison of Transcriptional Yield with Various Leader Sequences

Templates 1 to 4:

To compare transcriptional yields using Y639L/H784A/K378R mutant T7 RNA polymerase with multiple different leader sequences, 4 templates comprising varying ratios of purines to pyrimidines in the leader sequence (positions 1 to 14 in SEQ ID NOs 126 to 129 below), were synthesized with different constant regions. The DNA templates were synthesized using an ABI EXPEDITE™ (Applied Biosystems, Foster City, Calif.) DNA synthesizer, and deprotected by standard methods. The sequences (shown in the 5' to 3') are as follows:

```
Template 1
GGGAGAATTCCGACCAGAAGCTTNNNNNNNNNNNN  (SEQ ID NO 126)

NNNNNNNNNNNNNNNNNNNNNNNNNNNNCATAT

GTGCGTCTACATGGATCCTCA

Template 2
GGGAGAGCGGAAGCCGTGCTGGGGCNNNNNNNNN  (SEQ ID NO 127)

NNNNNNNNNNNNNNNNNNNNNNNNNNNNNCA

TAACCCAGAGGTCGATGGATC

Template 3
GGGAGAGACAAGCTTGGGTCNNNNNNNNNNNNNN  (SEQ ID NO 128)

NNNNNNNNNNNNNNNNNNNNNNNNNAGAAGAGA

AAGAGAAGTTAATTAAGGATCCTCAG

Template 4
GGGAGAATTCCGACCACAAGNNNNNNNNNNNNNN  (SEQ ID NO 129)

NNNNNNNNNNNNNNNNNNNNNNNNNCATATGTG

CGTCTACATGGATCCTCA
```

The templates were amplified with their respective primers as indicated in below:

```
Template 1:
5' primer
TAATACGACTCACTATAGGGAGAATTCCGACCAG  (SEQ ID NO 130)

AAGCTT

3' primer
TGAGGATCCATGTAGACGCACATATG          (SEQ ID NO 131)

Template 2:
5' primer
TAATACGACTCACTATAGGGAGAGCGGAAGCCGT  (SEQ ID NO 149)

GCTGGGGCC

3' primer
GATCCATCGACCTCTGGGTTATG             (SEQ ID NO 132)

Template 3:
5' primer
TAATACGACTCACTATAGGGAGAGACAAGCTTGG  (SEQ ID NO 133)

GTC

3' primer
CTGAGGATCCTTAATTAACTTCTCTTTCTCTTCT  (SEQ ID NO 134)

Template 4:
5' primer
TAATACGACTCACTATAGGGAGAATTCCGACCAC  (SEQ ID NO 135)

AAG

3' primer
TGAGGATCCATGTAGACGCACATATG          (SEQ ID NO 148)
```

The templates were used in a 15 mL in vitro transcription reaction with T7 RNA polymerase (Y639L/H784A/K378R). Transcriptions were done using 200 mM Hepes, 40 mM DTT, 2 mM spermidine, 0.01% Triton X-100, 10% PEG-8000, 8 mM $MgCl_2$, 2.5 mM $MnCl_2$, 1.5 mM mCTP, 1.5 mM mUTP, 1.5 mM mGTP, 1.5 mM mATP, 1 mM GMP, 0.01 units/μL inorganic pyrophosphatase, and ~9 μg/ml T7 polymerase (Y639L/H784A/K378R) and 0.2 μM template DNA. The RNA was precipitated and purified on 10% denaturing PAGE. The RNA was eluted from the gel in 300 mM NaOAc, 20 mM EDTA overnight, precipitated and quantitated with a UV Spec. The yields did not differ greatly between the four leader sequences tested and are shown in Table 1A below.

TABLE 1A

| Pool | Yield (nmoles) |
|---|---|
| Pool 1 | 18.7 |
| Pool 2 | 17.4 |
| Pool 3 | 20.2 |
| Pool 4 | 27.8 |

Templates 5 to 8

As for Templates 1 to 4 above, transcriptional yields for multiple leader sequences was assessed. Four templates were synthesized with different constant regions. The DNA templates were synthesized using an ABI EXPEDITE™ (Applied Biosystems, Foster City, Calif.) DNA synthesizer, and deprotected by standard methods. The sequences (shown in the 5' to 3' direction) are as follows:

```
Template 5
GGGCCTTGTAGCGTGCATTCTTGNNNNNNNNNNNN  (SEQ ID NO 138)

NNNNNNNNNNNNNNNNNNNNNNCTAACATACTCCGAA

TCTGTCGAA

Template 6
GGAGCCTTCCTCCGGANNNNNNNNNNNNNNNNNNN  (SEQ ID NO 139)

NNNNNNNNNNNNNNNNNNNNNNNTCCGGTTTCCCG

AGCTT

Template 7
GGGAGACAAGAATAAACGCTCAANNNNNNNNNNNN  (SEQ ID NO 140)

NNNNNNNNNNNNNNNNNNNNNNNNNNNTTCGA

CAGGAGGCTCACAACAGGC

Template 8
GGGGAGTACAATAACCAGACATNNNNNNNNNNNN  (SEQ ID NO 150)

NNNNNNNNNNNNNNNNNNNGGATCGTTACGACTAG

CATCGATG
```

The templates were amplified with their respective primers:

```
Template 5
5' primer
TAATACGACTCACTATAGGGCCTTGTAGCGTGCA    (SEQ ID NO 151)

TTCTTG

3' primer
TTCGACAGATTCGGAGTATGTTAG              (SEQ ID NO 141)

Template 6
5' primer
TAATACGACTCACTATAGGAGCCTTCCTCCGGA     (SEQ ID NO 142)

3' primer
AAGCTCGGGAAACCGGA                     (SEQ ID NO 143)

Template 7
5' primer
TAATACGACTCACTATAGGGAGACAAGAATAAAC    (SEQ ID NO 144)

GCTCAA

3' primer
GCCTGTTGTGAGCCTCCTGTCGAA              (SEQ ID NO 145)

Template 8
5' primer
TAATACGACTCACTATAGGGGAGTACAATAACCA    (SEQ ID NO 146)

GACAT

3' primer
CATCGATGCTAGTCGTAACGATCC              (SEQ ID NO 147)
```

The templates were then used for a 0.5 mL in vitro transcription with T7 RNA polymerase (Y639L/H784A/K378R). Transcriptions were done using 200 mM Hepes, 40 mM DTT, 2 mM spermidine, 0.01% Triton X-100, 10% PEG-8000, 8 mM MgCl$_2$, 2.5 mM MnCl$_2$, 1.5 mM mCTP, 1.5 mM mUTP, 1.5 mM mGTP, 1.5 mM mATP, 1 mM GMP, 0.01 units/µL inorganic pyrophosphatase, and ~9 µg/ml T7 polymerase (Y639L/H784A/K378R) and 0.2 µM template DNA. The RNA was precipitated and loaded on 10% denaturing PAGE. The RNA visualized by UV absorbance on the gel. The yields did not differ greatly between the four leader sequences tested and are shown in Table IA below (Relative transcription yields given):

TABLE 1B

| Pool | Yield (relative to Pool 4) |
| --- | --- |
| Pool 1 | 80% |
| Pool 2 | 88% |
| Pool 3 | 130% |
| Pool 4 | 100% |

In particular embodiments, the above identified templates may be used in the transcription methods and/or aptamer selection methods of the invention.

Example 4D

MNA Transcription using
P266L/Y639L/H784A/K378R Mutant T7 RNA
Polymerase

The following DNA template and primers were used to program a polymerase chain reaction to generate a double-stranded transcription template. N indicates a degenerate position with an approximately equal probability of being each of ATGC, all sequences are listed in the 5' to 3' direction:

```
PCR Template (ARC2118)
TAATACGACTCACTATAGGGGAGTACAATAACGT    (SEQ ID NO 3)

TCTCGNNNNNNNNNNNNNNNNNNNNNNNNNNNNNN

NGGATCGTTACGACTAGCATCGATG

5'-primer
AAAAAAAAAAAAAAAAAAAAAAAAAATAATACG     (SEQ ID NO 115)

ACTCACTATAGGGGAGTACAATAACGTTCTCG

3'-primer
CATCGATGCTAGTCGTAACG                  (SEQ ID NO 116)
```

The resultant double-stranded transcription template was then used to program 200 uL transcription mixtures for each sample as follows: HEPES (200 mM), DTT (40 mM), Spermidine (2 mM), Triton X-100 (0.01%), MgCl$_2$ (8 mM), MnCl$_2$ (2.5 mM), PEG-8000 (10% w/v), 1.5 mM each of 2'-OMe NTP, GMP 1 mM, 100-200 nM transcription template, Inorganic Pyrophosphatase (1 unit), pH 7.5, the T7 mutant polymerase P266L/Y639L/H784A/K378R was diluted as indicated below. The transcription mixture was incubated at 37° C. overnight (16 h).

After incubation, the mixtures were precipitated with isopropanol, the resultant pellet was dissolved and quantitated using denaturing PAGE (12.5% acrylamide) for 60 min at 25 W. The samples were visualized and quantitated by UV shadow at 260 nm.

TABLE 2

Transcriptional Yield

| Enzyme | Enzyme Concentration | Normalized MNA Transcript Yield |
| --- | --- | --- |
| K378R/Y639L/H784A | 2.1 µg/ml | 100 |
| P266L/K378R/Y639L/H784A | 11 µg/ml | 130 |
| P266L/K378R/Y639L/H784A | 2.6 µg/ml | 65 |
| P266L/K378R/Y639L/H784A | 0.66 µg/ml | 13 |
| P266L/K378R/Y639L/H784A | 0.16 µg/ml | 8.3 |

Example 5

Aptamer Selection Using Y639L/H784A/K378R Mutant T7 RNA Polymerase

A selection was performed to identify aptamers to human Ang2 (hereinafter "h-Ang2") using a pool consisting of 2'-OMe purine and pyrimidine nucleotides (hereinafter "MNA"). The selection strategy yielded high affinity aptamers to specific for h-Ang2.

Human Ang2 was purchased from R&D Systems, Inc. (Minneapolis, Minn.). T7 RNA polymerase (Y639L/H784A/K378R) was expressed and purified as described in Example 3 above. 2'-OMe purine and pyrimidine nucleotides were purchased from TriLink BioTechnologies (San Diego, Calif.).

Selection of Ang2 Aptamer

Pool Preparation

A DNA template with the sequence 5'-TAATACGACT-CACTATAGGGGAGTACAATAACGT-TCTCGNNNNNNNNNNNNNNNNNN NNNNNNNNNNNNNGGATCGTTACGAC-TAGCATCGATG ARC2118 (SEQ ID NO 3) was synthesized using an ABI EXPEDITE™ (Applied Biosystems, Foster City, Calif.) DNA synthesizer, and deprotected by standard methods. The templates were amplified with the primers (5'-(GATCGATCGATCGATCGATCTAATAC-GACTCACTATAGGGGAGTACAATAACGTTC TCG-3') (SEQ ID NO 118) and (5'-CATCGATGCTAGTCGTAAC-GATCC-3') (SEQ ID NO 119) and then used as a template for in vitro transcription with T7 RNA polymerase (Y639L/H784A/K378R). Transcriptions were done using 200 mM Hepes, 40 mM DTT, 2 mM spermidine, 0.01% Triton X-100, 10% PEG-8000, 8 mM $MgCl_2$, 2.5 mM, $MnCl_2$, 1.5 mM mCTP, 1.5 mM mUTP, 1.5 mM mGTP, 1.5 mM mATP, 1 mM GMP, 0.01 units/µL inorganic pyrophosphatase, and ~9 µg/mL T7 polymerase (Y639L/H784A/K378R) and 0.5 µM template DNA to generate the ARC2118 mRmY pool.

Selection

The selection was initiated by incubating of 330 pmoles ($2 \times 10^4$ molecules) of MNA ARC 2118 pool with 100 pmoles of protein in a final volume of 100 µL selection buffer (1× Dulbecco's PBS (DPBS)) for 1 hr at room temperature. RNA-protein complexes and unbound RNA molecules were separated using a 0.45 micron nitrocellulose spin column (Schleicher and Schuell, Keene, N.H.). The column was pre-treated with KOH (Soak column filter in 1 mL 0.5M KOH, 15 min RT; spin through. Soak filter in 1 mL dH2O 5 min RT; spin through), washed 2×1 mL 1×PBS, and then the solution containing pool:Ang2 complexes was added to the column and centrifuged at 1500×g for 2 minutes. The filter was washed twice with 500 µL DPBS to remove non-specific binders. RNA was eluted by addition of 2×100 µL elution buffer (7 M urea, 100 mM sodium acetate, 3 mM EDTA, pre-heated to 95° C.) and then precipitated with ethanol. The RNA was reverse transcribed with the ThermoScript RT-PCR™ system (Invitrogen, Carlsbad, Calif.) according to the manufacturer's instructions using the primer SEQ ID NO 119. The cDNA was amplified by PCR with Taq polymerase (New England Biolabs, Beverly, Mass.) according to the manufacturer's instructions using SEQ ID NO 118 and SEQ ID NO 119. Templates were transcribed as described above for pool preparation and purified on a denaturing polyacrylamide gel.

Round 2 was performed with the same method as round 1. Rounds 3-12 were carried out with h-Ang2 immobilized on hydrophobic plates. Each round of selection was initiated by immobilizing 20 pmoles of h-Ang2 to the surface of a Nunc Maxisorp hydrophobic plate for 1 hour at room temperature in 100 µL of 1×DPBS. The plate was washed 5× with 120 µL DPBS then incubated with blocking buffer (1×DPBS, and 0.1 mg/mL BSA) for 1 hour. The supernatant was then removed and the wells were washed 5 times with 120 µL 1×DPBS. The pool RNA was incubated for 1 hour at room temperature in empty wells then for 1 hour in a well that had been previously blocked with 100 µL blocking buffer. From round 3 forward, the target-immobilized wells were blocked for 1 hour at room temperature in 100 µL blocking buffer (1×PBS, 0.1 mg/mL tRNA, 0.1 mg/mL ssDNA and 0.1 mg/mL BSA) before the positive selection step. In all cases, the pool RNA bound to immobilized h-Ang2 was reverse transcribed directly in the selection plate by the addition of reverse transcription ("RT") mix (3' primer, SEQ ID NO 119, and Thermoscript RT, Invitrogen, Carlsbad, Calif.) followed by incubation at 65° C. for 1 hour. The resulting cDNA was used as a template for PCR (Taq polymerase, New England Biolabs, Mass.) and transcription as described for round 1. Conditions for each round are in Table 3.

TABLE 3

Round Summary

| Round | Pool (nM) | Platform | Negative | Buffer | Competitor | Target (nM) |
|---|---|---|---|---|---|---|
| 1 | 3300 | KOH filter | None | 1X DPBS | None | 1000 |
| 2 | 1000 | KOH filter | KOH filter | 1X DPBS | None | 1000 |
| 3 | 1000 | Plate | Plate; BSA plate | 1X DPBS | None | 200 |
| 4 | 1000 | Plate | Plate; BSA plate | 1X DPBS | None | 200 |
| 5 | 1000 | Plate | Plate; BSA plate | 1X DPBS | None | 200 |
| 6 | 1000 | Plate | Plate; BSA plate | 1X DPBS | None | 200 |
| 7 | 1000 | Plate | Plate; BSA plate | 1X DPBS | None | 200 |
| 8 | 1000 | Plate | Plate; BSA plate | 1X DPBS | None | 200 |
| 9 | 1000 | Plate | Plate; BSA plate | 1X DPBS | 0.1 mg/mL tRNA | 200 |
| 10 | 1000 | Plate | Plate; BSA plate | 1X DPBS | 0.1 mg/mL tRNA | 200 |

TABLE 3-continued

| | | | Round Summary | | | |
|---|---|---|---|---|---|---|
| Round | Pool (nM) | Platform | Negative | Buffer | Competitor | Target (nM) |
| 11 | 1000 | Plate | Plate; BSA plate | 1X DPBS | 0.1 mg/mL tRNA | 200 |
| 12 | 1000 | Plate | Plate; BSA plate | 1X DPBS | 0.1 mg/mL tRNA | 200 |

MNA Aptamer Binding Analysis

Dot blot binding assays were performed throughout the selections to monitor the protein binding affinity of the pools. Trace $^{32}$P-endlabeled pool RNA was combined with h-Ang2 and incubated at room temperature for 30 minutes in DPBS buffer in a final volume of 30 μL. The mixture was applied to a dot blot apparatus (Minifold-1 Dot Blot, Acrylic, Schleicher and Schuell, Keene, N.H.), assembled (from top to bottom) with nitrocellulose, nylon, and gel blot membranes. RNA that is bound to protein is captured on the nitrocellulose filter; whereas the non-protein bound RNA is captured on the nylon filter. Enrichment for h-Ang2 binding was seen starting at round 9. Round 9, 10 and 12 pool templates were cloned using the TOPO TA cloning kit (Invitrogen, Carlsbad, Calif.) according to the manufacturer's instructions and 26 unique clones were chosen for chemical synthesis and dissociation constants ($K_D$) were determined. Briefly, the synthetic RNAs were 5'end labeled with γ-$^{32}$P ATP and $K_D$ values were determined using the dot blot assay and buffer conditions of 1×DPBS (w/Ca$^{2+}$ and Mg$^{2+}$) (Gibco, Catalog #14040, Invitrogen, Carlsbad, Calif.). $K_D$S were estimated fitting the data to the equation: fraction RNA bound=amplitude*(((Apt-Conc+[h-Ang2]+$K_D$)−SQRT((AptConc+[h-Ang2]+$K_D$)$^2$−4(AptConc*[h-Ang2])))/(2*AptConc))+background. Results are reported in Table 4 below.

Within the 26 unique sequences, 8 shared a similar motif and had similar binding and inhibitory activity. These sequences are identified as Family I. Family II comprises 2 sequences with a shared motif that had similar binding and inhibitory activities.

Analysis of MNA Aptamer Function
Elisa Assay

Some the aptamers were tested in an ELISA assay that was setup to measure their ability to interfere with Ang2 binding to the Tie2 receptor. To capture Tie2 receptor, 150 ng of Tie2-Fc (R&D systems 313-TI-100-CF, Minneapolis, Minn.) in 100 μL of PBS (pH 7.4) was put onto a 96-well Maxisorb plate (NUNC #446612, Rochester, N.Y.) and incubated overnight at 4° C. During the capture, 50 μL of various concentrations of synthetic RNA were mixed with 50 μL of 3.6 nM Ang2 (200 ng/mL) (R&D systems, 623-AN-025/CF, Minneapolis, Minn.) (in PBS with 0.2% BSA) with final Ang2 concentration at 1.8 nM (100 ng/mL) in PBS with 0.1% BSA and incubated at room temperature for 1 hour. The capture solution was removed after an overnight incubation and the plate was washed with 200 μL of TBST (25 mM Tris-HCl pH 7.5, 150 mM NaCl and 0.01% Tween 20) three times. The plate was then blocked with 200 μL TBST containing 5% nonfat dry milk for 30 minutes at room temperature. After blocking, the μplate was washed with 200 μL of TBST again three times at room temperature and synthetic RNA:Ang2 mixture was added to the plate and incubated at room temperature for 1 hours. The plate was then washed with 200 μL of TBST three times and 100 μL of biotinylated goat anti-Ang2 antibody (1:1000; R&D Systems BAF623, Minneapolis, Minn.) was added and incubated for 1 hour at room temperature. After three washes with 200 μL of TBST, 100 μL of HRP linked Streptavidin (1:200; R&D systems #DY998, Minneapolis, Minn.) was added and incubated at room temperature for 0.5 hours. Then, the plate was washed again with 200 μL of TBST three times and 100 μL of TMP solution (Pierce, #34028) was added and incubated in the dark at room temp for 5 minutes. A solution of 100 μL containing 2 N H$_2$SO$_4$ was added to stop the reaction and the plate was read by SpectroMax at 450 nm. The results are given in the final column of Table 4 below.

FACS Assay

Human umbilical vein endothelial cell ("HUVEC") (ATCC) and K293 cell, a cell line overexpressing human Tie2 receptor, were used to determine the IC$_{50}$ of specific MNA Ang2 aptamers that inhibit binding of Ang2 to Tie2 receptor on the cell membrane. In brief, recombinant mammalian expression vector pCDNA3.1-Tie2 was transfected into 293 cells (ATCC, Manassas, Va.) and stable clones were then obtained after selection with G418 (Invitrogen, Carlsbad, Calif.). Flow cytometry demonstrated expression of Tie2 protein on both HUVEC and K293 cells. An Ang2 titration assay further determined the amounts of Ang2 (R&D Systems, Minneapolis, Minn.) for aptamer inhibition assay on HUVEC and K293 cells which were 1 and 0.1 μg/mL, respectively.

In the flow cytometry binding assay, HUVEC and K293 cells (2×10$^5$ cells/well) were pelleted in V bottomed 96-well plate and were subsequently resuspended and incubated in MNA aptamer/Ang2 solutions for 2 hours. Aptamer/Ang2 solutions were prepared by pre-incubation of different dosage of aptamers (100 nM, 33.3 nM, 11.1 nM, 3.7 nM, 1.2 nM, 0.411 nM, 0.137 nM, and 0.0456 nM) with Ang2 in FACs buffer (1% BSA, 0.2% sodium azide in PBS) for 30 min on ice. After three washes with FACs buffer, cells were incubated 30 minutes with biotinylated anti-human Ang2 antibody (5 μg/mL; R&D Systems, Minneapolis, Minn.), followed by another 30 minute incubation with Streptavidin PE (1:10; BD Biosciences, San Jose, Calif.). FACS analysis was completed using FACScan (BD Biosciences, San Jose, Calif.). The results are reported in Table 4 below.

TABLE 4

Summary of binding and functional results for anti-Ang2 MNA aptamers

| MNA Aptamer | Selection Round | Family | $K_D$ (nM) | IC$_{50}$ (293-Tie2 FACs) (nM) | IC$_{50}$ ELISA (nM) |
|---|---|---|---|---|---|
| 1 | 10 & 12 | I | 0.7 | 0.7 | Not tested |
| 2 | 10 & 12 | I | Not tested | 0.5 | Not tested |
| 3 | 12 | I | 0.2 | 0.5 | Not tested |
| 4 | 10 & 12 | I | 20.0 | 1.0 | Not tested |
| 5 | 12 | I | 34.0 | 0.7 | Not tested |
| 6 | 10 & 12 | I | 9.0 | 0.5 | 1.0 |
| 7 | 12 | I | 17.0 | 0.5 | 0.3 |
| 8 | 10 | II | 19.0 | 1.6 | 1.5 |
| 9 | 10 | I | 120.0 | Not tested | Not tested |

TABLE 4-continued

Summary of binding and functional results for anti-Ang2 MNA aptamers

| MNA Aptamer | Selection Round | Family | $K_D$ (nM) | $IC_{50}$ (293-Tie2 FACs) (nM) | $IC_{50}$ ELISA (nM) |
|---|---|---|---|---|---|
| 10 | 12 | I | 70.0 | Not tested | Not tested |
| 11 | 12 | I | No binding | Not tested | Not tested |
| 12 | 12 | I | 170.0 | Not tested | Not tested |
| 13 | 12 | I | 82.0 | Not tested | Not tested |
| 14 | 12 | I | No binding | Not tested | Not tested |
| 15 | 12 | I | No binding | Not tested | Not tested |
| 16 | 12 | I | No binding | No Inhibition | Not tested |
| 17 | 12 | I | 20.0 | No Inhibition | Not tested |
| 18 | 12 | I | 90.0 | Not tested | Not tested |
| 19 | 12 | II | 25.0 | 1.1 | 2.4 |
| 20 | 12 | I | No binding | No Inhibition | Not tested |
| 21 | 12 | I | 2.9 | 0.5 | Not tested |
| 22 | 12 | I | 17.0 | 0.6 | Not tested |
| 23 | 12 | I | No binding | Not tested | Not tested |
| 24 | 12 | I | No binding | Not tested | Not tested |
| 25 | 12 | I | No binding | No Inhibition | Not tested |
| 26 | 12 | I | No binding | Not tested | Not tested |

Example 6

Aptamer Selection Using Y639L/H784A/K378R Mutant T7 RNA Polymerase

A selection was performed to identify aptamers to human IgE (hereinafter "h-IgE") using a pool consisting of 2'-OMe purine and pyrimidine nucleotides (hereinafter "mRmY"). The selection strategy yielded high affinity aptamers specific for h-IgE.

Human IgE was purchased from Athens Research & Technology (Cat. #16-16-090705 Athens, Ga.). T7 RNA polymerase (Y639L/H784A/K378R) was expressed and purified as described in Example 3 above. 2'-OMe purine and pyrimidine nucleotides were purchased from TriLink BioTechnologies (San Diego, Calif.).

Selection of IgE Aptamer
Pool Preparation

A DNA template with the sequence 5'-TAATACGACT-CACTATAGGGGAGTACAATAACGT-TCTCGNNNNNNNNNNNNNNNNNN NNNNNNNNNNNNNGGATCGTTACGAC-TAGCATCGATG-3' ARC2118 (SEQ ID NO 3) was synthesized using an ABI EXPEDITE™ (Applied Biosystems, Foster City, Calif.) DNA synthesizer, and deprotected by standard methods. The templates were amplified with the primers (5'-(GATCGATCGATCGATCGATCTAATAC-GACTCACTATAGGGGAGTACAATAACGTTC TCG-3') (SEQ ID NO 118) and (5'-CATCGATGCTAGTCGTAAC-GATCC-3') (SEQ ID NO 119) and then used as a template for in vitro transcription with T7 RNA polymerase (Y639L/H784A/K378R). Transcriptions were done using 50 mM HEPES, 10 mM DTT, 0.5 mM spermidine, 0.0025% Triton X-100, 10% PEG-8000, 8 mM MgCl$_2$, 2.5 mM MnCl$_2$, 1.5 mM mCTP, 1.5 mM mUTP, 1.5 mM mGTP, 1.5 mM mATP, 1 mM GMP, 0.01 units/µL inorganic pyrophosphatase, and ~9 µg/mL mutant T7 polymerase (Y639L/H784A/K378R) and 0.3 µM template DNA to generate the ARC2118 MNA pool Selection The selection was initiated by incubating of 330 pmoles ($2 \times 10^{14}$ molecules) of MNA ARC 2118 pool with 24 pmoles of protein bound to a BSA-blocked hydrophobic plate (Maxisorp plate, Nunc, Rochester, N.Y.) in a final volume of 100 µL selection buffer (1× Dulbecco's PBS (DPBS) for 1 hr at room temperature. The well was washed four times with 120 µL DPBS to remove non-specific binders. RNA was eluted and reverse transcribed with the ThermoScript RT-PCR™ system (Invitrogen, Carlsbad, Calif.) according to the manufacturer's instructions using the primer SEQ ID NO 119. The cDNA was amplified by PCR with Taq polymerase (New England Biolabs, Beverly, Mass.) according to the manufacturer's instructions using SEQ ID NO 118 and SEQ ID NO 119. Templates were transcribed as described above for pool preparation and purified on a denaturing polyacrylamide gel.

All rounds were carried out with h-IgE immobilized on hydrophobic plates. Each round of selection was initiated by immobilizing 24 pmoles of h-IgE to the surface of a Nunc Maxisorp hydrophobic plate for 1 hour at room temperature in 100 µL of 1×DPBS. The plate was washed four times with 120 µL DPBS then incubated with blocking buffer (1×DPBS, and 0.1 mg/mL BSA) for 1 hour. The supernatant was then removed and the wells were washed four times with 120 µL 1×DPBS. Starting at Round 2, the pool RNA was incubated for 1 hour at room temperature in empty wells then for 1 hour in a well that had been previously blocked with 100 µL blocking buffer. From Round 2 forward, non-specific competitor was added to the positive selection step (0.1 mg/mL tRNA, and 0.1 mg/mL ssDNA). In all cases, the pool RNA bound to immobilized h-IgE was reverse transcribed directly in the selection plate by the addition of reverse transcription ("RT") mix (3' primer, SEQ ID NO 119, and Thermoscript RT, Invitrogen, Carlsbad, Calif.) followed by incubation at 65° C. for 1 hour. The resulting cDNA was used as a template for PCR (Taq polymerase, New England Biolabs, Beverly, Mass.) and transcription as described for round 1. Conditions for each round are in Table 5.

TABLE 5

Round Summary

| Round | Pool (nM) | Platform | Negative | Buffer | Competitor | Washes | Target |
|---|---|---|---|---|---|---|---|
| 1 | 3300 | Plate | None | 1X DPBS | None | 4 × 120 µL | 24 pmols |
| 2 | 500 | Plate | Plate; BSA plate | 1X DPBS | 0.1 mg/mL tRNA; 0.1 mg/mL ssDNA | 4 × 120 µL | 24 pmols |
| 3 | 1000 | Plate | Plate; BSA plate | 1X DPBS | 0.1 mg/mL tRNA; 0.1 mg/mL ssDNA | 4 × 120 µL | 24 pmols |

TABLE 5-continued

Round Summary

| Round | Pool (nM) | Platform | Negative | Buffer | Competitor | Washes | Target |
|---|---|---|---|---|---|---|---|
| 4 | 1000 | Plate | Plate; BSA plate | 1X DPBS | 0.1 mg/mL tRNA; 0.1 mg/mL ssDNA | 4 × 120 µL | 24 pmols |
| 5 | 1000 | Plate | Plate; BSA plate | 1X DPBS | 0.1 mg/mL tRNA; 0.1 mg/mL ssDNA | 4 × 120 µL | 24 pmols |
| 6 | 1000 | Plate | Plate; BSA plate | 1X DPBS | 0.1 mg/mL tRNA; 0.1 mg/mL ssDNA | 4 × 120 µL | 24 pmols |
| 7 | 1000 | Plate | Plate; BSA plate | 1X DPBS | 0.1 mg/mL tRNA; 0.1 mg/mL ssDNA | 4 × 120 µL | 24 pmols |
| 8 | 1000 | Plate | Plate; BSA plate | 1X DPBS | 0.1 mg/mL tRNA; 0.1 mg/mL ssDNA | 4 × 120 µL | 24 pmols |
| 9 | 1000 | Plate | Plate; BSA plate | 1X DPBS | 0.1 mg/mL tRNA; 0.1 mg/mL ssDNA | 4 × 120 µL | 24 pmols |
| 10 | 1000 | Plate | Plate; BSA plate | 1X DPBS | 1.0 mg/mL tRNA; 1.0 mg/mL ssDNA | 8 × 120 µL (last wash = 15 min.) | 24 pmols |
| 11 | 500 | Plate | Plate; BSA plate | 1X DPBS | 1.0 mg/mL tRNA; 1.0 mg/mL ssDNA | 8 × 120 µL (last wash = 15 min.) | 24 pmols |
| 12 | 500 | Plate | Plate; BSA plate | 1X DPBS | 1.0 mg/mL tRNA; 1.0 mg/mL ssDNA | 8 × 120 µL (last wash = (15 min.) | 24 pmols |

MNA Aptamer Binding Analysis

Dot blot binding assays were performed throughout the selections to monitor the protein binding affinity of the pools. Trace 32P-endlabeled pool RNA was combined with h-IgE and incubated at room temperature for 30 minutes in DPBS buffer in a final volume of 30 µL. The mixture was applied to a dot blot apparatus (Minifold-1 Dot Blot, Acrylic, Schleicher and Schuell, Keene, N.H.), assembled (from top to bottom) with nitrocellulose, nylon, and gel blot membranes. RNA that is bound to protein is captured on the nitrocellulose filter; whereas the non-protein bound RNA is captured on the nylon filter. Enrichment for h-IgE binding was seen starting at Round 8. Round 5, 8 and 12 pool templates were cloned using the TOPO TA cloning kit (Invitrogen, Carlsbad, Calif.) according to the manufacturer's instructions. The sequencing data revealed that the Round 8 pool had converged on a single major clone that comprised 59% of the total sequences. This major clone and three possible minimers were chosen for chemical synthesis and dissociation constants (KD) were determined. Briefly, the synthetic RNAs were 5'end labeled with $\gamma$-$^{32}$P ATP and KD values were determined using the dot blot assay and buffer conditions of 1×DPBS (w/Ca2+ and Mg2+) (Gibco, Catalog #14040, Invitrogen, Carlsbad, Calif.). KDs were estimated fitting the data to the equation: fraction RNA bound=amplitude*(((AptConc+[h-IgE]+KD)−SQRT((AptConc+[h-IgE]+KD)2−4(AptConc*[h-IgE])))/(2*AptConc))+background. The major clone had a $K_D$ of about 800 pM. The best binding minimer, was also tested for binding to monkey IgE (m-IgE), but did not demonstrate cross-reactive binding to the monkey IgE protein. This lack of cross-reactivity for was also confirmed by ELISA. Minimers with an inverted dT on the 3' end, was used as the parent molecule for the medicinal chemistry process.

Medicinal Chemistry

Figure 11:
FIG. 11 is a schematic of a minimized MNA anti-IgE aptamer shown in the 5' to 3' direction having a cap on its 3'end (dark colored ball).
Figure 12:
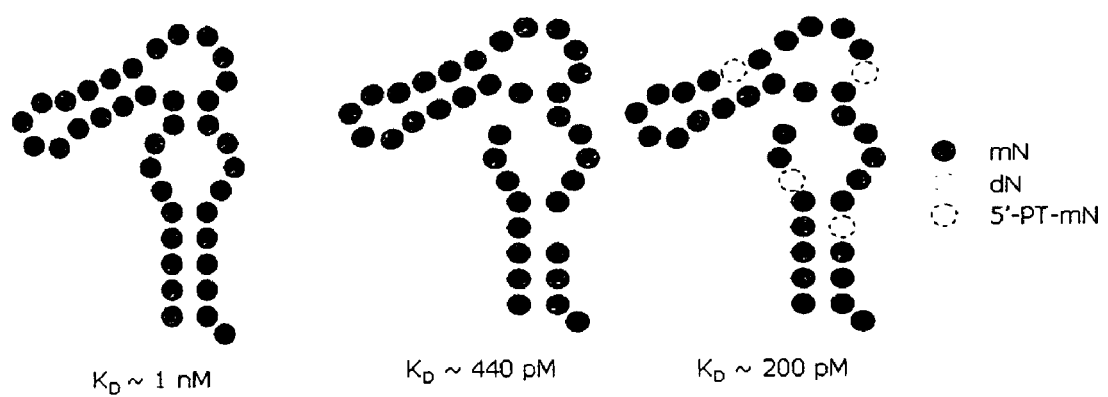
FIG. 12 is a schematic of the minimized MNA anti-IgE aptamer, the minimized MNA anti-IgE aptamer having two deoxy substitutions and the minimized MNA anti-IgE aptamer having one deoxy substitution and phosphorothioate substitutions, each shown in the 5' to 3' direction and each having a cap on its 3'end (black colored ball).

The chemical composition of one of the IgE specific MNA minimers (FIG. 11) was altered to improve affinity, and potency while maintaining plasma stability of the compound. The process included the design, synthesis and evaluation of a series of derivatives of the minimized IgE aptamer where each derivative of the series comprised a single modification at each occurrence of a predetermined nucleotide to determine which residues tolerated substitution. The first set of modifications was the substitution of a deoxy nucleotide for each unique 2'-OMe nucleotide. In a separate round of modification, a series of derivatives was synthesized in which each derivative comprised a single phosphorothioate modification at a different internucleotide linkage position. Data generated in these initial phases of modification were used to establish a structure activity relationship (SAR) for the minimized aptamer. In a subsequent phase of modification, aptamers were synthesized and tested with composite sets of substitutions that were designed based on the initial SAR data. From the panel of composite substitutions, an aptamer 39 nucleotides in length with two 2'-OMe to 2'-deoxy substitutions introduced into its composition, was identified. In addition, a resulting modified minimized aptamer, 39 nucleotides in length with one 2'-OMe to 2'-deoxy substitution and four phosphate to phosphorothioate substitutions incorporated into its composition, was identified. As shown in FIG. 12, this deoxy/phosphorothioate modified aptamer, demonstrates increased binding affinity compared to both the minimized but unmodified parent aptamer as well as the parent minimized aptamer having two deoxy for 2'-OMe substitutions.

Serum Stability

The minimized unmodified parent and the deoxy/phosphorothioate modified aptamer were assayed to determine their stability in human, rat and monkey serums. Each aptamer was added to 1 ml of pooled serum to a final concentration of 5 µM in 90% serum. The aptamers were incubated at 37° C. with shaking and time points were taken at 0, 0.5, 1, 4, 24, 48, 72, and 98 hours. At each time point, 90 µl of stock from the incubated samples was added to 10 µl of 0.5M EDTA and frozen at −20° C. for later stability analysis using a BIACORE 2000 system.

All biosensor binding measurements were performed at 25° C. using a BIACORE 2000 equipped with a research-grade CM5 biosensor chip (BIACORE Inc., Piscataway, N.J.). Purified recombinant human IgE (Athens Research & Technology, Athens, Ga.) was immobilized to the biosensor surface using amino-coupling chemistry. To achieve this, the surfaces of two flow cells were first activated for 7 min with a 1:1 mixture of 0.1 M NHS (Nhydroxysuccinimide) and 0.4 M EDC (3-(N,Ndimethylamine) propyl-N-ethylcarbodiimide) at a flow rate of 5 µl/min. After surface activation, one flow cell was injected with 50 µg/ml of IgE at 10 µl/min for 20 min to allow for establishment of covalent bonds to the activated surface. Next, 1 M ethanolamine hydrochloride pH 8.5 was injected for 7 min at 5 µl/min to inactivate residual esters. For flow cell used as blank, 1 M ethanolamine hydrochloride pH 8.5 was injected for 7 min to inactivate residual esters without protein injection.

A set of aptamer standards was run through the prepared chip to generate a standard curve before all the time-points were analyzed. To establish a standard curve, aptamers were serially diluted (from 200 nM to 12.5 nM) into HBS-P buffer (10 mM HEPES pH 7.4, 150 mM NaCl, 0.005% Surfactant 20) supplemented with 4% human serum and 50 mM EDTA. All diluted samples were injected into Biacore 2000 for binding at 20 μl/min for 5 min and wait for 3 minutes. To regenerate the chip, 1N NaCl was injected for 60 seconds at 30 μl/min. RU peak response at the end of binding phase was plotted against aptamer concentration and a standard curve was generated using a Four-Parameter logistic function. To measure the active aptamer concentration in human, rat, and monkey serums, time-point samples were diluted 22.5-fold in HBS-P to make the final serum concentration at 4% immediately prior to injection into the Biacore 2000. Functional aptamer concentrations at each serum incubation period were calculated by converting from RU response unit to concentration using standard curve generated above. As an additional quality control measure, two aptamer standards were independently tested at the end of experiment to make sure the BIACORE-measured concentrations are less than 20% deviated from standards. The minimized unmodified parent and the deoxy/phosphorothioate modified aptamer were both determined to be greater than 90% active at 98 hours in human, rat, and monkey serums.

The invention having now been described by way of written description and example, those of skill in the art will recognize that the invention can be practiced in a variety of embodiments and that the description and examples above are for purposes of illustration and not limitation of the following claims.

What is claimed is:

1. An isolated T7 RNA polymerase comprising mutations at amino acid positions 639 and 784 relative to the wild-type T7 RNA polymerase of SEQ ID NO: 121, wherein the amino acid at position 639 is changed to a leucine, and the amino acid at position 784 is changed to an alanine.

2. The isolated T7 RNA polymerase of claim 1, further comprising a mutation at amino acid position 266 relative to the wild-type T7 RNA polymerase of SEQ ID NO: 121, wherein the amino acid at position 266 is changed to a leucine.

3. The isolated T7 RNA polymerase of claim 1, further comprising a mutation at amino acid position 378 relative to the wild-type T7 RNA polymerase of SEQ ID NO: 121, wherein the amino acid at position 378 is changed to an arginine.

4. The isolated T7 RNA polymerase of claim 1, wherein the mutations increase the transcriptional yield of nucleic acids comprising 2'-OMe modifications by the polymerase in a transcription reaction comprising only 2'-OMe nucleotide triphosphates.

5. The isolated T7 RNA polymerase of claim 4, wherein the increase in transcriptional yield is relative to the wild-type T7 RNA polymerase of SEQ ID NO: 121 when transcription is carried out under identical transcription conditions.

6. The isolated T7 RNA polymerase of claim 1, wherein the mutations decrease discrimination against 2'-OMe nucleotide triphosphates.

7. The isolated T7 RNA polymerase of claim 6, wherein the decreased discrimination against 2'-OMe nucleotide triphosphates is relative to the wild-type T7 RNA polymerase of SEQ ID NO: 121.

8. An isolated polypeptide comprising the amino acid sequence of SEQ ID NO: 1.

9. A kit comprising a container comprising the isolated T7 RNA polymerase of claim 1 or the isolated polypeptide of claim 8.

10. The isolated T7 RNA polymerase of claim 1, further comprising mutations at amino acid positions 266 and 378 relative to the wild-type T7 RNA polymerase of SEQ ID NO: 121, wherein the amino acid at position 266 is changed to a leucine, and the amino acid at position 378 is changed to an arginine.

11. An isolated T7 RNA polymerase comprising mutations at amino acid positions 639 and 784 relative to the wild-type T7 RNA polymerase of SEQ ID NO: 121, wherein the amino acid at position 639 is changed to a leucine, and the amino acid at position 784 is changed to an alanine, and wherein the mutations increase the transcriptional yield of nucleic acids comprising 2'-OMe modifications by the polymerase.

* * * * *

SEQUENCE LISTING

<160> NUMBER OF SEQ ID NOS: 151

<210> SEQ ID NO 1
<211> LENGTH: 883
<212> TYPE: PRT
<213> ORGANISM: Artificial Sequence
<220> FEATURE:
<223> OTHER INFORMATION: chemically synthesized modified T7 polymerase Y639/H784A

<400> SEQUENCE: 1

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240
```

```
Ser Glu Thr Ile Glu Leu Ala Pro Glu Tyr Ala Glu Ala Ile Ala Thr
            245                 250                 255
Arg Ala Gly Ala Leu Ala Gly Ile Ser Pro Met Phe Gln Pro Cys Val
        260                 265                 270
Val Pro Pro Lys Pro Trp Thr Gly Ile Thr Gly Gly Gly Tyr Trp Ala
    275                 280                 285
Asn Gly Arg Arg Pro Leu Ala Leu Val Arg Thr His Ser Lys Lys Ala
290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
            325                 330                 335
Val Ala Asn Val Ile Thr Lys Trp Lys His Cys Pro Val Glu Asp Ile
        340                 345                 350
Pro Ala Ile Glu Arg Glu Glu Leu Pro Met Lys Pro Glu Asp Ile Asp
    355                 360                 365
Met Asn Pro Glu Ala Leu Thr Ala Trp Lys Arg Ala Ala Ala Ala Val
370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
            405                 410                 415
Pro Tyr Asn Met Asp Trp Arg Gly Arg Val Tyr Ala Val Ser Met Phe
        420                 425                 430
Asn Pro Gln Gly Asn Asp Met Thr Lys Gly Leu Leu Thr Leu Ala Lys
    435                 440                 445
Gly Lys Pro Ile Gly Lys Glu Gly Tyr Tyr Trp Leu Lys Ile His Gly
450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
            485                 490                 495
Leu Glu Asn Thr Trp Trp Ala Glu Gln Asp Ser Pro Phe Cys Phe Leu
        500                 505                 510
Ala Phe Cys Phe Glu Tyr Ala Gly Val Gln His His Gly Leu Ser Tyr
    515                 520                 525
Asn Cys Ser Leu Pro Leu Ala Phe Asp Gly Ser Cys Ser Gly Ile Gln
530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
            565                 570                 575
Lys Val Asn Glu Ile Leu Gln Ala Asp Ala Ile Asn Gly Thr Asp Asn
        580                 585                 590
Glu Val Val Thr Val Thr Asp Glu Asn Thr Gly Glu Ile Ser Glu Lys
    595                 600                 605
Val Lys Leu Gly Thr Lys Ala Leu Ala Gly Gln Trp Leu Ala Tyr Gly
610                 615                 620
Val Thr Arg Ser Val Thr Lys Arg Ser Val Met Thr Leu Ala Leu Gly
625                 630                 635                 640
Ser Lys Glu Phe Gly Phe Arg Gln Gln Val Leu Glu Asp Thr Ile Gln
            645                 650                 655
Pro Ala Ile Asp Ser Gly Lys Gly Leu Met Phe Thr Gln Pro Asn Gln
```

```
              660                 665                 670
Ala Ala Gly Tyr Met Ala Lys Leu Ile Trp Glu Ser Val Ser Val Thr
                675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val Ala
            770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 2
<211> LENGTH: 883
<212> TYPE: PRT
<213> ORGANISM: Artificial Sequence
<220> FEATURE:
<223> OTHER INFORMATION: chemically synthesized modified T7 polymerase
      Y639L/H784A/K378R

<400> SEQUENCE: 2

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140
```

-continued

```
Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Arg Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
```

565                 570                 575
Lys Val Asn Glu Ile Leu Gln Ala Asp Ala Ile Asn Gly Thr Asp Asn
                580                 585                 590

Glu Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Leu Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val Ala
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 3
<211> LENGTH: 93
<212> TYPE: DNA
<213> ORGANISM: Artificial Sequence
<220> FEATURE:
<223> OTHER INFORMATION: chemically synthesized DNA transcription
      template ARC 2118
<220> FEATURE:
<221> NAME/KEY: misc_feature
<222> LOCATION: (40)..(69)
<223> OTHER INFORMATION: n is a, t, c or g

<400> SEQUENCE: 3
taatacgact cactataggg gagtacaata acgttctcgn nnnnnnnnn nnnnnnnnnn     60 nnnnnnnnng gatcgttacg actagcatcg atg                                 93

<210> SEQ ID NO 4
<211> LENGTH: 93
<212> TYPE: DNA
<213> ORGANISM: Artificial Sequence
<220> FEATURE:
<223> OTHER INFORMATION: chemically synthesized DNA transcription
      template ARC 2119
<220> FEATURE:
<221> NAME/KEY: misc_feature
<222> LOCATION: (40)..(69)
<223> OTHER INFORMATION: n is a, t, c or g

<400> SEQUENCE: 4
taatacgact cactataggg ggtgatattg acgttctcgn nnnnnnnnn nnnnnnnnnn    60 nnnnnnnnng gatcgttacg actagcatcg atg                               93

<210> SEQ ID NO 5
<211> LENGTH: 93
<212> TYPE: DNA
<213> ORGANISM: Artificial Sequence
<220> FEATURE:
<223> OTHER INFORMATION: chemically synthesized DNA transcription
      template ARC 2120
<220> FEATURE:
<221> NAME/KEY: misc_feature
<222> LOCATION: (40)..(69)
<223> OTHER INFORMATION: n is a, t, c or g

<400> SEQUENCE: 5
taatacgact cactataggg gtgcgcggtt acgttctcgn nnnnnnnnn nnnnnnnnnn    60 nnnnnnnnng gatcgttacg actagcatcg atg                               93

<210> SEQ ID NO 6
<211> LENGTH: 93
<212> TYPE: DNA
<213> ORGANISM: Artificial Sequence
<220> FEATURE:
<223> OTHER INFORMATION: chemically synthesized DNA transcription
      template ARC 2121
<220> FEATURE:
<221> NAME/KEY: misc_feature
<222> LOCATION: (40)..(69)
<223> OTHER INFORMATION: n is a, t, c or g

<400> SEQUENCE: 6
taatacgact cactataggg ggaggggtg ccgttctcgn nnnnnnnnn nnnnnnnnnn     60 nnnnnnnnng gatcgttacg actagcatcg atg                               93

<210> SEQ ID NO 7
<211> LENGTH: 81
<212> TYPE: DNA
<213> ORGANISM: Artificial Sequence
<220> FEATURE:
<223> OTHER INFORMATION: chemically synthesized DNA transcription
      template ARC1140
<220> FEATURE:
<221> NAME/KEY: misc_feature
<222> LOCATION: (22)..(41)
<223> OTHER INFORMATION: n is a, t, c or g

<400> SEQUENCE: 7
taatacgact cactataggg gnnnnnnnnn nnnnnnnnnn nacgtaaccg gttaaacccg   60
ggtcgatgca gtaagctagc t                                            81

<210> SEQ ID NO 8
<211> LENGTH: 17
<212> TYPE: DNA

```
<213> ORGANISM: Artificial Sequence
<220> FEATURE:
<223> OTHER INFORMATION: chemically synthesized 5'-phosphorylated T7
      promoter oligonucleotide
<220> FEATURE:
<221> NAME/KEY: modified_base
<222> LOCATION: (1)..(1)
<223> OTHER INFORMATION: where thymidine at position 1 is
      5'-phosphorylated

<400> SEQUENCE: 8
tatagtgagt cgtatta                                                        17

<210> SEQ ID NO 9
<211> LENGTH: 21
<212> TYPE: DNA
<213> ORGANISM: Artificial Sequence
<220> FEATURE:
<223> OTHER INFORMATION: chemically synthesized ligation splint

<400> SEQUENCE: 9
taatacgact cactataggg g                                                   21

<210> SEQ ID NO 10
<211> LENGTH: 82
<212> TYPE: DNA
<213> ORGANISM: Artificial Sequence
<220> FEATURE:
<223> OTHER INFORMATION: chemically synthesized sequence

<400> SEQUENCE: 10
taatacgact cactataggg ggtggggcca atggcgggat atacgtaacc ggttataccc         60
gggtcgatgc agtaagctag ct                                                 82

<210> SEQ ID NO 11
<211> LENGTH: 80
<212> TYPE: DNA
<213> ORGANISM: Artificial Sequence
<220> FEATURE:
<223> OTHER INFORMATION: chemically synthesized sequence

<400> SEQUENCE: 11
taatacgact cactataggg gatgtacata tgtattcgtg acgtgaccgg ttaaacccgg         60
gtcgatgcag taagctagct                                                    80

<210> SEQ ID NO 12
<211> LENGTH: 82
<212> TYPE: DNA
<213> ORGANISM: Artificial Sequence
<220> FEATURE:
<223> OTHER INFORMATION: chemically synthesized sequence

<400> SEQUENCE: 12
taatacgact cactataggg ggagcgggga gacgtagtca tcacgtagcc ggttaaaccc         60
gggtcgatgc agtaagctag ct                                                 82

<210> SEQ ID NO 13
<211> LENGTH: 79
<212> TYPE: DNA
<213> ORGANISM: Artificial Sequence
<220> FEATURE:
<223> OTHER INFORMATION: chemically synthesized sequence
<220> FEATURE:
<221> NAME/KEY: misc_feature
<222> LOCATION: (7)..(7)
<223> OTHER INFORMATION: n is a, c, g, or t
```

-continued

```
<400> SEQUENCE: 13
taatacnact cactataggg ggtgggggtg gtggtgataa cgtaaccggt taaacccggg      60
tcgatgcagt aagctagct                                                  79

<210> SEQ ID NO 14
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 14
taatacgact cactataggg gggtgtcacc agatatgcct tgaacgtaac ccgttaaacc      60
cgggtcgatg cagtaagcta gct                                             83

<210> SEQ ID NO 15
<211> LENGTH: 82
<212> TYPE: DNA
<213> ORGANISM: Artificial Sequence
<220> FEATURE:
<223> OTHER INFORMATION: chemically synthesized sequence

<400> SEQUENCE: 15
taatacgact cactataggg ggtaggggggc acgcactaac caacgtaacc ggttaaaccc     60
gggtcgatgc agtaagctag ct                                              82

<210> SEQ ID NO 16
<211> LENGTH: 43
<212> TYPE: DNA
<213> ORGANISM: Artificial Sequence
<220> FEATURE:
<223> OTHER INFORMATION: chemically synthesized sequence
<220> FEATURE:
<221> NAME/KEY: misc_feature
<222> LOCATION: (37)..(37)
<223> OTHER INFORMATION: n is a, c, g, or t

<400> SEQUENCE: 16
taatacgact cactataggg ggagggggtg ctgaccncaa aca                       43

<210> SEQ ID NO 17
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 17
taatacgact cactataggg gtggggctcg gatgagacaa tacgtaaccg gttaaacccg      60
ggtcgatgca gtaagctagc t                                               81

<210> SEQ ID NO 18
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 18
taatacgact cactataggg gggggtgggt aggcgagcac tccacgtaac cagttaaacc      60
cgggtcgatg cagtaagcta gct                                             83

<210> SEQ ID NO 19
```

```
<211> LENGTH: 82
<212> TYPE: DNA
<213> ORGANISM: Artificial Sequence
<220> FEATURE:
<223> OTHER INFORMATION: chemically synthesized sequence

<400> SEQUENCE: 19
taatacgact cactataggg gggaaggacg agcagacgag caacgtaacc tgttaaaccc      60
gggtcgatgc agtaagctag ct                                              82

<210> SEQ ID NO 20
<211> LENGTH: 85
<212> TYPE: DNA
<213> ORGANISM: Artificial Sequence
<220> FEATURE:
<223> OTHER INFORMATION: chemically synthesized sequence

<400> SEQUENCE: 20
taatacgact cactataggg gggggcggtt agagtgtaag taccgacgta accggttaaa      60
cccgggtcga tgcagtaagc tagct                                           85

<210> SEQ ID NO 21
<211> LENGTH: 79
<212> TYPE: DNA
<213> ORGANISM: Artificial Sequence
<220> FEATURE:
<223> OTHER INFORMATION: chemically synthesized sequence

<400> SEQUENCE: 21
taatacgact cactataggg gggttgctgt tagtaacgcc acgtaaccgg ttaaacttgg      60
tcgatgcagt aagctagct                                                  79

<210> SEQ ID NO 22
<211> LENGTH: 84
<212> TYPE: DNA
<213> ORGANISM: Artificial Sequence
<220> FEATURE:
<223> OTHER INFORMATION: chemically synthesized sequence

<400> SEQUENCE: 22
taatacgact cactataggg gggcgggaga atgttatata gttacggtaa ccggttaaac      60
ccgggtcgat gcagtaagct agct                                            84

<210> SEQ ID NO 23
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 23
taatacgact cactataggg gaaaggggcg gtatggtaca cacgtaacag gttaaacccg      60
ggtcgatgca gtaagctagc t                                               81

<210> SEQ ID NO 24
<211> LENGTH: 80
<212> TYPE: DNA
<213> ORGANISM: Artificial Sequence
<220> FEATURE:
<223> OTHER INFORMATION: chemically synthesized sequence

<400> SEQUENCE: 24
taatacgact cactataggg gggacgtgtt agcattccag aattcgtaac ctaaacccgg      60
```

```
gtcgatgcag taagctagct                                               80

<210> SEQ ID NO 25
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 25
taatacgact cactataggg ggcgtgggag ataggttcaa ggacgtaccg gttatacccg   60
ggtcgatgca gtaagctagc t                                            81

<210> SEQ ID NO 26
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 26
taatacgact cactataggg gggctccgtg ctatcgtcgg ataacgtaac ccgttaaacc   60
cgggtcgatg cagtaagcta gct                                          83

<210> SEQ ID NO 27
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 27
taatacgact cactataggg ggggagaagg tcttaaggtc gccaacgtaa ctgttaaacc   60
cgggtcgatg cagtaagcta gct                                          83

<210> SEQ ID NO 28
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 28
taatacgact cactataggg ggggcatacg agtttaggtg gagacgtaac cggttaaacc   60
cgggtcgatg cagtaagcta gct                                          83

<210> SEQ ID NO 29
<211> LENGTH: 82
<212> TYPE: DNA
<213> ORGANISM: Artificial Sequence
<220> FEATURE:
<223> OTHER INFORMATION: chemically synthesized sequence

<400> SEQUENCE: 29
taatacgact cactataggg ggatgatgac ttccgcgtta atacgttacc ggttaaaccc   60
gggtcgatgc agtaagctag ct                                           82

<210> SEQ ID NO 30
<211> LENGTH: 75
<212> TYPE: DNA
<213> ORGANISM: Artificial Sequence
<220> FEATURE:
<223> OTHER INFORMATION: chemically synthesized sequence
```

-continued

```
<400> SEQUENCE: 30
taatacgact cactataggg gtgggacgcc gtctgagtat aacgtacccg gtcgggtcga    60
tgcagtaagc tagct                                                    75

<210> SEQ ID NO 31
<211> LENGTH: 87
<212> TYPE: DNA
<213> ORGANISM: Artificial Sequence
<220> FEATURE:
<223> OTHER INFORMATION: chemically synthesized sequence

<400> SEQUENCE: 31
taatacgact cactataggg ggggggggac gtaatcggct atcgttcacg taaccggtta    60
aacccgggtc gatgcagtaa agggcga                                       87

<210> SEQ ID NO 32
<211> LENGTH: 84
<212> TYPE: DNA
<213> ORGANISM: Artificial Sequence
<220> FEATURE:
<223> OTHER INFORMATION: chemically synthesized sequence

<400> SEQUENCE: 32
taatacgact cactataggg tgggacgggc agcgtggatg taggacgtaa ccggttaaac    60
gcgggtcgat gcagtaagct agct                                          84

<210> SEQ ID NO 33
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 33
taatacgact cactataggg gggtttgtct gaagtgaagc agaacgtaac cggttaatcc    60
cgggtcgatg cagtaagcta gct                                           83

<210> SEQ ID NO 34
<211> LENGTH: 84
<212> TYPE: DNA
<213> ORGANISM: Artificial Sequence
<220> FEATURE:
<223> OTHER INFORMATION: chemically synthesized sequence

<400> SEQUENCE: 34
taatacgact cactataggg ggggagggca catcatcgta tcaaacgtaa ccagttaatc    60
ccgggtcgat gcagtaagct agct                                          84

<210> SEQ ID NO 35
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 35
taatacgact cactataggg gaggctagag gacgcgacag aacgtaaccg gttaaacccg    60
ggtcgatgca gtaagctagc t                                             81

<210> SEQ ID NO 36
<211> LENGTH: 81
<212> TYPE: DNA
```

```
<213> ORGANISM: Artificial Sequence
<220> FEATURE:
<223> OTHER INFORMATION: chemically synthesized sequence

<400> SEQUENCE: 36
taatacgact cactataggg ggcgatcgcg aagggatttc aacgtaaccg gttaaacccg    60
ggtcgatgca gtaagctagc t                                             81

<210> SEQ ID NO 37
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 37
taatacgact cactataggg gggtagggaa agattacggg gctacgtaac cggttatacc    60
tgggtcgatg cagtaagcta gct                                           83

<210> SEQ ID NO 38
<211> LENGTH: 75
<212> TYPE: DNA
<213> ORGANISM: Artificial Sequence
<220> FEATURE:
<223> OTHER INFORMATION: chemically synthesized sequence

<400> SEQUENCE: 38
taatacgact cactataggg gtggctatgg ctaacacgta accggttata cccgggtcga    60
tgcagtaagc tagct                                                    75

<210> SEQ ID NO 39
<211> LENGTH: 86
<212> TYPE: DNA
<213> ORGANISM: Artificial Sequence
<220> FEATURE:
<223> OTHER INFORMATION: chemically synthesized sequence

<400> SEQUENCE: 39
taatacgact cactataggg gggggcggt ggctgtgcaa gcggaaacgt aaccggttaa    60
acccgggtcg atgcagtaag ctagct                                       86

<210> SEQ ID NO 40
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 40
taatacgact cactataggg gggtgggggc acggtactga gttacgttac cggttaaacc    60
cgggtcgatg cagtaagcta gct                                           83

<210> SEQ ID NO 41
<211> LENGTH: 78
<212> TYPE: DNA
<213> ORGANISM: Artificial Sequence
<220> FEATURE:
<223> OTHER INFORMATION: chemically synthesized sequence

<400> SEQUENCE: 41
taatacgact cactataggg gggagtgggg acaattagaa gatgacgtaa ccgtccgggt    60
cgatgcagta agctagct                                                 78
```

```
<210> SEQ ID NO 42
<211> LENGTH: 81
<212> TYPE: DNA
<213> ORGANISM: Artificial Sequence
<220> FEATURE:
<223> OTHER INFORMATION: chemically synthesized sequence
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 42
taatacnact cactataggg gtgcagtgag gagcgacnag tacgttaccg gttaaatccg    60
agtcgatgca gtaagctagc t                                             81

<210> SEQ ID NO 43
<211> LENGTH: 83
<212> TYPE: DNA
<213> ORGANISM: Artificial Sequence
<220> FEATURE:
<223> OTHER INFORMATION: chemically synthesized sequence
<220> FEATURE:
<221> NAME/KEY: misc_feature
<222> LOCATION: (7)..(7)
<223> OTHER INFORMATION: n is a, c, g, or t

<400> SEQUENCE: 43
taatacnact cactataggg ggacgggcac tgtggatgat ttaacgttac cggttaaacc    60
cgagtcgatg cagtaagcta gct                                           83

<210> SEQ ID NO 44
<211> LENGTH: 40
<212> TYPE: DNA
<213> ORGANISM: Artificial Sequence
<220> FEATURE:
<223> OTHER INFORMATION: chemically synthesized sequence
<220> FEATURE:
<221> NAME/KEY: misc_feature
<222> LOCATION: (7)..(7)
<223> OTHER INFORMATION: n is a, c, g, or t

<400> SEQUENCE: 44
taatacnact cactataggg gtcgatgcag taagctagct                          40

<210> SEQ ID NO 45
<211> LENGTH: 81
<212> TYPE: DNA
<213> ORGANISM: Artificial Sequence
<220> FEATURE:
<223> OTHER INFORMATION: chemically synthesized sequence
<220> FEATURE:
<221> NAME/KEY: misc_feature
<222> LOCATION: (7)..(7)
<223> OTHER INFORMATION: n is a, c, g, or t

<400> SEQUENCE: 45
taatacnact cactataggg ggtgatattg acctctaaca gcacgtaacc ggttaaaccc    60
ggtcgatgca gtaagctagc t                                             81

<210> SEQ ID NO 46
<211> LENGTH: 79
<212> TYPE: DNA
<213> ORGANISM: Artificial Sequence
<220> FEATURE:
```

<223> OTHER INFORMATION: chemically synthesized sequence

<400> SEQUENCE: 46
taatacgact cactataggg ggggggtgc agaggatgca tccaagctcg taatcggtgg    60
tcgatgcagt aagctagct                                               79

<210> SEQ ID NO 47
<211> LENGTH: 84
<212> TYPE: DNA
<213> ORGANISM: Artificial Sequence
<220> FEATURE:
<223> OTHER INFORMATION: chemically synthesized sequence

<400> SEQUENCE: 47
taatacgact cactataggg gggggcgggt gcttgtgcct aatcacgtaa ccggttaaac    60
ccgggtcgat gcagtaagct agct                                         84

<210> SEQ ID NO 48
<211> LENGTH: 79
<212> TYPE: DNA
<213> ORGANISM: Artificial Sequence
<220> FEATURE:
<223> OTHER INFORMATION: chemically synthesized sequence

<400> SEQUENCE: 48
taatacgact cactataggg gtttggtaat cgaacgtgga acgcaaccgg tttaaccggg    60
tcgatgcagt aagctagct                                               79

<210> SEQ ID NO 49
<211> LENGTH: 82
<212> TYPE: DNA
<213> ORGANISM: Artificial Sequence
<220> FEATURE:
<223> OTHER INFORMATION: chemically synthesized sequence

<400> SEQUENCE: 49
taatacgact cactataggg gggatggaag aggcttgata tcacgtaacc ggttaaacct    60
gggtcgatgc agtaagctag ct                                           82

<210> SEQ ID NO 50
<211> LENGTH: 76
<212> TYPE: DNA
<213> ORGANISM: Artificial Sequence
<220> FEATURE:
<223> OTHER INFORMATION: chemically synthesized sequence

<400> SEQUENCE: 50
taatacgact cactataggg ggttatacta actctgtaca caacgtaacc ggccgggtcg    60
atgcagtaag ctagct                                                  76

<210> SEQ ID NO 51
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 51
taatacgact cactataggg gtataggggg ggtatcggtg tacgtaaccg gttaaacccg    60
ggtcgatgca gtaagctagc t                                            81

<210> SEQ ID NO 52

```
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 52
taatacgact cactataggg gagtacaata aggttccgag aacgcgaccg gttaaacccg    60
ggtcgatgca gtaagctagc t                                             81

<210> SEQ ID NO 53
<211> LENGTH: 82
<212> TYPE: DNA
<213> ORGANISM: Artificial Sequence
<220> FEATURE:
<223> OTHER INFORMATION: chemically synthesized sequence

<400> SEQUENCE: 53
taatacgact cactataggg gtgcgcggtt acaaggcaac atacgtaacc ggttaaaccc    60
gggtcgatgc agtaagctag ct                                            82

<210> SEQ ID NO 54
<211> LENGTH: 83
<212> TYPE: DNA
<213> ORGANISM: Artificial Sequence
<220> FEATURE:
<223> OTHER INFORMATION: chemically synthesized sequence
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 54
taatacnact cactataggg gggacggggt gacaaagtgt cnaacgtaac cggttaaacc    60
cgggtcgatg cagtaagcta gct                                           83

<210> SEQ ID NO 55
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 55
taatacgact cactataggg gagacggcgg tacaagtcca tatgtaaccg gttaaacccg    60
ggtcgatgca gtaagctagc t                                             81

<210> SEQ ID NO 56
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 56
taatacgact cactataggg gagtgggggc ttctcgttgc cacgtaaccg cttaaacccg    60
ggtcgatgca gtaagctagc t                                             81

<210> SEQ ID NO 57
<211> LENGTH: 83
<212> TYPE: DNA
```

<213> ORGANISM: Artificial Sequence
<220> FEATURE:
<223> OTHER INFORMATION: chemically synthesized sequence

<400> SEQUENCE: 57
taatacgact cactataggg gggctgagcg tgtttgaggg accacgttac cggttaaacc    60
cgggtcgatg cagtaagcta gct                                            83

<210> SEQ ID NO 58
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 58
taatacgact cactataggg gggtgggcgc aatgaaaagt tgggcgtaac cggttcaacc    60
cgggtcgatg cagtaagcta gct                                            83

<210> SEQ ID NO 59
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 59
taatacgact cactataggg ggtagtgaag taaggcagtg ttacgtaacc ggtgaacccg    60
ggtcgatgca gtaagctagc t                                              81

<210> SEQ ID NO 60
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 60
taatacgact cactataggg gggagggtgg gctagaacac acaacgtaac cggttaaacc    60
cgggtcgatg cagtaagcta gct                                            83

<210> SEQ ID NO 61
<211> LENGTH: 84
<212> TYPE: DNA
<213> ORGANISM: Artificial Sequence
<220> FEATURE:
<223> OTHER INFORMATION: chemically synthesized sequence

<400> SEQUENCE: 61
taatacgact cactataggg ggggagagag gcggttacgt agggacgtta ccgattgaac    60
tcaggtcgat gcagtaagct agct                                           84

<210> SEQ ID NO 62
<211> LENGTH: 87
<212> TYPE: DNA
<213> ORGANISM: Artificial Sequence
<220> FEATURE:
<223> OTHER INFORMATION: chemically synthesized sequence

<400> SEQUENCE: 62
taatacgact cactataggg gggggggcg aataggtagg gcgacgaacg ttaccggtta    60
aacccgggtc gatgcagtaa gctagct                                        87

<210> SEQ ID NO 63
<211> LENGTH: 82
<212> TYPE: DNA
<213> ORGANISM: Artificial Sequence
<220> FEATURE:
<223> OTHER INFORMATION: chemically synthesized sequence

<400> SEQUENCE: 63
taatacgact cactataggg ggagaggagg tccggctaga caacgtaacc ggttaaaccc    60
gggtcgatgc agtaagctag ct                                            82

<210> SEQ ID NO 64
<211> LENGTH: 69
<212> TYPE: DNA
<213> ORGANISM: Artificial Sequence
<220> FEATURE:
<223> OTHER INFORMATION: chemically synthesized sequence

<400> SEQUENCE: 64
taatacgact cactataggg gggaggacgg gtcgtactgt taaacctggg tcgatgcagt    60
aagctagct                                                           69

<210> SEQ ID NO 65
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 65
taatacgact cactataggg ggcgcaacaa cgggaagtat acgtaaccgg tttaacccg     60 ggtcgatgca gtaagctagc t                                             81

<210> SEQ ID NO 66
<211> LENGTH: 82
<212> TYPE: DNA
<213> ORGANISM: Artificial Sequence
<220> FEATURE:
<223> OTHER INFORMATION: chemically synthesized sequence

<400> SEQUENCE: 66
taatacgact cactataggg ggaaggaaca cgcacatgca taacgtaact ggttgacccc    60
gggtcgatgc agtaagctag ct                                            82

<210> SEQ ID NO 67
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 67
taatacgact cactataggg gagtggggag tactgtggac aacgtgaccg gttaacccg     60 ggtcgatgca gtaagctagc t                                             81

<210> SEQ ID NO 68
<211> LENGTH: 40
<212> TYPE: DNA
<213> ORGANISM: Artificial Sequence
<220> FEATURE:
<223> OTHER INFORMATION: chemically synthesized sequence

<400> SEQUENCE: 68

```
taatacgact cactataggg gtcgatgcag taagctagct                    40
```

<210> SEQ ID NO 69
<211> LENGTH: 85
<212> TYPE: DNA
<213> ORGANISM: Artificial Sequence
<220> FEATURE:
<223> OTHER INFORMATION: chemically synthesized sequence

<400> SEQUENCE: 69

```
taatacgact cactataggg gggggggcta gggcggtcgg atcggacgta accagttaaa    60
cccgggtcga tgcagtaagc tagct                                         85
```

<210> SEQ ID NO 70
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 70

```
taatacgact cactataggg ggggtggggg ttgctacatg ccctcgtaac cggttaagcc    60
caggtcgatg cagtaagcta gct                                           83
```

<210> SEQ ID NO 71
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 71

```
taatacgact cactataggg gggtggcgac gatggagaga ataacgtaat cggttaaacc    60
cgggtcgatg cagtaagcta gct                                           83
```

<210> SEQ ID NO 72
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 72

```
taatacgact cactataggg ggtaggcggg cctcatcaac aacgcaaccg gttaaacccg    60
ggtcgatgca gtaagctagc t                                             81
```

<210> SEQ ID NO 73
<211> LENGTH: 82
<212> TYPE: DNA
<213> ORGANISM: Artificial Sequence
<220> FEATURE:
<223> OTHER INFORMATION: chemically synthesized sequence

<400> SEQUENCE: 73

```
taatacgact cactataggg ggtggctggt aaggacacaa acacgtaact cgttaaaccc    60
gggtcgatgc agtaagctag ct                                            82
```

<210> SEQ ID NO 74
<211> LENGTH: 83
<212> TYPE: DNA
<213> ORGANISM: Artificial Sequence
<220> FEATURE:
<223> OTHER INFORMATION: chemically synthesized sequence

```
<400> SEQUENCE: 74
taatacgact cactataggg gggcgggcag cgcttataga tccacgtaac cggttaaacc    60
cgggtcgatg cagtaagcta gct                                           83

<210> SEQ ID NO 75
<211> LENGTH: 86
<212> TYPE: DNA
<213> ORGANISM: Artificial Sequence
<220> FEATURE:
<223> OTHER INFORMATION: chemically synthesized sequence

<400> SEQUENCE: 75
taatacgact cactataggg gggggtatc tgcggttagg ctatcgacgt acccagttaa    60
acccgggtcg atgcagtaag ctagct                                        86

<210> SEQ ID NO 76
<211> LENGTH: 82
<212> TYPE: DNA
<213> ORGANISM: Artificial Sequence
<220> FEATURE:
<223> OTHER INFORMATION: chemically synthesized sequence

<400> SEQUENCE: 76
taatacgact cactataggg ggggtagggg acatcatagg tatacgtaac cggttaaccc    60
gggtcgatgc agtaagctag ct                                            82

<210> SEQ ID NO 77
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 77
taatacgact cactataggg gcgcgtgcgt gtatccatta aacgtgactg gttaaacccg    60
ggtcgatgca gtaagctagc t                                             81

<210> SEQ ID NO 78
<211> LENGTH: 84
<212> TYPE: DNA
<213> ORGANISM: Artificial Sequence
<220> FEATURE:
<223> OTHER INFORMATION: chemically synthesized sequence

<400> SEQUENCE: 78
taatacgact cactataggg gggggagcgt ggatcttgag tgtatacgta accggttaaa    60
cccggtcgat gcagtaagct agct                                          84

<210> SEQ ID NO 79
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 79
taatacgact cactataggg gatggagagg agtgtacgca tatacaaccg gttaaacccg    60
ggtcgatgca gtaagctagc t                                             81

<210> SEQ ID NO 80
<211> LENGTH: 80
<212> TYPE: DNA
```

```
<213> ORGANISM: Artificial Sequence
<220> FEATURE:
<223> OTHER INFORMATION: chemically synthesized sequence

<400> SEQUENCE: 80
taatacgact cactataggg gcgggtggtc gcgatggtta acgtaactgg ttaaacccgg    60
gtcgatgcag taagctagct                                               80

<210> SEQ ID NO 81
<211> LENGTH: 90
<212> TYPE: DNA
<213> ORGANISM: Artificial Sequence
<220> FEATURE:
<223> OTHER INFORMATION: chemically synthesized sequence

<400> SEQUENCE: 81
taatacgact cactataggg ggggggggg acgttagctt ctctgtattt acgtaaccgg    60
ttaagcccgg gtcgatgcag taagctagct                                   90

<210> SEQ ID NO 82
<211> LENGTH: 40
<212> TYPE: DNA
<213> ORGANISM: Artificial Sequence
<220> FEATURE:
<223> OTHER INFORMATION: chemically synthesized sequence

<400> SEQUENCE: 82
taatacgact cactataggg gtcgatgcag taagctagct                        40

<210> SEQ ID NO 83
<211> LENGTH: 83
<212> TYPE: DNA
<213> ORGANISM: Artificial Sequence
<220> FEATURE:
<223> OTHER INFORMATION: chemically synthesized sequence
<220> FEATURE:
<221> NAME/KEY: misc_feature
<222> LOCATION: (43)..(43)
<223> OTHER INFORMATION: n is a, c, g, or t

<400> SEQUENCE: 83
taatacgact cactataggg gggatggagt gggtgcaaat aanacgtaac tggttaaacc   60
cgggtcgatg cagtaagcta gct                                           83

<210> SEQ ID NO 84
<211> LENGTH: 81
<212> TYPE: DNA
<213> ORGANISM: Artificial Sequence
<220> FEATURE:
<223> OTHER INFORMATION: chemically synthesized sequence
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (50)..(50)
```

```
<223> OTHER INFORMATION: n is a, c, g, or t
<220> FEATURE:
<221> NAME/KEY: misc_feature
<222> LOCATION: (69)..(71)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t

<400> SEQUENCE: 84
taatacgact cactataggg gagngtgagg ggtgaatant aangtaancn gttaaacctg    60
ggtcgatgnn ntannctngn t                                             81

<210> SEQ ID NO 85
<211> LENGTH: 40
<212> TYPE: DNA
<213> ORGANISM: Artificial Sequence
<220> FEATURE:
<223> OTHER INFORMATION: chemically synthesized sequence
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 85
naatnngact cacaanaggg gtcgatgcag taagctagct                         40

<210> SEQ ID NO 86
<211> LENGTH: 84
<212> TYPE: DNA
<213> ORGANISM: Artificial Sequence
<220> FEATURE:
<223> OTHER INFORMATION: chemically synthesized sequence

<400> SEQUENCE: 86
taatacgact cactataggg gggggtgacg tacggatcta agtaacgtaa ccggttaaac   60
ccgggtcgat gcagtaagct agct                                         84

<210> SEQ ID NO 87
<211> LENGTH: 80
<212> TYPE: DNA
<213> ORGANISM: Artificial Sequence
<220> FEATURE:
<223> OTHER INFORMATION: chemically synthesized sequence

<400> SEQUENCE: 87
taatacgact cactataggg gagggacaga cactttgtag acgtaaccag ttaaacccgg   60
gtcgatgcag taagctagct                                              80

<210> SEQ ID NO 88
<211> LENGTH: 83
<212> TYPE: DNA
```

<213> ORGANISM: Artificial Sequence
<220> FEATURE:
<223> OTHER INFORMATION: chemically synthesized sequence

<400> SEQUENCE: 88
taatacgact cactataggg gggggacttg gcactacgta acaacgtaac cgcttaaacc    60
cgggtcgatg cagtaagcta gct                                           83

<210> SEQ ID NO 89
<211> LENGTH: 86
<212> TYPE: DNA
<213> ORGANISM: Artificial Sequence
<220> FEATURE:
<223> OTHER INFORMATION: chemically synthesized sequence

<400> SEQUENCE: 89
taatacgact cactataggg gggggggcct ctcgaccaaa agcccaacgt aaccggttaa    60
acccgggtcg atgcagtaag ctagct                                        86

<210> SEQ ID NO 90
<211> LENGTH: 85
<212> TYPE: DNA
<213> ORGANISM: Artificial Sequence
<220> FEATURE:
<223> OTHER INFORMATION: chemically synthesized sequence
<220> FEATURE:
<221> NAME/KEY: misc_feature
<222> LOCATION: (7)..(7)
<223> OTHER INFORMATION: n is a, c, g, or t

<400> SEQUENCE: 90
taatacnact cactataggg gggggggat agtcatgact gataaaacgt aactgttgag     60
cccgggtcga tgcagtaagc tagct                                         85

<210> SEQ ID NO 91
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 91
taatacgact cactataggg gacagtgcta gtggaatagc aacgtaacca gttaaacccg    60
ggtcgatgca gtaagctagc t                                             81

<210> SEQ ID NO 92
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 92
taatacgact cactataggg gacgaccact atactccgag aacgtaaccg gttaaacccg    60
ggtcgatgca gtaagctagc t                                             81

<210> SEQ ID NO 93
<211> LENGTH: 82
<212> TYPE: DNA
<213> ORGANISM: Artificial Sequence
<220> FEATURE:
<223> OTHER INFORMATION: chemically synthesized sequence

<400> SEQUENCE: 93

```
taatacgact cactataggg ggatggaggc gtagtgtagt caacgttacc ggttaaaccc    60
gggtcgatgc agtaagctag ct                                            82
```

<210> SEQ ID NO 94
<211> LENGTH: 82
<212> TYPE: DNA
<213> ORGANISM: Artificial Sequence
<220> FEATURE:
<223> OTHER INFORMATION: chemically synthesized sequence

<400> SEQUENCE: 94

```
taatacgact cactataggg gggaggtata gatggaatgg ttatgtaacc tgttaaaccc    60
gggtcgatgc agtaagctag ct                                            82
```

<210> SEQ ID NO 95
<211> LENGTH: 81
<212> TYPE: DNA
<213> ORGANISM: Artificial Sequence
<220> FEATURE:
<223> OTHER INFORMATION: chemically synthesized sequence

<400> SEQUENCE: 95

```
taatacgact cactataggg gtggggagga ccacttagat aacgtcaccg gttaaacccg    60
ggtcgatgca gtaagctagc t                                             81
```

<210> SEQ ID NO 96
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 96

```
taatacgact cactataggg gggatagggg cgagagagtc acaacgtaac cggttaatcc    60
cgggtcgatg cagtaagcta gct                                           83
```

<210> SEQ ID NO 97
<211> LENGTH: 83
<212> TYPE: DNA
<213> ORGANISM: Artificial Sequence
<220> FEATURE:
<223> OTHER INFORMATION: chemically synthesized sequence

<400> SEQUENCE: 97

```
taatacgact cactataggg gggggatggc cgaatcataa aataacgtaa ccgttagacc    60
cgggtcgatg cagtaagcta gct                                           83
```

<210> SEQ ID NO 98
<211> LENGTH: 78
<212> TYPE: DNA
<213> ORGANISM: Artificial Sequence
<220> FEATURE:
<223> OTHER INFORMATION: chemically synthesized sequence

<400> SEQUENCE: 98

```
taatacgact cactataggg ggcgattgct gagtcagttc gtaatcggtt aaacccgggt    60
cgatgcagta agctagct                                                 78
```

<210> SEQ ID NO 99
<211> LENGTH: 85
<212> TYPE: DNA
<213> ORGANISM: Artificial Sequence
<220> FEATURE:

-continued

<223> OTHER INFORMATION: chemically synthesized sequence

<400> SEQUENCE: 99

```
taatacgact cactataggg gggggaggat ccgaaacaca gggatccgta accggttaaa    60
gccgggtcga tgcagtaagc tagct                                         85
```

<210> SEQ ID NO 100
<211> LENGTH: 883
<212> TYPE: PRT
<213> ORGANISM: Artificial Sequence
<220> FEATURE:
<223> OTHER INFORMATION: chemically synthesized modified T7 polymerase Y639L

<400> SEQUENCE: 100

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
```

-continued

```
                325                 330                 335
Val Ala Asn Val Ile Thr Lys Trp Lys His Cys Pro Val Glu Asp Ile
                340                 345                 350
Pro Ala Ile Glu Arg Glu Leu Pro Met Lys Pro Glu Asp Ile Asp
                355                 360                 365
Met Asn Pro Glu Ala Leu Thr Ala Trp Lys Arg Ala Ala Ala Val
            370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
                420                 425                 430
Asn Pro Gln Gly Asn Asp Met Thr Lys Gly Leu Leu Thr Leu Ala Lys
                435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
                500                 505                 510
Ala Phe Cys Phe Glu Tyr Ala Gly Val Gln His His Gly Leu Ser Tyr
                515                 520                 525
Asn Cys Ser Leu Pro Leu Ala Phe Asp Gly Ser Cys Ser Gly Ile Gln
            530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
                580                 585                 590
Glu Val Val Thr Val Thr Asp Glu Asn Thr Gly Glu Ile Ser Glu Lys
                595                 600                 605
Val Lys Leu Gly Thr Lys Ala Leu Ala Gly Gln Trp Leu Ala Tyr Gly
            610                 615                 620
Val Thr Arg Ser Val Thr Lys Arg Ser Val Met Thr Leu Ala Leu Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
                660                 665                 670
Ala Ala Gly Tyr Met Ala Lys Leu Ile Trp Glu Ser Val Ser Val Thr
            675                 680                 685
Val Val Ala Ala Val Glu Ala Met Asn Trp Leu Lys Ser Ala Ala Lys
                690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
                740                 745                 750
```

```
Gly Gln Phe Arg Leu Gln Pro Thr Ile Asn Thr Asn Lys Asp Ser Glu
            755                 760                 765
Ile Asp Ala His Lys Gln Glu Ser Gly Ile Ala Pro Asn Phe Val His
        770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
850                 855                 860
Pro Ala Lys Gly Asn Leu Asn Leu Arg Asp Ile Leu Glu Ser Asp Phe
865                 870                 875                 880
Ala Phe Ala

<210> SEQ ID NO 101
<211> LENGTH: 883
<212> TYPE: PRT
<213> ORGANISM: Artificial Sequence
<220> FEATURE:
<223> OTHER INFORMATION: chemically synthesized modified T7 polymerase
      Y639L/K378R

<400> SEQUENCE: 101

Met Asn Thr Ile Asn Ile Ala Lys Asn Asp Phe Ser Asp Ile Glu Leu
1               5                   10                  15
Ala Ala Ile Pro Phe Asn Thr Leu Ala Asp His Tyr Gly Glu Arg Leu
            20                  25                  30
Ala Arg Glu Gln Leu Ala Leu Glu His Glu Ser Tyr Glu Met Gly Glu
        35                  40                  45
Ala Arg Phe Arg Lys Met Phe Glu Arg Gln Leu Lys Ala Gly Glu Val
    50                  55                  60
Ala Asp Asn Ala Ala Ala Lys Pro Leu Ile Thr Thr Leu Leu Pro Lys
65                  70                  75                  80
Met Ile Ala Arg Ile Asn Asp Trp Phe Glu Glu Val Lys Ala Lys Arg
                85                  90                  95
Gly Lys Arg Pro Thr Ala Phe Gln Phe Leu Gln Glu Ile Lys Pro Glu
            100                 105                 110
Ala Val Ala Tyr Ile Thr Ile Lys Thr Thr Leu Ala Cys Leu Thr Ser
        115                 120                 125
Ala Asp Asn Thr Thr Val Gln Ala Val Ala Ser Ala Ile Gly Arg Ala
    130                 135                 140
Ile Glu Asp Glu Ala Arg Phe Gly Arg Ile Arg Asp Leu Glu Ala Lys
145                 150                 155                 160
His Phe Lys Lys Asn Val Glu Glu Gln Leu Asn Lys Arg Val Gly His
                165                 170                 175
Val Tyr Lys Lys Ala Phe Met Gln Val Val Glu Ala Asp Met Leu Ser
            180                 185                 190
Lys Gly Leu Leu Gly Gly Glu Ala Trp Ser Ser Trp His Lys Glu Asp
        195                 200                 205
Ser Ile His Val Gly Val Arg Cys Ile Glu Met Leu Ile Glu Ser Thr
    210                 215                 220
Gly Met Val Ser Leu His Arg Gln Asn Ala Gly Val Val Gly Gln Asp
```

```
            225                 230                 235                 240
Ser Glu Thr Ile Glu Leu Ala Pro Glu Tyr Ala Glu Ala Ile Ala Thr
                245                 250                 255
Arg Ala Gly Ala Leu Ala Gly Ile Ser Pro Met Phe Gln Pro Cys Val
                260                 265                 270
Val Pro Pro Lys Pro Trp Thr Gly Ile Thr Gly Gly Tyr Trp Ala
            275                 280                 285
Asn Gly Arg Arg Pro Leu Ala Leu Val Arg Thr His Ser Lys Lys Ala
            290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Glu Asp Ile
                340                 345                 350
Pro Ala Ile Glu Arg Glu Leu Pro Met Lys Pro Glu Asp Ile Asp
            355                 360                 365
Met Asn Pro Glu Ala Leu Thr Ala Trp Arg Arg Ala Ala Ala Val
370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
                420                 425                 430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
                500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
            530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
                580                 585                 590
Glu Val Val Thr Val Thr Asp Glu Asn Thr Gly Glu Ile Ser Glu Lys
                595                 600                 605
Val Lys Leu Gly Thr Lys Ala Leu Ala Gly Gln Trp Leu Ala Tyr Gly
            610                 615                 620
Val Thr Arg Ser Val Thr Lys Arg Ser Val Met Thr Leu Ala Leu Gly
625                 630                 635                 640
Ser Lys Glu Phe Gly Phe Arg Gln Gln Val Leu Glu Asp Thr Ile Gln
                645                 650                 655
```

-continued

```
Pro Ala Ile Asp Ser Gly Lys Gly Leu Met Phe Thr Gln Pro Asn Gln
        660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 102
<211> LENGTH: 883
<212> TYPE: PRT
<213> ORGANISM: Artificial Sequence
<220> FEATURE:
<223> OTHER INFORMATION: chemically synthesized modified T7 polymerase
      P266L/Y639L/H784A

<400> SEQUENCE: 102

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
```

```
                130                 135                 140
Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
                195                 200                 205

Ser Ile His Val Gly Val Arg Cys Ile Glu Met Leu Ile Glu Ser Thr
210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Leu Met Phe Gln Pro Cys Val
                260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
                290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Leu Pro Met Lys Pro Glu Asp Ile Asp
                355                 360                 365

Met Asn Pro Glu Ala Leu Thr Ala Trp Lys Arg Ala Ala Ala Val
                370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
                450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
                515                 520                 525

Asn Cys Ser Leu Pro Leu Ala Phe Asp Gly Ser Cys Ser Gly Ile Gln
                530                 535                 540

His Phe Ser Ala Met Leu Arg Asp Glu Val Gly Gly Arg Ala Val Asn
545                 550                 555                 560
```

```
Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
        610                 615                 620

Val Thr Arg Ser Val Thr Lys Arg Ser Val Met Thr Leu Ala Leu Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
        690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val Ala
        770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
        850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 103
<211> LENGTH: 883
<212> TYPE: PRT
<213> ORGANISM: Artificial Sequence
<220> FEATURE:
<223> OTHER INFORMATION: chemically synthesized modified T7 polymerase
      P266L/Y639L/H784A/K378R

<400> SEQUENCE: 103

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
```

```
              35                  40                  45
Ala Arg Phe Arg Lys Met Phe Glu Arg Gln Leu Lys Ala Gly Glu Val
 50                  55                  60

Ala Asp Asn Ala Ala Lys Pro Leu Ile Thr Thr Leu Leu Pro Lys
 65                  70                  75                  80

Met Ile Ala Arg Ile Asn Asp Trp Phe Glu Val Lys Ala Lys Arg
                 85                  90                  95

Gly Lys Arg Pro Thr Ala Phe Gln Phe Leu Gln Glu Ile Lys Pro Glu
             100                 105                 110

Ala Val Ala Tyr Ile Thr Ile Lys Thr Thr Leu Ala Cys Leu Thr Ser
             115                 120                 125

Ala Asp Asn Thr Thr Val Gln Ala Val Ala Ser Ala Ile Gly Arg Ala
             130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                 165                 170                 175

Val Tyr Lys Lys Ala Phe Met Gln Val Val Glu Ala Asp Met Leu Ser
             180                 185                 190

Lys Gly Leu Leu Gly Gly Glu Ala Trp Ser Ser Trp His Lys Glu Asp
             195                 200                 205

Ser Ile His Val Gly Val Arg Cys Ile Glu Met Leu Ile Glu Ser Thr
             210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                 245                 250                 255

Arg Ala Gly Ala Leu Ala Gly Ile Ser Leu Met Phe Gln Pro Cys Val
             260                 265                 270

Val Pro Pro Lys Pro Trp Thr Gly Ile Thr Gly Gly Tyr Trp Ala
             275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                 325                 330                 335

Val Ala Asn Val Ile Thr Lys Trp Lys His Cys Pro Val Glu Asp Ile
             340                 345                 350

Pro Ala Ile Glu Arg Glu Glu Leu Pro Met Lys Pro Glu Asp Ile Asp
             355                 360                 365

Met Asn Pro Glu Ala Leu Thr Ala Trp Arg Arg Ala Ala Ala Val
             370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                 405                 410                 415

Pro Tyr Asn Met Asp Trp Arg Gly Arg Val Tyr Ala Val Ser Met Phe
             420                 425                 430

Asn Pro Gln Gly Asn Asp Met Thr Lys Gly Leu Leu Thr Leu Ala Lys
             435                 440                 445

Gly Lys Pro Ile Gly Lys Glu Gly Tyr Tyr Trp Leu Lys Ile His Gly
             450                 455                 460
```

```
Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
        500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Leu Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val Ala
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
        850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 104
<211> LENGTH: 20
<212> TYPE: DNA
<213> ORGANISM: Artificial Sequence
<220> FEATURE:
<223> OTHER INFORMATION: chemically synthesized 5'-primer

<400> SEQUENCE: 104
agctagctta ctgcatcgac                                               20

<210> SEQ ID NO 105
<211> LENGTH: 18
<212> TYPE: DNA
<213> ORGANISM: Artificial Sequence
<220> FEATURE:
<223> OTHER INFORMATION: chemically synthesized 3'-primer

<400> SEQUENCE: 105
taatacgact cactatag                                                 18

<210> SEQ ID NO 106
<211> LENGTH: 94
<212> TYPE: DNA
<213> ORGANISM: Artificial Sequence
<220> FEATURE:
<223> OTHER INFORMATION: chemically synthesized control DNA
      transcription template without leader sequence ARC2117
<220> FEATURE:
<221> NAME/KEY: misc_feature
<222> LOCATION: (41)..(70)
<223> OTHER INFORMATION: n is a, t, c or g

<400> SEQUENCE: 106
taatacgact cactataggg gagaggagag aacgttctcg nnnnnnnnnn nnnnnnnnnn    60
nnnnnnnnnn ggatcgttac gactagcatc gatg                               94

<210> SEQ ID NO 107
<211> LENGTH: 35
<212> TYPE: DNA
<213> ORGANISM: Artificial Sequence
<220> FEATURE:
<223> OTHER INFORMATION: chemically synthesized sequence

<400> SEQUENCE: 107
agtcatgacg ctggctctgg ggtccaaaga gttcg                              35

<210> SEQ ID NO 108
<211> LENGTH: 34
<212> TYPE: DNA
<213> ORGANISM: Artificial Sequence
<220> FEATURE:
<223> OTHER INFORMATION: chemically synthesized sequence

<400> SEQUENCE: 108
gaactctttg accccagag ccagcgtcat gact                                34

<210> SEQ ID NO 109
<211> LENGTH: 31
<212> TYPE: DNA
<213> ORGANISM: Artificial Sequence
<220> FEATURE:
<223> OTHER INFORMATION: chemically synthesized sequence

<400> SEQUENCE: 109
ggctggcatc tctctgatgt tccaaccttg c                                  31

```
<210> SEQ ID NO 110
<211> LENGTH: 31
<212> TYPE: DNA
<213> ORGANISM: Artificial Sequence
<220> FEATURE:
<223> OTHER INFORMATION: chemically synthesized sequence

<400> SEQUENCE: 110
gcaaggttgg aacatcagag agatgccagc c                              31

<210> SEQ ID NO 111
<211> LENGTH: 34
<212> TYPE: DNA
<213> ORGANISM: Artificial Sequence
<220> FEATURE:
<223> OTHER INFORMATION: chemically synthesized sequence

<400> SEQUENCE: 111
cgctcctaac tttgtagcca gccaagacgg tagc                           34

<210> SEQ ID NO 112
<211> LENGTH: 34
<212> TYPE: DNA
<213> ORGANISM: Artificial Sequence
<220> FEATURE:
<223> OTHER INFORMATION: chemically synthesized sequence

<400> SEQUENCE: 112
gctaccgtct tggctggcta caaagttagg agcg                           34

<210> SEQ ID NO 113
<211> LENGTH: 33
<212> TYPE: DNA
<213> ORGANISM: Artificial Sequence
<220> FEATURE:
<223> OTHER INFORMATION: chemically synthesized sequence

<400> SEQUENCE: 113
gctctcaccg cgtggagacg tgctgccgct gct                            33

<210> SEQ ID NO 114
<211> LENGTH: 33
<212> TYPE: DNA
<213> ORGANISM: Artificial Sequence
<220> FEATURE:
<223> OTHER INFORMATION: chemically synthesized sequence

<400> SEQUENCE: 114
agcagcggca gcacgtctcc acgcggtgag agc                            33

<210> SEQ ID NO 115
<211> LENGTH: 66
<212> TYPE: DNA
<213> ORGANISM: Artificial Sequence
<220> FEATURE:
<223> OTHER INFORMATION: chemically synthesized 5'-primer

<400> SEQUENCE: 115
aaaaaaaaaa aaaaaaaaa aaaaaaataa tacgactcac tatagggag tacaataacg  60 ttctcg                                                          66

<210> SEQ ID NO 116
<211> LENGTH: 20
<212> TYPE: DNA
<213> ORGANISM: Artificial Sequence
<220> FEATURE:
<223> OTHER INFORMATION: chemically synthesized 3'-primer
```

```
<400> SEQUENCE: 116
catcgatgct agtcgtaacg                                            20

<210> SEQ ID NO 117
<211> LENGTH: 24
<212> TYPE: DNA
<213> ORGANISM: Artificial Sequence
<220> FEATURE:
<223> OTHER INFORMATION: chemically synthesized DNA transcription
      template
<220> FEATURE:
<221> NAME/KEY: misc_feature
<222> LOCATION: (5)..(20)
<223> OTHER INFORMATION: n is a, t, c or g
<220> FEATURE:
<221> NAME/KEY: misc_feature
<222> LOCATION: (21)..(24)
<223> OTHER INFORMATION: n is a, c, g, or t

<400> SEQUENCE: 117
ggggnnnnnn nnnnnnnnnn nnnn                                       24

<210> SEQ ID NO 118
<211> LENGTH: 59
<212> TYPE: DNA
<213> ORGANISM: Artificial Sequence
<220> FEATURE:
<223> OTHER INFORMATION: chemically synthesized primer

<400> SEQUENCE: 118
gatcgatcga tcgatcgatc taatacgact cactataggg gagtacaata acgttctcg  59

<210> SEQ ID NO 119
<211> LENGTH: 24
<212> TYPE: DNA
<213> ORGANISM: Artificial Sequence
<220> FEATURE:
<223> OTHER INFORMATION: chemically synthesized primer

<400> SEQUENCE: 119
catcgatgct agtcgtaacg atcc                                       24

<210> SEQ ID NO 120
<211> LENGTH: 2652
<212> TYPE: DNA
<213> ORGANISM: Artificial Sequence
<220> FEATURE:
<223> OTHER INFORMATION: chemically synthesized wild-type T7 RNA
      polymerase sequence

<400> SEQUENCE: 120
atgaacacga ttaacatcgc taagaacgac ttctctgaca tcgaactggc tgctatcccg    60
ttcaacactc tggctgacca ttacggtgag cgtttagctc gcgaacagtt ggcccttgag   120
catgagtctt acgagatggg tgaagcacgc ttccgcaaga tgtttgagcg tcaacttaaa   180
gctggtgagg ttgcggataa cgctgccgcc aagcctctca tcactaccct actccctaag   240
atgattgcac gcatcaacga ctggtttgag gaagtgaaag ctaagcgcgg caagcgcccg   300
acagccttcc agttcctgca agaaatcaag ccggaagccg tagcgtacat caccattaag   360
accactctgg cttgcctaac cagtgctgac aatacaaccg ttcaggctgt agcaagcgca   420
atcggtcggg ccattgagga cgaggctcgc ttcggtcgta tccgtgacct tgaagctaag   480
cacttcaaga aaaacgttga ggaacaactc aacaagcgcg tagggcacgt ctacaagaaa   540
gcatttatgc aagttgtcga ggctgacatg ctctctaagg gtctactcgg tggcgaggcg   600
```

```
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg gctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag acatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga aaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta gctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct   2340
aactttgtac acagccaaga cggtagccac cttcgtaaga ctgtagtgtg gcacacgag   2400 aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aa                                                        2652
```

<210> SEQ ID NO 121
<211> LENGTH: 883
<212> TYPE: PRT
<213> ORGANISM: Artificial Sequence
<220> FEATURE:
<223> OTHER INFORMATION: chemically synthesized wild-type T7 RNA
      polymerase sequence

<400> SEQUENCE: 121

```
Met Asn Thr Ile Asn Ile Ala Lys Asn Asp Phe Ser Asp Ile Glu Leu
 1               5                  10                  15
Ala Ala Ile Pro Phe Asn Thr Leu Ala Asp His Tyr Gly Glu Arg Leu
             20                  25                  30
Ala Arg Glu Gln Leu Ala Leu Glu His Glu Ser Tyr Glu Met Gly Glu
         35                  40                  45
Ala Arg Phe Arg Lys Met Phe Glu Arg Gln Leu Lys Ala Gly Glu Val
     50                  55                  60
Ala Asp Asn Ala Ala Lys Pro Leu Ile Thr Thr Leu Leu Pro Lys
 65                  70                  75                  80
Met Ile Ala Arg Ile Asn Asp Trp Phe Glu Glu Val Lys Ala Lys Arg
                 85                  90                  95
Gly Lys Arg Pro Thr Ala Phe Gln Phe Leu Gln Glu Ile Lys Pro Glu
            100                 105                 110
Ala Val Ala Tyr Ile Thr Ile Lys Thr Thr Leu Ala Cys Leu Thr Ser
        115                 120                 125
Ala Asp Asn Thr Thr Val Gln Ala Val Ala Ser Ala Ile Gly Arg Ala
    130                 135                 140
Ile Glu Asp Glu Ala Arg Phe Gly Arg Ile Arg Asp Leu Glu Ala Lys
145                 150                 155                 160
His Phe Lys Lys Asn Val Glu Glu Gln Leu Asn Lys Arg Val Gly His
                165                 170                 175
Val Tyr Lys Lys Ala Phe Met Gln Val Val Glu Ala Asp Met Leu Ser
            180                 185                 190
Lys Gly Leu Leu Gly Gly Glu Ala Trp Ser Ser Trp His Lys Glu Asp
        195                 200                 205
Ser Ile His Val Gly Val Arg Cys Ile Glu Met Leu Ile Glu Ser Thr
    210                 215                 220
Gly Met Val Ser Leu His Arg Gln Asn Ala Gly Val Val Gly Gln Asp
225                 230                 235                 240
Ser Glu Thr Ile Glu Leu Ala Pro Glu Tyr Ala Glu Ala Ile Ala Thr
                245                 250                 255
Arg Ala Gly Ala Leu Ala Gly Ile Ser Pro Met Phe Gln Pro Cys Val
            260                 265                 270
Val Pro Pro Lys Pro Trp Thr Gly Ile Thr Gly Gly Tyr Trp Ala
        275                 280                 285
Asn Gly Arg Arg Pro Leu Ala Leu Val Arg Thr His Ser Lys Lys Ala
    290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Glu Asp Ile
            340                 345                 350
Pro Ala Ile Glu Arg Glu Glu Leu Pro Met Lys Pro Glu Asp Ile Asp
        355                 360                 365
Met Asn Pro Glu Ala Leu Thr Ala Trp Lys Arg Ala Ala Ala Val
    370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                405                 410                 415
```

```
Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845
```

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 122
<211> LENGTH: 2652
<212> TYPE: DNA
<213> ORGANISM: Artificial Sequence
<220> FEATURE:
<223> OTHER INFORMATION: chemically synthesized mutant T7 RNA polymerase
      Y639L/H784A sequence

<400> SEQUENCE: 122

| | |
|---|---|
| atgaacacga ttaacatcgc taagaacgac ttctctgaca tcgaactggc tgctatcccg | 60 |
| ttcaacactc tggctgacca ttacggtgag cgtttagctc gcgaacagtt ggcccttgag | 120 |
| catgagtctt acgagatggg tgaagcacgc ttccgcaaga tgtttgagcg tcaacttaaa | 180 |
| gctggtgagg ttgcggataa cgctgccgcc aagcctctca tcactaccct actccctaag | 240 |
| atgattgcac gcatcaacga ctggtttgag gaagtgaaag ctaagcgcgg caagcgcccg | 300 |
| acagccttcc agttcctgca agaaatcaag ccggaagccg tagcgtacat caccattaag | 360 |
| accactctgg cttgcctaac cagtgctgac aatacaaccg ttcaggctgt agcaagcgca | 420 |
| atcggtcggg ccattgagga cgaggctcgc ttcggtcgta ccgtgaccct gaagctaag | 480 |
| cacttcaaga aaacgttga ggaacaactc aacaagcgcg tagggcacgt ctacaagaaa | 540 |
| gcatttatgc aagttgtcga ggctgacatg ctctctaagg gtctactcgg tggcgaggcg | 600 |
| tggtcttcgt ggcataagga agactctatt catgtaggag tacgctgcat cgagatgctc | 660 |
| attgagtcaa ccggaatggt tagcttacac cgccaaaatg ctggcgtagt aggtcaagac | 720 |
| tctgagacta tcgaactcgc acctgaatac gctgaggcta tcgcaacccg tgcaggtgcg | 780 |
| ctggctggca tctctccgat gttccaacct tgcgtagttc ctcctaagcc gtggactggc | 840 |
| attactggtg gtggctattg ggctaacggt cgtcgtcctc tggcgctggt gcgtactcac | 900 |
| agtaagaaag cactgatgcg ctacgaagac gtttacatgc tgaggtgta caaagcgatt | 960 |
| aacattgcgc aaaacaccgc atggaaaatc aacaagaaag tcctagcggt cgccaacgta | 1020 |
| atcaccaagt ggaagcattg tccggtcgag gacatccctg cgattgagcg tgaagaactc | 1080 |
| ccgatgaaac cggaagacat cgacatgaat cctgaggctc tcaccgcgtg gaaacgtgct | 1140 |
| gccgctgctg tgtaccgcaa ggacaaggct cgcaagtctc gccgtatcag ccttgagttc | 1200 |
| atgcttgagc aagccaataa gtttgctaac cataaggcca tctggttccc ttacaacatg | 1260 |
| gactggcgcg gtcgtgttta cgctgtgtca atgttcaacc cgcaaggtaa cgatatgacc | 1320 |
| aaaggactgc ttacgctggc gaaggtaaa ccaatcggta aggaaggtta ctactggctg | 1380 |
| aaaatccacg gtgcaaactg tgcgggtgtc gataaggttc cgttccctga gcgcatcaag | 1440 |
| ttcattgagg aaaccacga gaacatcatg gcttgcgcta gtctccact ggagaacact | 1500 |
| tggtgggctg agcaagattc tccgttctgc ttccttgcgt tctgctttga gtacgctggg | 1560 |
| gtacagcacc acggcctgag ctataactgc tcccttccgc tggcgtttga cgggtcttgc | 1620 |
| tctggcatcc agcacttctc cgcgatgctc cgagatgagg taggtggtcg cgcggttaac | 1680 |
| ttgcttccta gtgaaaccgt tcaggacatc tacgggattg ttgctaagaa agtcaacgag | 1740 |
| attctacaag cagacgcaat caatgggacc gataacgaag tagttaccgt gaccgatgag | 1800 |

```
aacactggtg aaatctctga gaaagtcaag ctgggcacta aggcactggc tggtcaatgg      1860
ctggcttacg gtgttactcg cagtgtgact aagcgttcag tcatgacgct ggctctgggg      1920
tccaaagagt tcggcttccg tcaacaagtg ctggaagata ccattcagcc agctattgat      1980
tccggcaagg gtctgatgtt cactcagccg aatcaggctg ctggatacat ggctaagctg      2040
atttgggaat ctgtgagcgt gacggtggta gctgcggttg aagcaatgaa ctggcttaag      2100
tctgctgcta agctgctggc tgctgaggtc aaagataaga agactggaga gattcttcgc      2160
aagcgttgcg ctgtgcattg ggtaactcct gatggtttcc ctgtgtggca ggaatacaag      2220
aagcctattc agacgcgctt gaacctgatg ttcctcggtc agttccgctt acagcctacc      2280
attaacacca acaaagatag cgagattgat gcacacaaac aggagtctgg tatcgctcct      2340
aactttgtag ccagccaaga cggtagccac cttcgtaaga ctgtagtgtg ggcacacgag      2400
aagtacggaa tcgaatcttt tgcactgatt cacgactcct tcggtaccat tccggctgac      2460
gctgcgaacc tgttcaaagc agtgcgcgaa actatggttg acacatatga gtcttgtgat      2520
gtactggctg atttctacga ccagttcgct gaccagttgc acgagtctca attggacaaa      2580
atgccagcac ttccggctaa aggtaacttg aacctccgtg acatcttaga gtcggacttc      2640
gcgttcgcgt aa                                                           2652

<210> SEQ ID NO 123
<211> LENGTH: 2652
<212> TYPE: DNA
<213> ORGANISM: Artificial Sequence
<220> FEATURE:
<223> OTHER INFORMATION: chemically synthesized mutant T7 RNA polymerase
      Y639L/H784A/K378R sequence

<400> SEQUENCE: 123
atgaacacga ttaacatcgc taagaacgac ttctctgaca tcgaactggc tgctatcccg        60
ttcaacactc tggctgacca ttacggtgag cgtttagctc gcgaacagtt ggcccttgag       120
catgagtctt acgagatggg tgaagcacgc ttccgcaaga tgtttgagcg tcaacttaaa       180
gctggtgagg ttgcggataa cgctgccgcc aagcctctca tcactaccct actccctaag       240
atgattgcac gcatcaacga ctggtttgag gaagtgaaag ctaagcgcgg caagcgcccg       300
acagccttcc agttcctgca agaaatcaag ccggaagccg tagcgtacat caccattaag       360
accactctgg cttgcctaac cagtgctgac aatacaaccg ttcaggctgt agcaagcgca       420
atcggtcggg ccattgagga cgaggctcgc ttcggtcgta ccgtgaccct gaagctaag       480 cacttcaaga aaacgttga ggaacaactc aacaagcgcg tagggcacgt ctacaagaaa        540
gcatttatgc aagttgtcga ggctgacatg ctctctaagg gtctactcgg tggcgaggcg       600
tggtcttcgt ggcataagga agactctatt catgtaggag tacgctgcat cgagatgctc       660
attgagtcaa ccggaatggt tagcttacac cgccaaaatg ctggcgtagt aggtcaagac       720
tctgagacta tcgaactcgc acctgaatac gctgaggcta tcgcaacccg tgcaggtgcg       780
ctggctggca tctctccgat gttccaacct tgcgtagttc ctcctaagcc gtggactggc       840
attactggtg gtggctattg ggctaacggt cgtcgtcctc tggcgctggt gcgtactcac       900
agtaagaaag cactgatgcg ctacgaagac gtttacatgc tgaggtgta caaagcgatt       960 aacattgcgc aaaacaccgc atggaaaatc aacaagaaag tcctagcggt cgccaacgta      1020
atcaccaagt ggaagcattg tccggtcgag gacatccctg cgattgagcg tgaagaactc      1080
ccgatgaaac cggaagacat cgacatgaat cctgaggctc tcaccgcgtg gagacgtgct      1140
gccgctgctg tgtaccgcaa ggacaaggct cgcaagtctc gccgtatcag ccttgagttc      1200
```

```
atgcttgagc aagccaataa gtttgctaac cataaggcca tctggttccc ttacaacatg    1260
gactggcgcg gtcgtgttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggctctgggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta gctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtag ccagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aa                                                         2652
```

<210> SEQ ID NO 124  
<211> LENGTH: 2652  
<212> TYPE: DNA  
<213> ORGANISM: Artificial Sequence  
<220> FEATURE:  
<223> OTHER INFORMATION: chemically synthesized mutant T7 RNA polymerase P266L/Y639L/H784A sequence

<400> SEQUENCE: 124

```
atgaacacga ttaacatcgc taagaacgac ttctctgaca tcgaactggc tgctatcccg    60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta ccgtgacct tgaagctaag    480 cacttcaaga aaaacgttga ggaacaactc aacaagcgcg tagggcacgt ctacaagaaa    540
```

-continued

```
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctctgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag acatccctg cgattgagcg tgaagaactc    1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaagtaaa ccaatcggta aggaaggtta ctactggctg    1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggctctgggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta gctgctggc tgctgaggtc aaagataaga gactggaga gattcttcgc    2160
aagcgttgcg ctgtgcattg ggtaactcct gatggttttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtag ccagccaaga cggtagccac cttcgtaaga ctgtagtgtg gcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aa                                                       2652
```

<210> SEQ ID NO 125
<211> LENGTH: 2652
<212> TYPE: DNA
<213> ORGANISM: Artificial Sequence
<220> FEATURE:
<223> OTHER INFORMATION: chemically synthesized mutant T7 RNA polymerase
      P266L/Y639L/H784A/K378R sequence

<400> SEQUENCE: 125

```
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta ccgtgaccct tgaagctaag     480
cacttcaaga aaacgttga ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctctgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc ctgaggtgta caaagcgatt     960
aacattgcgc aaaacaccgc atggaaaatc aacaagaaag tcctagcggt cgccaacgta    1020
atcaccaagt ggaagcattg tccggtcgag acatccctg cgattgagcg tgaagaactc    1080
ccgatgaaac cggaagacat cgacatgaat cctgaggctc tcaccgcgtg gagacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtgttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta gtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctgggcacta aggcactggc tggtcaatgg    1860
ctggcttacg gtgttactcg cagtgtgact aagcgttcag tcatgacgct ggctctgggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg gtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
```

-continued

```
aactttgtag ccagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aa                                                       2652

<210> SEQ ID NO 126
<211> LENGTH: 89
<212> TYPE: DNA
<213> ORGANISM: Artificial Sequence
<220> FEATURE:
<223> OTHER INFORMATION: chemically synthesized DNA transcription
      template
<220> FEATURE:
<221> NAME/KEY: misc_feature
<222> LOCATION: (24)..(63)
<223> OTHER INFORMATION: n is a, t, c or g

<400> SEQUENCE: 126
gggagaattc cgaccagaag cttnnnnnnn nnnnnnnnnn nnnnnnnnnn nnnnnnnnn    60 nnncatatgt gcgtctacat ggatcctca                                     89

<210> SEQ ID NO 127
<211> LENGTH: 89
<212> TYPE: DNA
<213> ORGANISM: Artificial Sequence
<220> FEATURE:
<223> OTHER INFORMATION: chemically synthesized DNA transcription
      template
<220> FEATURE:
<221> NAME/KEY: misc_feature
<222> LOCATION: (27)..(66)
<223> OTHER INFORMATION: n is a, t, c or g

<400> SEQUENCE: 127
gggagagcgg aagccgtgct ggggcnnnnn nnnnnnnnnn nnnnnnnnnn nnnnnnnnn    60 nnnnnncata acccagaggt cgatggatc                                     89

<210> SEQ ID NO 128
<211> LENGTH: 94
<212> TYPE: DNA
<213> ORGANISM: Artificial Sequence
<220> FEATURE:
<223> OTHER INFORMATION: chemically synthesized DNA transcription
      template
<220> FEATURE:
<221> NAME/KEY: misc_feature
<222> LOCATION: (21)..(60)
<223> OTHER INFORMATION: n is a, t, c or g

<400> SEQUENCE: 128
gggagagaca agcttgggtc nnnnnnnnnn nnnnnnnnnn nnnnnnnnnn nnnnnnnnnn    60
agaagagaaa gagaagttaa ttaaggatcc tcag                               94

<210> SEQ ID NO 129
<211> LENGTH: 86
<212> TYPE: DNA
<213> ORGANISM: Artificial Sequence
<220> FEATURE:
<223> OTHER INFORMATION: chemically synthesized DNA transcription
      template
<220> FEATURE:
<221> NAME/KEY: misc_feature
```

```
<222> LOCATION: (21)..(60)
<223> OTHER INFORMATION: n is a, t, c or g

<400> SEQUENCE: 129
gggagaattc cgaccacaag nnnnnnnnnn nnnnnnnnnn nnnnnnnnnn nnnnnnnnnn    60
catatgtgcg tctacatgga tcctca                                        86

<210> SEQ ID NO 130
<211> LENGTH: 40
<212> TYPE: DNA
<213> ORGANISM: Artificial Sequence
<220> FEATURE:
<223> OTHER INFORMATION: chemically synthesized 5' primer sequence

<400> SEQUENCE: 130
taatacgact cactataggg agaattccga ccagaagctt                         40

<210> SEQ ID NO 131
<211> LENGTH: 26
<212> TYPE: DNA
<213> ORGANISM: Artificial Sequence
<220> FEATURE:
<223> OTHER INFORMATION: chemically synthesized 3' primer sequence

<400> SEQUENCE: 131
tgaggatcca tgtagacgca catatg                                       26

<210> SEQ ID NO 132
<211> LENGTH: 23
<212> TYPE: DNA
<213> ORGANISM: Artificial Sequence
<220> FEATURE:
<223> OTHER INFORMATION: chemically synthesized 3' primer sequence

<400> SEQUENCE: 132
gatccatcga cctctgggtt atg                                          23

<210> SEQ ID NO 133
<211> LENGTH: 37
<212> TYPE: DNA
<213> ORGANISM: Artificial Sequence
<220> FEATURE:
<223> OTHER INFORMATION: chemically synthesized 5' primer sequence

<400> SEQUENCE: 133
taatacgact cactataggg agagacaagc ttgggtc                           37

<210> SEQ ID NO 134
<211> LENGTH: 34
<212> TYPE: DNA
<213> ORGANISM: Artificial Sequence
<220> FEATURE:
<223> OTHER INFORMATION: chemically synthesized 3' primer sequence

<400> SEQUENCE: 134
ctgaggatcc ttaattaact tctctttctc ttct                              34

<210> SEQ ID NO 135
<211> LENGTH: 37
<212> TYPE: DNA
<213> ORGANISM: Artificial Sequence
<220> FEATURE:
<223> OTHER INFORMATION: chemically synthesized 5' primer sequence

<400> SEQUENCE: 135
taatacgact cactataggg agaattccga ccacaag                           37
```

<210> SEQ ID NO 136
<211> LENGTH: 10
<212> TYPE: DNA
<213> ORGANISM: Artificial Sequence
<220> FEATURE:
<223> OTHER INFORMATION: chemically synthesized immunostimulatory motif

<400> SEQUENCE: 136
aacgttcgag                                                          10

<210> SEQ ID NO 137
<211> LENGTH: 76
<212> TYPE: DNA
<213> ORGANISM: Artificial Sequence
<220> FEATURE:
<223> OTHER INFORMATION: chemically synthesized DNA template ARC3428
<220> FEATURE:
<221> NAME/KEY: misc_feature
<222> LOCATION: (24)..(53)
<223> OTHER INFORMATION: n is a, t, c, or g

<400> SEQUENCE: 137
gggagacaag aataaagcga gttnnnnnnn nnnnnnnnnn nnnnnnnnnn nnnaagagtc   60
gatgatgctt agctag                                                   76

<210> SEQ ID NO 138
<211> LENGTH: 77
<212> TYPE: DNA
<213> ORGANISM: Artificial Sequence
<220> FEATURE:
<223> OTHER INFORMATION: chemically synthesized DNA transcription
      template
<220> FEATURE:
<221> NAME/KEY: misc_feature
<222> LOCATION: (24)..(53)
<223> OTHER INFORMATION: n is a, c, g, or t

<400> SEQUENCE: 138
gggccttgta gcgtgcattc ttgnnnnnnn nnnnnnnnnn nnnnnnnnnn nnnctaacat   60
actccgaatc tgtcgaa                                                  77

<210> SEQ ID NO 139
<211> LENGTH: 73
<212> TYPE: DNA
<213> ORGANISM: Artificial Sequence
<220> FEATURE:
<223> OTHER INFORMATION: chemically synthesized DNA transcription
      template
<220> FEATURE:
<221> NAME/KEY: misc_feature
<222> LOCATION: (17)..(56)
<223> OTHER INFORMATION: n is a, c, g, or t

<400> SEQUENCE: 139
ggagccttcc tccggannnn nnnnnnnnnn nnnnnnnnnn nnnnnnnnnn nnnnnntccg   60
gtttcccgag ctt                                                      73

<210> SEQ ID NO 140
<211> LENGTH: 87
<212> TYPE: DNA
<213> ORGANISM: Artificial Sequence
<220> FEATURE:
<223> OTHER INFORMATION: chemically synthesized DNA transcription
      template
<220> FEATURE:
<221> NAME/KEY: misc_feature
<222> LOCATION: (24)..(63)

<223> OTHER INFORMATION: n is a, c, g, or t

<400> SEQUENCE: 140
gggagacaag aataaacgct caannnnnnn nnnnnnnnnn nnnnnnnnnn nnnnnnnnnn    60
nnnttcgaca ggaggctcac aacaggc    87

<210> SEQ ID NO 141
<211> LENGTH: 24
<212> TYPE: DNA
<213> ORGANISM: Artificial Sequence
<220> FEATURE:
<223> OTHER INFORMATION: chemically synthesized 3' primer sequence

<400> SEQUENCE: 141
ttcgacagat tcggagtatg ttag    24

<210> SEQ ID NO 142
<211> LENGTH: 33
<212> TYPE: DNA
<213> ORGANISM: Artificial Sequence
<220> FEATURE:
<223> OTHER INFORMATION: chemically synthesized 5' primer sequence

<400> SEQUENCE: 142
taatacgact cactatagga gccttcctcc gga    33

<210> SEQ ID NO 143
<211> LENGTH: 17
<212> TYPE: DNA
<213> ORGANISM: Artificial Sequence
<220> FEATURE:
<223> OTHER INFORMATION: chemically synthesized 3' primer sequence

<400> SEQUENCE: 143
aagctcggga aaccgga    17

<210> SEQ ID NO 144
<211> LENGTH: 40
<212> TYPE: DNA
<213> ORGANISM: Artificial Sequence
<220> FEATURE:
<223> OTHER INFORMATION: chemically synthesized 5' primer sequence

<400> SEQUENCE: 144
taatacgact cactataggg agacaagaat aaacgctcaa    40

<210> SEQ ID NO 145
<211> LENGTH: 24
<212> TYPE: DNA
<213> ORGANISM: Artificial Sequence
<220> FEATURE:
<223> OTHER INFORMATION: chemically synthesized 3' primer sequence

<400> SEQUENCE: 145
gcctgttgtg agcctcctgt cgaa    24

<210> SEQ ID NO 146
<211> LENGTH: 39
<212> TYPE: DNA
<213> ORGANISM: Artificial Sequence
<220> FEATURE:
<223> OTHER INFORMATION: chemically synthesized 5' primer sequence

<400> SEQUENCE: 146
taatacgact cactataggg gagtacaata accagacat    39

```
<210> SEQ ID NO 147
<211> LENGTH: 24
<212> TYPE: DNA
<213> ORGANISM: Artificial Sequence
<220> FEATURE:
<223> OTHER INFORMATION: chemically synthesized 3' primer sequence

<400> SEQUENCE: 147
catcgatgct agtcgtaacg atcc                                          24

<210> SEQ ID NO 148
<211> LENGTH: 26
<212> TYPE: DNA
<213> ORGANISM: Artificial Sequence
<220> FEATURE:
<223> OTHER INFORMATION: chemically synthesized 3' primer sequence

<400> SEQUENCE: 148
tgaggatcca tgtagacgca catatg                                        26

<210> SEQ ID NO 149
<211> LENGTH: 43
<212> TYPE: DNA
<213> ORGANISM: Artificial Sequence
<220> FEATURE:
<223> OTHER INFORMATION: chemically synthesized 5' primer sequence

<400> SEQUENCE: 149
taatacgact cactataggg agagcggaag ccgtgctggg gcc                     43

<210> SEQ ID NO 150
<211> LENGTH: 76
<212> TYPE: DNA
<213> ORGANISM: Artificial Sequence
<220> FEATURE:
<223> OTHER INFORMATION: chemically synthesized DNA transcription
      template
<220> FEATURE:
<221> NAME/KEY: misc_feature
<222> LOCATION: (23)..(52)
<223> OTHER INFORMATION: n is a, c, g, or t

<400> SEQUENCE: 150
ggggagtaca ataaccagac atnnnnnnnn nnnnnnnnnn nnnnnnnnnn nnggatcgtt   60
acgactagca tcgatg                                                   76

<210> SEQ ID NO 151
<211> LENGTH: 40
<212> TYPE: DNA
<213> ORGANISM: Artificial Sequence
<220> FEATURE:
<223> OTHER INFORMATION: chemically synthesized 5' primer sequence

<400> SEQUENCE: 151
taatacgact cactataggg ccttgtagcg tgcattcttg                         40
```